US 9,224,179 B2

(12) United States Patent
Courdy et al.

(10) Patent No.: US 9,224,179 B2
(45) Date of Patent: Dec. 29, 2015

(54) METHOD AND SYSTEM FOR REPORT GENERATION INCLUDING EXTENSIBLE DATA

(75) Inventors: Samir Courdy, Sandy, UT (US); Cynthia Spigle, Salt Lake City, UT (US); Carolyn Ross, Holladay, UT (US); Tonya Di Sera, Holladay, UT (US); Cody Haroldsen, Sandy, UT (US); Jason Holmberg, Salt Lake City, UT (US)

(73) Assignee: The University of Utah Research Foundation, Salt Lake City, UT (US)

( * ) Notice: Subject to any disclaimer, the term of this patent is extended or adjusted under 35 U.S.C. 154(b) by 1530 days.

(21) Appl. No.: 11/748,125

(22) Filed: May 14, 2007

(65) Prior Publication Data
US 2008/0319942 A1 Dec. 25, 2008

(51) Int. Cl.
G06F 17/30 (2006.01)
G06Q 50/22 (2012.01)
G06F 19/00 (2011.01)
G06Q 10/10 (2012.01)

(52) U.S. Cl.
CPC .............. G06Q 50/22 (2013.01); G06F 19/322 (2013.01); G06F 19/3443 (2013.01); G06F 19/3487 (2013.01); G06Q 10/10 (2013.01)

(58) Field of Classification Search
CPC .......... G06F 3/0416; G06F 2206/1008; G06F 19/3406; G06F 3/1454; G06F 3/038
USPC ......................................... 707/706, 736, 805
See application file for complete search history.

(56) References Cited

U.S. PATENT DOCUMENTS

| | | | |
|---|---|---|---|
| 5,524,238 A | 6/1996 | Miller et al. | |
| 5,772,585 A * | 6/1998 | Lavin et al. | 600/300 |
| 5,838,973 A * | 11/1998 | Carpenter-Smith et al. | 717/105 |
| 6,065,002 A | 5/2000 | Knotts et al. | |
| 6,322,502 B1 * | 11/2001 | Schoenberg et al. | 600/300 |
| 7,213,208 B2 | 5/2007 | Reichel et al. | |
| 2003/0110464 A1 * | 6/2003 | Davidson et al. | 716/17 |
| 2006/0004725 A1 * | 1/2006 | Abraido-Fandino | 707/3 |
| 2006/0047760 A1 * | 3/2006 | Encinas et al. | 709/206 |
| 2006/0080083 A1 * | 4/2006 | Lin et al. | 704/8 |
| 2006/0147891 A1 * | 7/2006 | Dreyfous et al. | 434/362 |

(Continued)

OTHER PUBLICATIONS

International Search Report and Written Opinion for PCT/US2008/063430 dated Oct. 30, 2008.
Thomson Reuters, ELITE Prolaw Virtual Conference, printed from http://www.elite.com/prolaw/virtual_conference/sessions/, Oct. 19, 2009, pp. 1-5.

(Continued)

Primary Examiner — James Trujillo
Assistant Examiner — Fatima Mina
(74) Attorney, Agent, or Firm — Workman Nydegger

(57) ABSTRACT

A method of extending a user interface to include additional data fields is provided. A first response is received at a first application. The first response indicates a selection of an add button associated with addition of a data field to a first window associated with a user interface of a second application. A second window is presented to a user of the first application. A second response is received at the first application. The second response includes a name for the data field entered by the user using the presented second window and a data type of the data field. A position of the data field is identified on the first window. The received name, the received data type, and the identified position for the data field are stored. The data field is presented in the first window at the stored position using the stored name when a second user executes the second application.

19 Claims, 39 Drawing Sheets

(56) References Cited

U.S. PATENT DOCUMENTS

2006/0229928 A1* 10/2006 Nix, Jr. ............................. 705/9
2007/0127597 A1*  6/2007 Ammer et al. ................. 375/324
2008/0021739 A1*  1/2008 Brock ............................... 705/3
2008/0198856 A1*  8/2008 Vogel et al. ................ 370/395.3

OTHER PUBLICATIONS

Thomson Reuters, ELITE Online Education, printed from http://www.elite.com/education/prolaw-online-education/, Jun. 4, 2010, pp. 1-3.

* cited by examiner

| | MRN | Last Name | First Name | Birth Date | Age | Deceased? | Sex | First Visit |
|---|---|---|---|---|---|---|---|---|
| 1 | HC1000166 | TEST | CLS1 | Aug 5, 1994 | 12 | ☐ | F | |
| 2 | HC1000146 | TESTCLS | CLS | Aug 3, 1973 | 33 | ☐ | F | Apr 24, 2006 |
| 3 | ACIS-005 | TEST | FIVE | Jun 5, 1997 | 9 | ✓ | F | Aug 7, 2006 |
| 4 | ACIS-004 | TEST | FOUR | May 4, 1932 | 74 | ☐ | | |
| 5 | ACIS-001 | TEST | ONE | Jan 1, 1965 | 41 | ✓ | M | |
| 6 | ACIS-006 | TEST | SIX | Jul 9, 1980 | 26 | ☐ | M | |
| 7 | ACIS-003 | TEST | THREE | May 2, 1995 | 11 | ☐ | F | |
| 8 | ACIS-002 | TEST | TWO | Aug 6, 1942 | 64 | ☐ | F | Aug 8, 2006 |

8 Patient(s) found.

Samples

Search Samples

Cancer Center #: [04]  Go
HCI Number: [  ]  Go
Disbursed Project: [ ▼ ]  Go
Tissue Type and Cancer Status: [ ▼ ] [ ▼ ]  Go
Patient with MRN: [  ]  Go
Patient with SP #: [  ]  Go 1502 → Add Sample

Administration

Administer Users

Update Dictionaries

Overview | | | | Administration | | Labs | | Medical Event
---|---|---|---|---|---|---|---|---
Medical Events List | | | | | view events: | ○ by Classification ● by Date | ○ by Tumor |
Start Date | Classification | Event Type | Detailed Proced | Report Number | CPT Code | | | |
2005/01/01 | Diagnosis | Tumor Biopsy | Needle under... | | 46102 | | | |
2005/02/01 | Diagnosis | Radiation Ther... | | | | | | |
2005/03/01 | Diagnosis | Imaging | X-ray bile-pan... | | 74330 | | | |
2005/04/01 | Follow-up | Functional Eva... | | | | | | |
2005/06/01 | Treatment | Surgery | Pancreatecto... | | 48152 | | | |
2005/06/01 | Treatment | Surgical Revisi... | | | | | | |

Fig. 20

Overview | | | | Administration | | Labs | | Medical Event
---|---|---|---|---|---|---|---|---
Medical Events List | | | | | view events: | ○ by Classification ● by Date | ○ by Tumor |
Tumor Type | Classification | Event Type | Start Date | Detailed Procedure | Report Number | CPT Code | | |
▼ Soft Tissue (2) | | | | | | | | |
 | Diagnosis | Tumor Biopsy | 2005/01/01 | Incisional biopsy | | 46103 | | |
 | Diagnosis | Radiation Ther... | 2005/02/01 | Brachytherapy | | 77623 | | |
▼ Bone (2) | | | | | | | | |
 | Treatment | Surgery | 2005/06/01 | Hemijoint Resection | | 20552 | | |
 | Treatment | Surgical Revisi... | 2005/06/01 | Bone Graft | | 38220 | | |

| Overview | | Administration | | Labs | | Medical Event |
|---|---|---|---|---|---|---|
| Medical Events List | | | | View events: ● by Classification ○ by Date ○ by Tumor | | |
| Classification | Event Type | Start Date | Detailed Procedure | | Report Number | CPT Code |
| ▼ Diagnosis (3) | | | | | | |
| | Tumor Biopsy | 2005/01/01 | Needle under ultrasound | | | 46102 |
| | Radiation Therapy | 2005/02/01 | | | | |
| | Imaging | 2005/03/01 | X-ray bile/pancreas | | | 74330 |
| ▼ Follow-up (1) | | | | | | |
| | Functional Evaluation | 2005/04/01 | | | | |
| ▼ Treatment (2) | | | | | | |
| | Surgery | 2005/06/01 | Pancreatectomy (Whipple p... | | | 48152 |
| | Surgical Revision | 2005/06/01 | | | | |

METHOD AND SYSTEM FOR REPORT GENERATION INCLUDING EXTENSIBLE DATA

FIELD

The field of the disclosure relates generally to computer systems. More specifically, the disclosure relates to a method and a system for generating reports that include extensible data added by an end user to an existing application.

BACKGROUND

Currently, there is no common repository for cancer specific clinical and research data to support translational research. Clinical research programs are interested in collecting a detailed set of clinical and research information on their patients that is easy to maintain and from which relevant data can be analyzed and extracted. The information needed is not a repetition of the existing electronic medical record, but instead provides additional, complementary, and specific information for analysis and presentation of the data for various research studies. Each program, however, has established their own mechanisms for extracting, recording, and using this data, using a variety of technical approaches. These mechanisms have so far been incomplete, difficult to maintain, and difficult to extract data from. Thus, what is needed is a method and a system for allowing the user to extend the research application to collect additional data in combination with pre-defined data collection. What is additionally needed is a method and a system for allowing the generation of reports which include the extensible data added to the application for collection, analysis, and information extraction.

SUMMARY

In an exemplary embodiment, a device for extending a user interface to include additional data fields is provided. The device includes a computer-readable medium having computer-readable instructions therein and a processor coupled to the computer-readable medium and configured to execute the instructions. The instructions include receiving a first response at a first application, wherein the first response indicates a first selection of an add button. The add button is associated with addition of a data field to a first window associated with a user interface of a second application. The instructions further include presenting a second window to a user of the first application and receiving a second response at the first application. The second response includes a name for the data field entered by the user using the presented second window and a data type of the data field. The instructions still further include identifying a position of the data field on the first window and storing the received name, the received data type, and the identified position for the data field. The data field is presented in the first window at the stored position using the stored name when a second user executes the second application;

In another exemplary embodiment, a method of extending a user interface to include additional data fields is provided. A first response is received at a first application. The first response indicates a selection of an add button associated with addition of a data field to a first window associated with a user interface of a second application. A second window is presented to a user of the first application. A second response is received at the first application. The second response includes a name for the data field entered by the user using the presented second window and a data type of the data field. A position of the data field is identified on the first window. The received name, the received data type, and the identified position for the data field are stored. The data field is presented in the first window at the stored position using the stored name when a second user executes the second application.

In yet another exemplary embodiment, computer-readable instructions are provided that, upon execution by a processor, cause the processor to implement the operations of the method.

Other principal features and advantages of the invention will become apparent to those skilled in the art upon review of the following drawings, the detailed description, and the appended claims.

BRIEF DESCRIPTION OF THE DRAWINGS

Exemplary embodiments of the invention will hereafter be described with reference to the accompanying drawings, wherein like numerals denote like elements.

FIG. 4 depicts a window listing patients identified from a search using the main window of FIG. 3 in accordance with an exemplary embodiment.

FIG. 5 depicts an advanced search window of the medical research application in accordance with an exemplary embodiment.

FIGS. 7a and 7b depict a patient detail window of the medical research application in accordance with an exemplary embodiment.

FIG. 7c depicts an additional patient information window of the medical research application in accordance with an exemplary embodiment.

FIG. 8 depicts a diagnosis detail window of the medical research application in accordance with an exemplary embodiment.

FIG. 12 depicts an administration tab of the patient detail window of FIGS. 7a and 7b in accordance with an exemplary embodiment.

FIG. 14 depicts a sample detail window of a bio-sample tracking application in accordance with an exemplary embodiment.

FIG. 15 depicts a main menu window of the bio-sample tracking application in accordance with an exemplary embodiment.

FIG. 16 depicts an add sample window of the bio-sample tracking application in accordance with an exemplary embodiment.

FIG. 18 depicts an add test window of the medical research application in accordance with an exemplary embodiment.

FIG. 19 depicts a first medical event tab of the patient detail window of FIGS. 7a and 7b in accordance with an exemplary embodiment.

FIG. 20 depicts a second medical event tab of the patient detail window of FIGS. 7a and 7b in accordance with an exemplary embodiment.

FIG. 21 depicts a third medical event tab of the patient detail window of FIGS. 7a and 7b in accordance with an exemplary embodiment.

FIG. 23 depicts a details tab of the medical event detail window of FIG. 22 in accordance with an exemplary embodiment.

FIG. 26 depicts a pathology report detail window of the medical research application in accordance with an exemplary embodiment.

Figure 27:
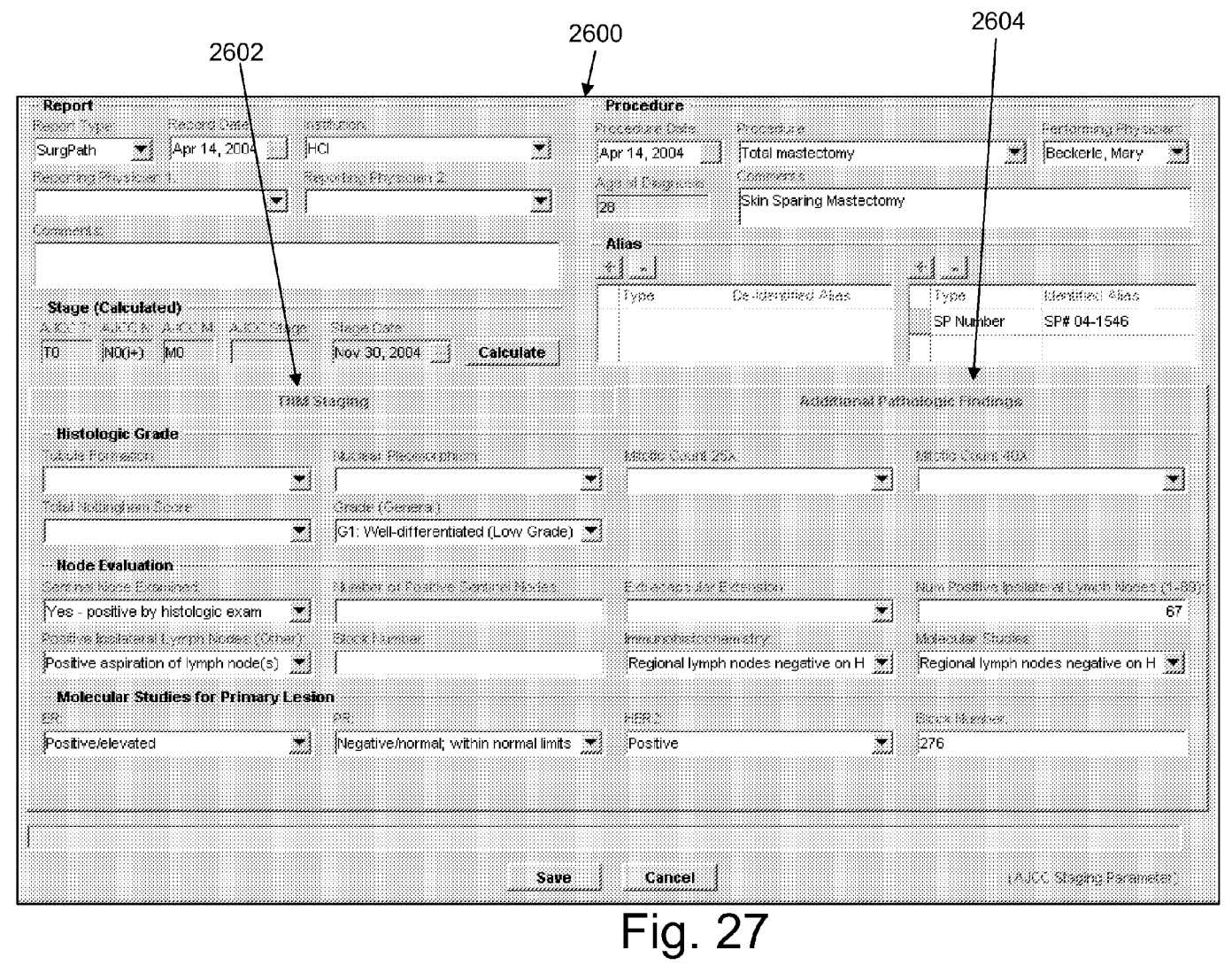

FIG. 27 depicts a second tab of the pathology report detail window of FIG. 26 in accordance with an exemplary embodiment.

DETAILED DESCRIPTION

Figure 1:
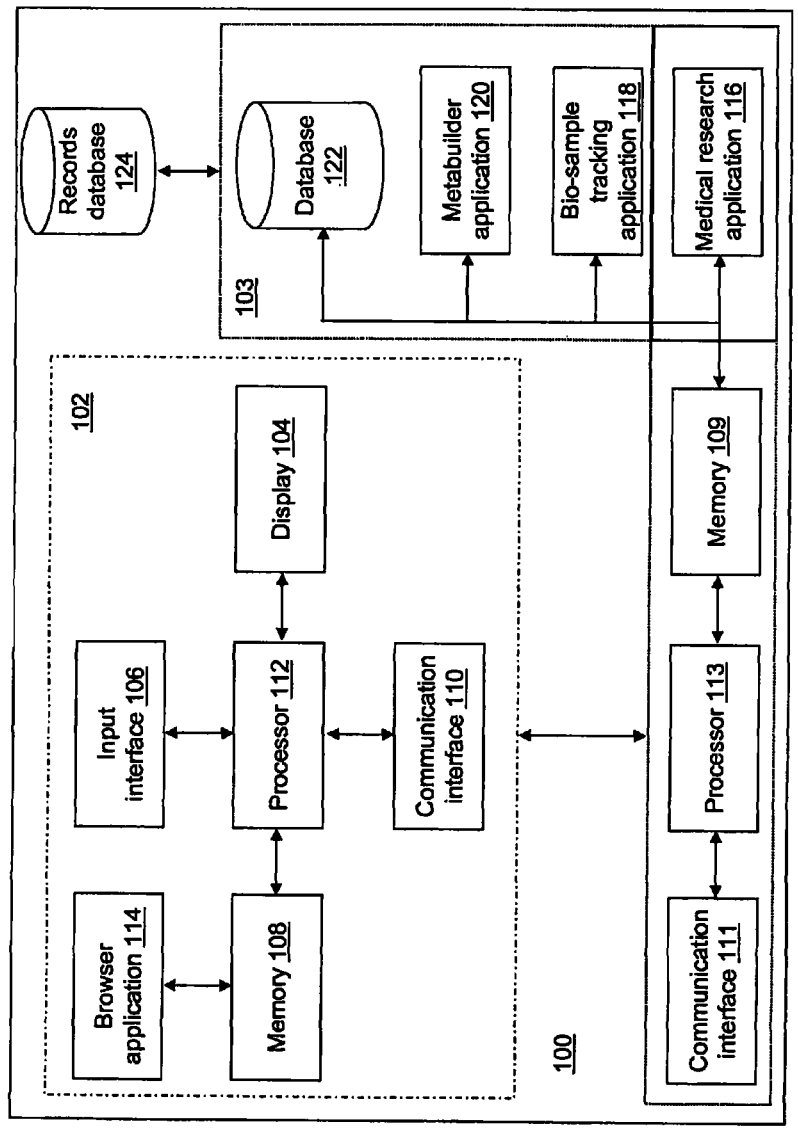
FIG. 1 depicts a block diagram of a medical research system in accordance with an exemplary embodiment.

With reference to FIG. 1, a block diagram of a medical research system 100 is shown in accordance with an exemplary embodiment. The term "exemplary" is used herein to mean serving as an example, instance, or illustration. Any aspect or design described herein as "exemplary" is not necessarily to be construed as preferred or advantageous over other aspects or designs. Medical research system 100 may include a first computing device 102, a second computing device 103, and a records database 124 which may be stored at first computing device 102, at second computing device 103, or at a third computing device. Records database 124 includes electronic medical records that provide demographics, encounters, results and diagnostic information from a clinical system for a plurality of patients.

First computing device 102 may include a display 104, an input interface 106, a first memory 108, a first communication interface 110, a first processor 112, and a browser application 114. Second computing device 103 may include a second memory 109, a second communication interface 111, a second processor 113, a medical research application 116, a bio-sample tracking application 118, a metabuilder application 120, and a database 122. Different and additional components may be incorporated into medical research system 100, first computing device 102, and second computing device 103. For example, computing device 102 may also include medical research application 116, bio-sample tracking application 118, metabuilder application 120, and/or database 122. Medical research application 116, bio-sample tracking application 118, metabuilder application 120, and database 122 may be implemented in one or more computing devices. Thus, the components of medical research system 100 may be positioned in a single device or a plurality of devices in a single location, in a single facility, and/or remote from one another.

Display 104 presents information to a user of first computing device 102 as known to those skilled in the art. For example, display 104 may be a thin film transistor display, a light emitting diode display, a liquid crystal display, or any of a variety of different displays known to those skilled in the art now or in the future.

Input interface 106 provides an interface for receiving information from the user for entry into first computing device 102 as known to those skilled in the art. Input interface 106 may use various input technologies including, but not limited to, a keyboard, a pen and touch screen, a mouse, a track ball, a touch screen, a keypad, one or more buttons, etc. to allow the user to enter information into first computing device 102 or to make selections presented in a user interface displayed on display 104. Input interface 106 may provide both an input and an output interface. For example, a touch screen both allows user input and presents output to the user.

First memory 108 is an electronic holding place or storage for information so that the information can be accessed by first processor 110 as known to those skilled in the art. Second memory 109 is an electronic holding place or storage for information so that the information can be accessed by second processor 113 as known to those skilled in the art. First computing device 102 and second computing device 103 may have one or more memories that use the same or a different memory technology. First computing device 102 and second computing device 103 may have one or more memories that use the same or a different memory technology. Memory technologies include, but are not limited to, any type of RAM, any type of ROM, any type of flash memory, etc. First computing device 102 and second computing device 103 also may have one or more drives that support the loading of a memory media such as a compact disk or digital video disk.

First communication interface 110 provides an interface for receiving and transmitting information communicable between computing devices. Second communication interface 111 provides an interface for receiving and transmitting information communicable between computing devices. Communications between first computing device 102, second computing device 103 and other devices may use various transmission technologies and media as known to those skilled in the art.

First processor 112 and second processor 113 execute instructions as known to those skilled in the art. The instructions may be carried out by a special purpose computer, logic circuits, or hardware circuits. Thus, first processor 112 and second processor 113 may be implemented in hardware, firmware, software, or any combination of these methods. The term "execution" is the process of running an application or the carrying out of the operation called for by an instruction. The instructions may be written using one or more programming language, scripting language, assembly language, etc. First processor 112 and second processor 113 execute an instruction, meaning that they perform the operations called for by that instruction. First processor 112 may operably couple with display 104, with input interface 106, with first memory 108, and with first communication interface 110 to receive, to send, and to process information. Second processor 113 may operably couple with second memory 109 and with second communication interface 111 to receive, to send, and to process information. First processor 112 and second processor 113 may retrieve a set of instructions from a permanent memory device and copy the instructions in an executable form to a temporary memory device that is generally some form of RAM. First computing device 102 and second computing device 103 may include a plurality of processors that use the same or a different processing technology.

First computing device 102 and second computing device 103 may include computers of any form factor such as a laptop, a desktop, an integrated messaging device, a personal digital assistant, etc. First computing device 102 and second computing device 103 may interact using a network such as a local area network, a wide area network, a cellular network, the Internet, etc. If implemented in separate computing devices, medical research application 116, bio-sample tracking application 118, metabuilder application 120, and database 122 may communicate using the same or a different network.

Database 122 can be a standard structured query language (SQL) database. Database 122 may store information for use by medical research application 116, bio-sample tracking application 118, and/or metabuilder application 120. Database 122 may be organized into multiple databases to improve data management and access. The multiple databases may be organized into tiers.

Computing devices may act as web servers providing information or data organized in the form of websites accessible over a network. A website may comprise multiple web pages that display a specific set of information and may contain links to other web pages with related or additional information. Each web page is identified by a Uniform Resource Locator (URL) that includes the location or address of the computing device that contains the resource to be accessed in addition to the location of the resource on that computing device. The type of file or resource depends on the Internet application protocol. For example, the Hypertext Transfer Protocol (HTTP) describes a web page to be accessed with a browser application. The file accessed may be a simple text file, an image file, an audio file, a video file, an executable, a common gateway interface application, a Java applet, or any other type of file supported by HTTP.

In an exemplary embodiment, medical research application 116, bio-sample tracking application 118, and metabuilder application 120 are web applications, which can be accessed using browser application 114 from first computing device 102 using a network such as the Internet. Thus, medical research application 116, bio-sample tracking application 118, and metabuilder application 120 may be accessed, for example, using a URL entered in a browser address window of browser application 114 as known to those skilled in the art. Medical research application 116, bio-sample tracking application 118, and metabuilder application 120 may communicate with database 122 directly or over a network.

Medical research application 116 performs operations associated with conducting medical research based on patient medical histories. Some or all of the operations and interfaces subsequently described may be embodied in medical research application 116. The operations may be implemented using hardware, firmware, software, or any combination of these methods. With reference to the exemplary embodiment of FIG. 1, medical research application 116 is implemented in software stored in second memory 109 and accessible by second processor 113 for execution of the instructions that embody the operations of medical research application 116. Medical research application 116 may be written using one or more programming languages, assembly languages, scripting languages, etc. Medical research application 116 may integrate with or otherwise interact with bio-sample tracking application 118 and/or metabuilder application 120.

Bio-sample tracking application 118 performs operations associated with finding and accessing information related to biological samples. Some or all of the operations and interfaces subsequently described may be embodied in bio-sample tracking application 118. The operations may be implemented using hardware, firmware, software, or any combination of these methods. With reference to the exemplary embodiment of FIG. 1, bio-sample tracking application 118 is implemented in software stored in second memory 109 and accessible by second processor 113 for execution of the instructions that embody the operations of bio-sample tracking application 118. Bio-sample tracking application 118 may be written using one or more programming languages, assembly languages, scripting languages, etc. Bio-sample tracking application 118 may integrate with or otherwise interact with medical research application 116 and/or metabuilder application 120.

Metabuilder application 120 performs operations associated with extending the functionality of an application based on user requirements. Some or all of the operations and interfaces subsequently described may be embodied in metabuilder application 120. The operations may be implemented using hardware, firmware, software, or any combination of these methods. With reference to the exemplary embodiment of FIG. 1, metabuilder application 120 is implemented in software stored in second memory 109 and accessible by second processor 113 for execution of the instructions that embody the operations of metabuilder application 120. Metabuilder application 120 may be written using one or more programming languages, assembly languages, scripting languages, etc. Metabuilder application 120 may integrate with or otherwise interact with medical research application 116 and/or bio-sample tracking application 118.

Exemplary embodiments are described herein with reference to medical research. Application to medical research is not intended to be limiting. In general, information to be tracked in support of medical research is associated with a patient. In order to be considered a patient for a specific medical condition, such as cancer, arthritis, Alzheimer's, diabetes, a patient may be linked to that medical condition group. In the exemplary embodiments shown and described herein, the medical condition is cancer though use of cancer as a medical condition is not intended to be limiting.

Figure 2:
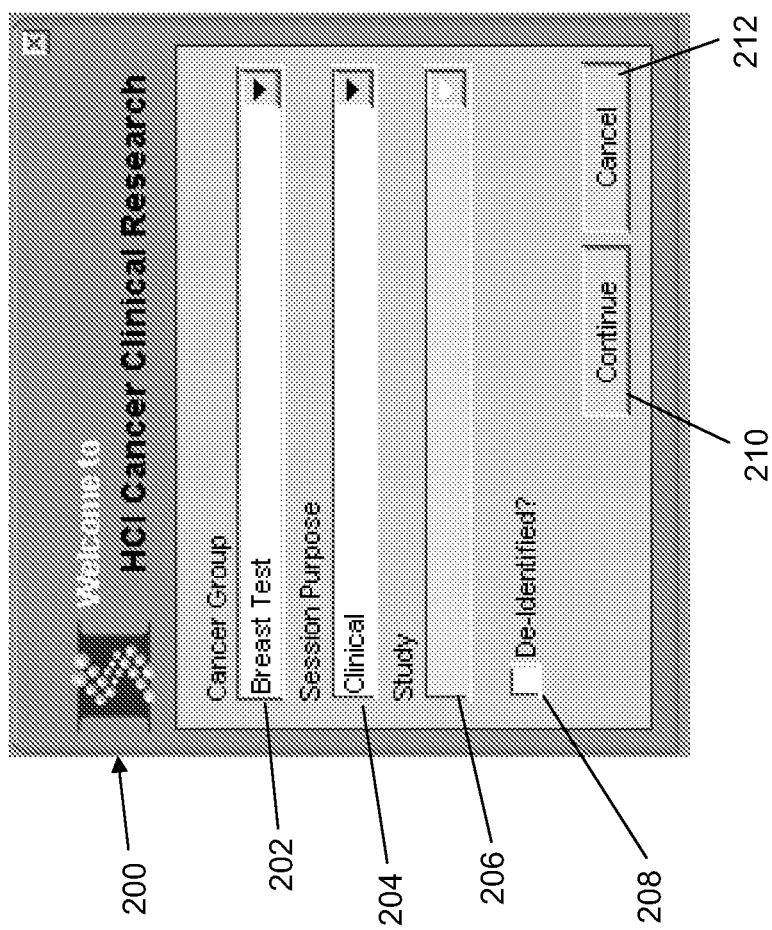
FIG. 2 depicts a welcome window of a medical research application of the medical research system in accordance with an exemplary embodiment.

In an exemplary embodiment, a user may access medical research application 116 from first computing device 102 using browser application 114 and known login procedures. After a user is validated based on authentication using a username/password, a welcome screen 200 may be presented as shown with reference to FIG. 2 in accordance with an exemplary embodiment. Welcome screen 200, for example, presented at display 104 using browser application 114, provides an entry point to medical research application 116. Welcome screen 200 may include a cancer group selector 202, a session purpose selector 204, a study selector 206, a de-identified selector 208, a continue button 210, and a cancel button 212. Cancer group selector 202, session purpose selector 204, and study selector 206 determine the user's role during the session. The options selectable using cancer group selector 202, session purpose selector 204, and study selector 206 may be determined based on control parameters defined for the user based on the authentication process and may be presented using drop down menus.

A cancer group of interest is selected using cancer group selector 202 if more than one cancer group is accessible by the user based on the control parameters associated with the user's username. Cancer group selector 202 may be a drop-down box. A session purpose is selected using session purpose selector 204 which may include options such as: clinical, quality assurance, research/general, research/study, etc. Session purpose selector 204 may be a drop-down box. A study is selected using study selector 206, which may be a drop-down box. For example, if the selected session purpose is research/study, the user may select a study from a list of studies sponsored by the selected cancer group to which the user has been granted access.

The user may choose to work with patient data that does not include patient identification information by selecting de-identified selector 208, which may be a checkbox. Medical research application 116 may display the cancer group, session purpose, study, and de-identified status prominently throughout the session for user reference. After login, patients and information retrieved during the session may be limited based on the selected user role and permissions associated with the user, the selected session purpose, and the de-identified status. If the selected session purpose is research/study, patients retrieved may be limited to those who have consented to inclusion in the study. A patient may be linked to more than one medical condition group. Some information may be shared across medical condition groups. For example, basic demographic information may be shared by all medical condition groups and all applications within medical research system 100.

User selection of cancel button 212 may end the session. After user selection of continue button 210, the user may be presented a main menu 300, shown with reference to FIG. 3 in accordance with an exemplary embodiment. In an exemplary embodiment, main menu 300 allows the user to quickly find a patient, add a patient, or invoke reporting and administration functions associated with medical research application 116. Main menu 300 may include a text box 301, which indicates the cancer group, session purpose, and study selections made by the user from welcome screen 200. Main menu 300 further may include a patient look-up section, a patient quick search section, and a common task section. The patient look-up and patient quick search sections provide common criteria for finding a patient. The searches may be limited to patients in the cancer group specified for the session and to consented patients for a study if the session purpose is Research/Study, for example.

The patient look-up section may include a patient look-up text box 302 and a proceed button 304. The user may enter a medical record number (MRN) into patient look-up text box 302 and select proceed button 304 using input interface 106. Database 122 is searched using the entered MRN and matching information is returned to the user. The patient quick search section may include patient name text boxes 306, date range boxes 308 for the patient's first visit, a medical event type selector 310, a patient classification selector 311, a stage selector 312, and a search button 314. The user enters data into and/or selects data from patient name text boxes 306, date range boxes 308, medical event type selector 310, patient classification selector 311, and stage selector 312 before selecting search button 314. For example, patient classification selector 311 may be implemented as a drop down box which includes user defined selections which can be different for example for each cancer group. Exemplary classifications may include: "Dr. 'X' Patients", "Needs Review", "Surgical Candidate", etc. Database 122 is searched using the entered/selected data and matching information is returned to the user.

With reference to FIG. 4, a search results window 400 provides the matching patient information to the user of computing device 102. Search results window 400 may include a list of patients 402 and a list of patient identification information 404. For example, the list of patient identification information 404 includes, the MRN, the last name, the first name, the birth date, the age, the deceased status, the sex, and the first visit date for each matching patient in the list of patients 402.

Figure 3:
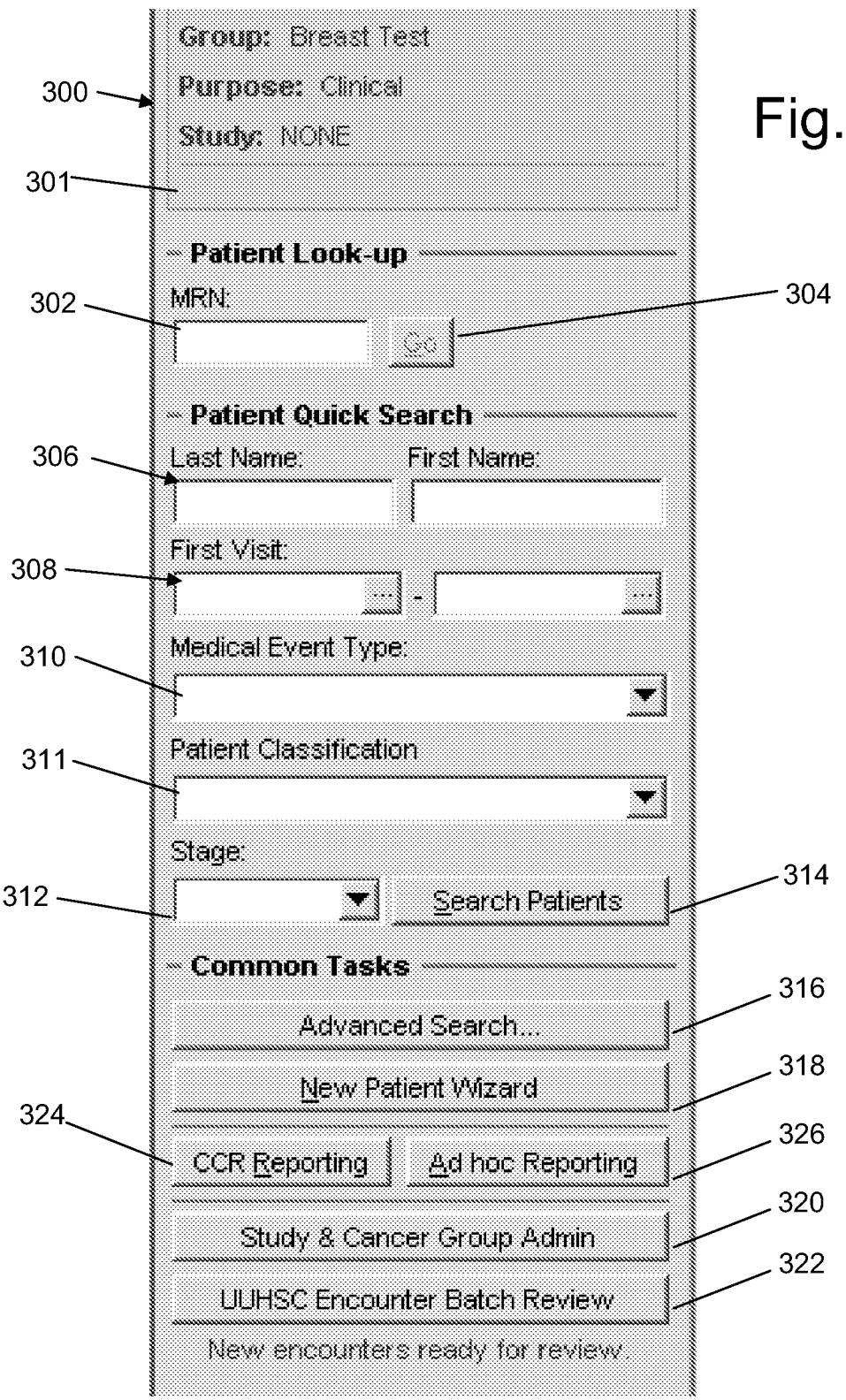
FIG. 3 depicts a main window of the medical research application of FIG. 2 in accordance with an exemplary embodiment.
Figure 5:
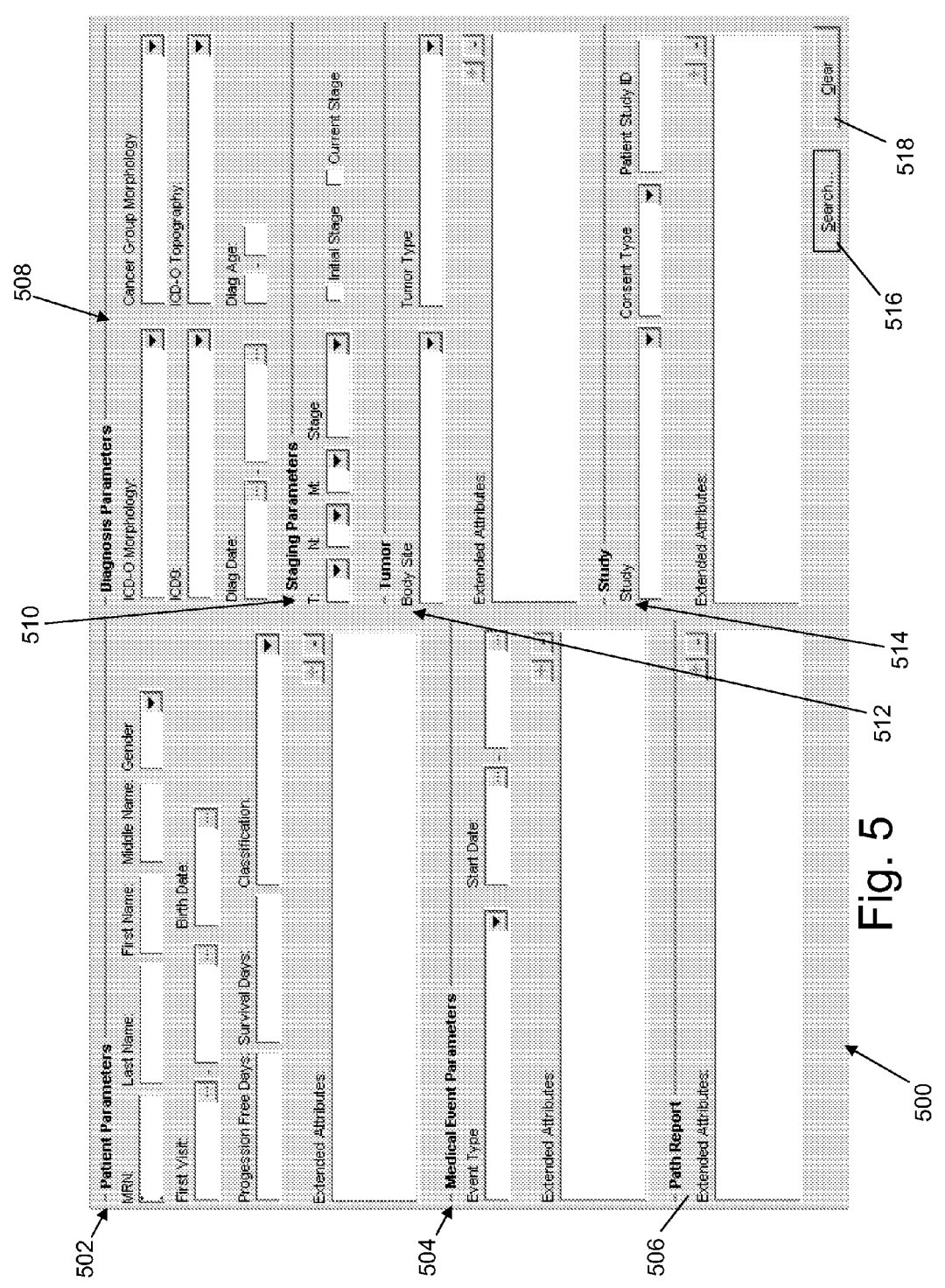

With continued reference to FIG. 3, the common tasks section may include an advanced search button 316, a new patient wizard button 318, an administration button 320, an encounter review button 322, a reporting button 324, and an ad hoc reporting button 326. Selection of advanced search button 316 causes presentation of a search screen for finding groups of patients with shared characteristics. With reference to FIG. 5, an advanced search criteria selection window 500 presented to the user allows the user to specify search criteria for identifying one or more patient from database 122 and/or records database 124. Advanced search criteria selection window 500 allows many more search criteria to be used in identifying a patient or a group of patients that share similar characteristics within the cancer group or study context.

Advanced search criteria selection window 500 may include a patient parameters section 502, a medical event parameters section 504, a pathology report section 506, a diagnosis parameters section 508, a staging parameters section 510, a tumor section 512, a study section 514, a search button 516, and a clear button 518. Patient parameters entered/selected by the user in patient parameters section 502 may include MRN, last name, first name, middle name, gender, first visit date, birth date, progression free days, survival days, classification, and extended attributes which can be custom defined as described later with reference to metabuilder application 120. Medical event parameters entered/selected by the user in medical event parameters section 504 may include event type, start date, and extended attributes which can be custom defined as described later with reference to metabuilder application 120. Pathology reports entered by the user in pathology report section 506 may include extended attributes which can be custom defined as described later with reference to metabuilder application 120. Diagnosis parameters entered/selected by the user in diagnosis parameters section 508 may include International classification of diseases for oncology (ICD-O) morphology, cancer group morphology, ICD 9$^{th}$ edition (ICD-9), ICD-O topography, diagnosis date, and diagnosis age. Staging parameters entered/selected by the user in staging parameters section 510 may include a tumor size status, a lymph node spread status, a metastasis status (TNM status), a stage selector, an initial stage indicator, and a current stage indicator. Tumor parameters entered/selected by the user in tumor section 512 may include a body site selector, a tumor type selector, and extended attributes which can be custom defined as described later with reference to metabuilder application 120. Study parameters entered/selected by the user in study section 514 may include a study selector, a consent type selector, a patient study identifier, and extended attributes which can be custom defined as described later with reference to metabuilder application 120.

The user enters as many search criteria as needed and selects search button 516. Clear button 518 can be selected to blank out all selections in advanced search criteria selection window 500. To select search criteria from one of the extended attributes, a '+' button may be selected. A dialog window (not shown) may be presented which presents the user with a list of attributes available for selection. After selecting search button 516, the user is presented with a list of patients that match the search criteria. For example, search results window 400 may be presented with a list of matching patients as described with reference to FIG. 4.

Figure 6A:
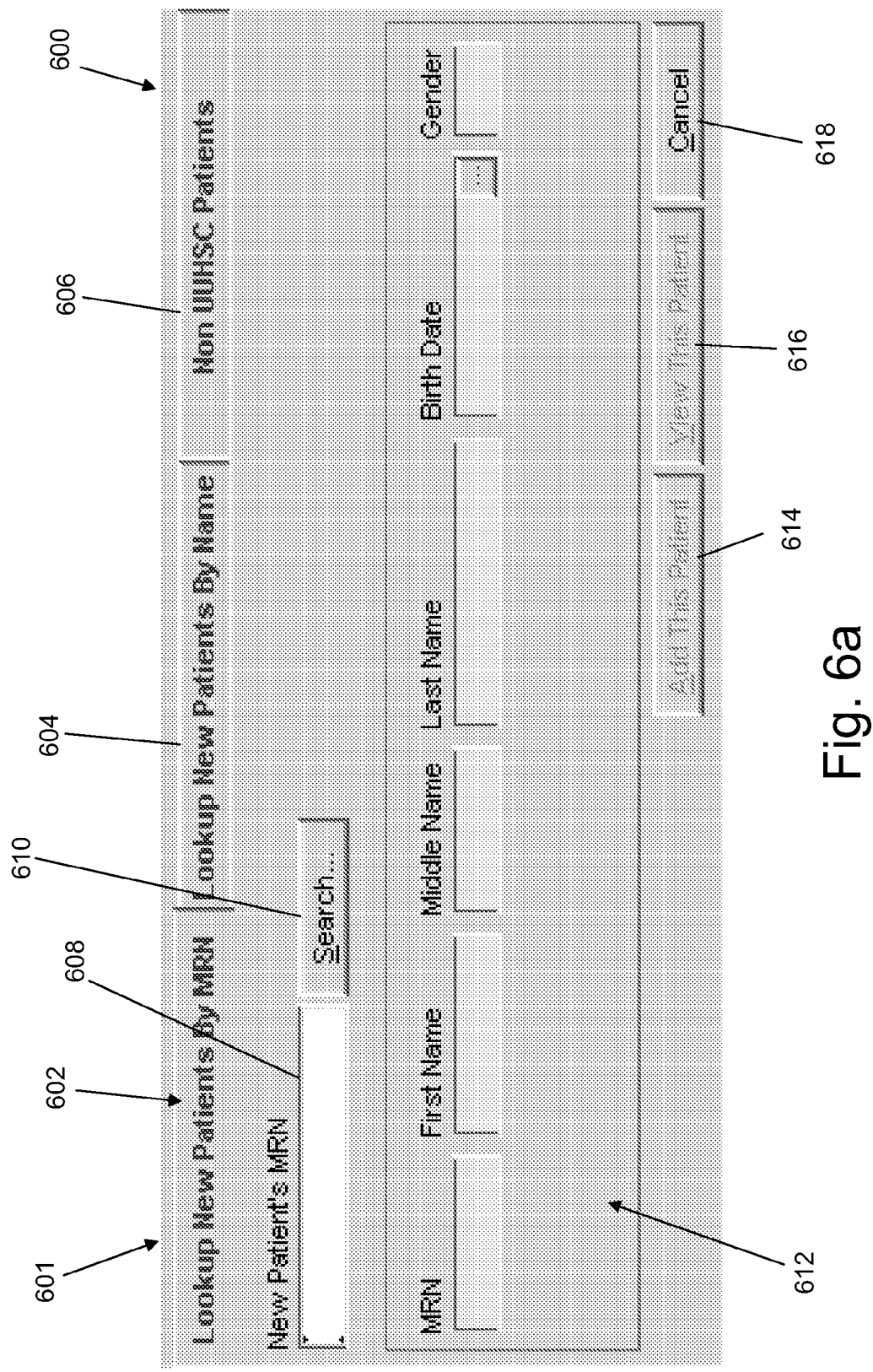
FIG. 6a depicts a new patient wizard window of the medical research application in accordance with an exemplary embodiment.

With continued reference to FIG. 3, selection of new patient wizard button 318 causes presentation of windows that walk the user through the steps of searching for and registering a patient of interest to the cancer group. With reference to FIG. 6a, a new patient wizard window 600 allows the user to specify search criteria for identifying a patient from records database 124. New patient wizard window 600 may include a plurality of tabs 601, an add patient button 614, a view patient button 616, and a cancel button 618. The plurality of tabs 601 may include a lookup by MRN tab 602, a lookup by name tab 604, and a non-clinic patient tab 606. Lookup by MRN tab 602 may include an MRN text box 608, a search button 610, and a results section 612. The user may enter a MRN into MRN text box 608 and select search button 610 using input interface 106. Records database 124 is searched using the entered MRN and matching information is returned to the user in results section 612.

Results section 612 may include patient identification information such as the MRN, the first name, the middle name, the last name, the birth date, and the gender. If the correct patient is identified in results section 612, the patient may be added for use clinically or for research/study using medical research application 116 by selecting add patient button 614. For further verification, additional patient information may be presented by selecting view patient button 616. Execution of the new patient wizard may be cancelled by selecting cancel button 618. Lookup by name tab 604 allows the user to identify a patient by entering name information instead of a MRN. Using non-clinic patient tab 606, an application programming interface is presented to the user to add a patient to database 122 whose medical information is not stored in records database 124.

With continued reference to FIG. 3, administration button 320, reporting button 324, and/or ad hoc reporting button 326 may be selectable or not based on the user's privileges. Selection of administration button 320 causes presentation of windows which allow the user to manage user and group access privileges for medical research system 100. Selection of reporting button 324 and/or ad hoc reporting button 326 causes presentation of windows which allow the user to generate output data from medical research application 116.

Figure 6B:
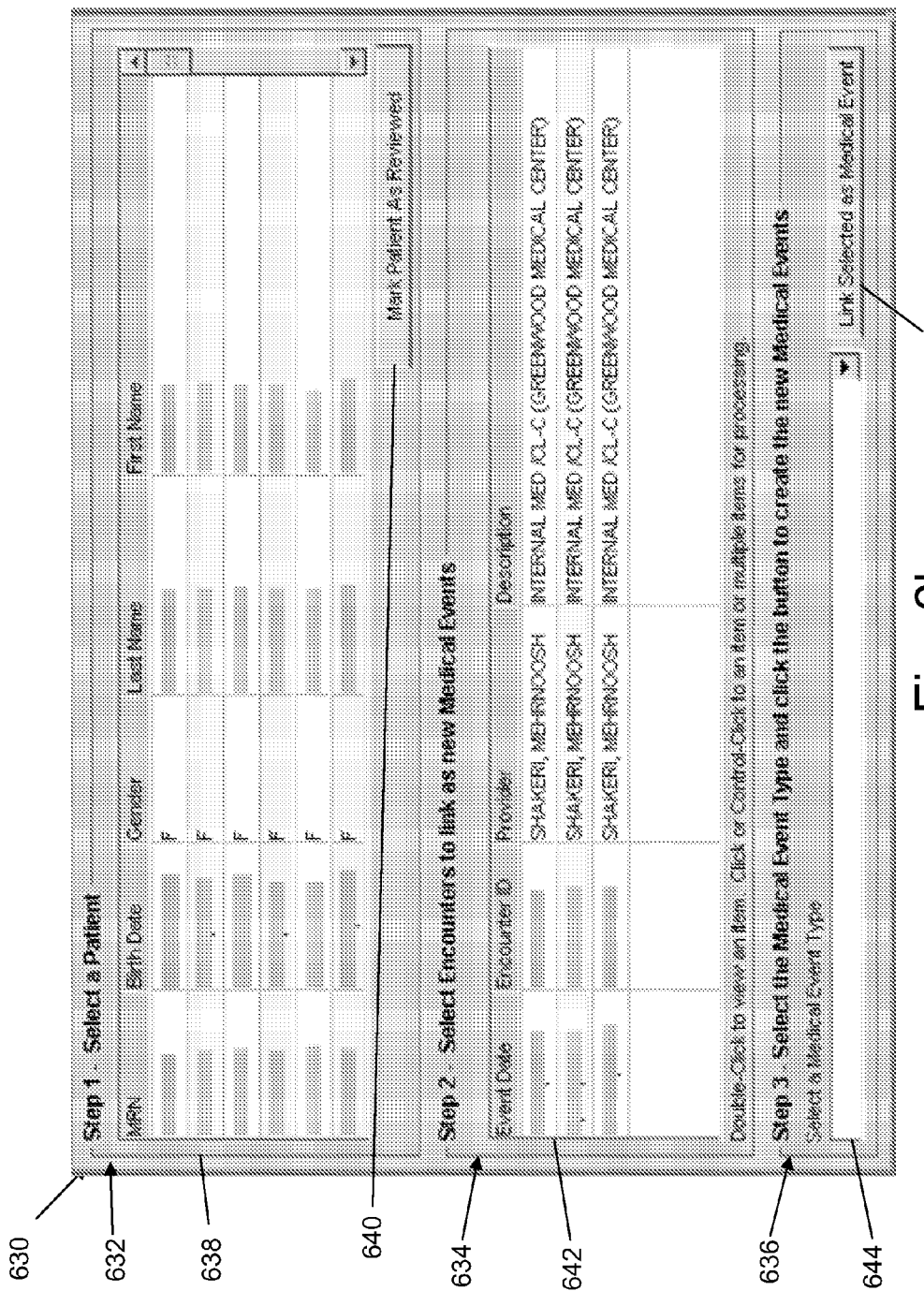
FIG. 6b depicts a patient update window of the medical research application in accordance with an exemplary embodiment.

Selection of encounter review button 322 causes presentation of windows which support the efficient entry of additional data for a patient that results from subsequent medical encounters. With reference to FIG. 6b, a patient update window 630 is organized into three sections associated with updating a patient's medical information. In accordance with the exemplary embodiment of FIG. 6b, patient update window 630 may include a patient selection section 632, a patient encounter selection section 634, and a medical event selection section 636. Patient selection section 632 may include a patient table 638 and a patient mark button 640. Patient table 638 may include MRN, birth date, gender, and first and last name columns for patients that have new encounter information. Selection of a patient in patient table 638 followed by selection of patient mark button 640 marks the selected patient as having been reviewed so the user can focus on new encounters that have not been reviewed. Selection of a patient in patient table 638 causes presentation of encounter information in patient encounter selection section 634 which includes an encounter table 642. Encounter table 642 may include event date, encounter identifier, provider, and description columns. The encounter information may be received from database 122. The user can view additional information associated with the encounter, for example, by double-clicking on an encounter listed in encounter table 642.

Medical event selection section 636 may include a medical event selector 644 and a medical event link button 646. If the user decides to enter a new medical event to capture the encounter information for one or more encounters listed in encounter table 642, the user selects an appropriate medical event using medical event selector 644 and selects medical event link button 646 to store the medical event. In an exemplary embodiment, the event start date and the type of event are filled in and stored automatically. Subsequently, when the user views a patient's detailed record, the new medical event is highlighted, for example using color such as green to alert the user that additional information associated with the medical event may be entered.

Figure 7A:
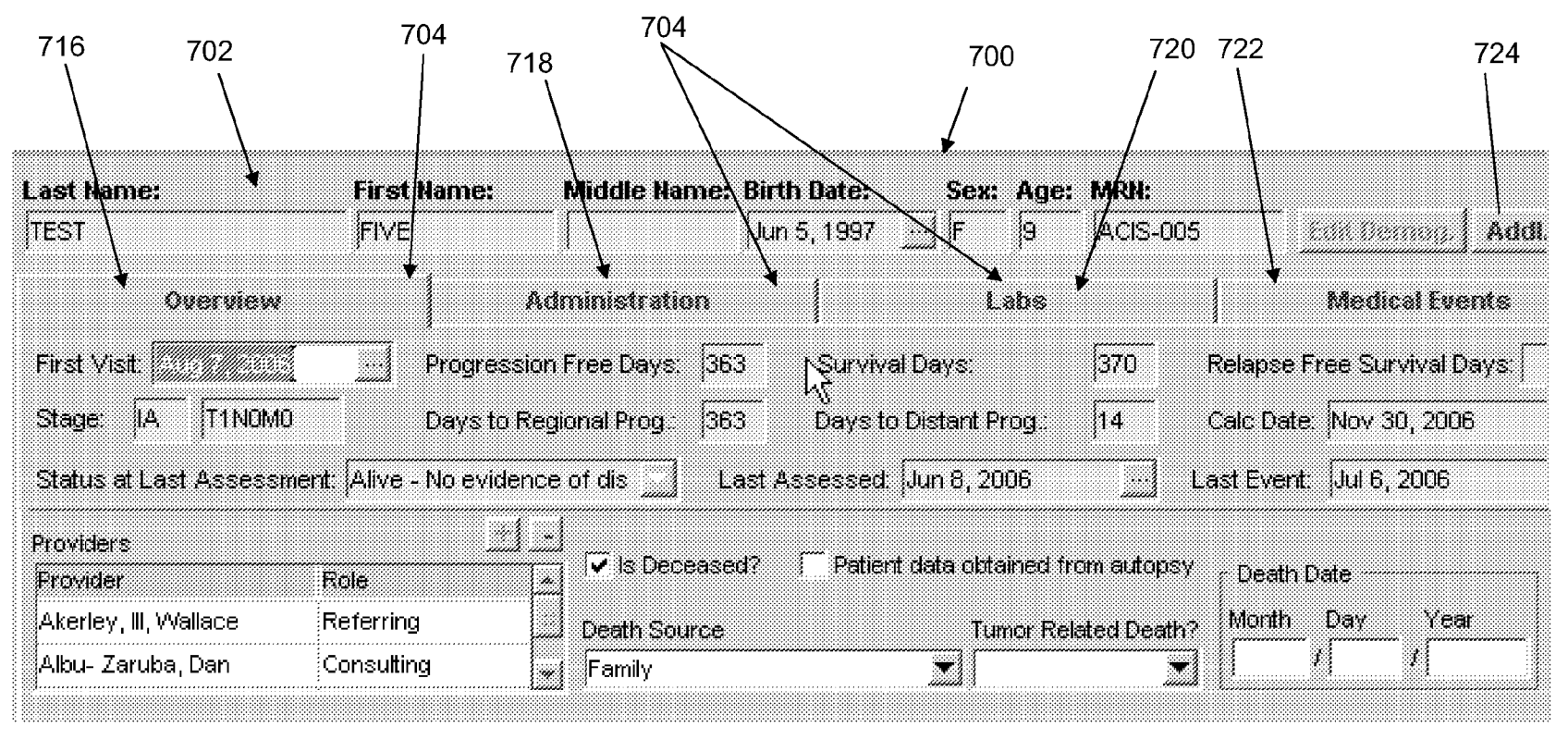
Figure 7B:
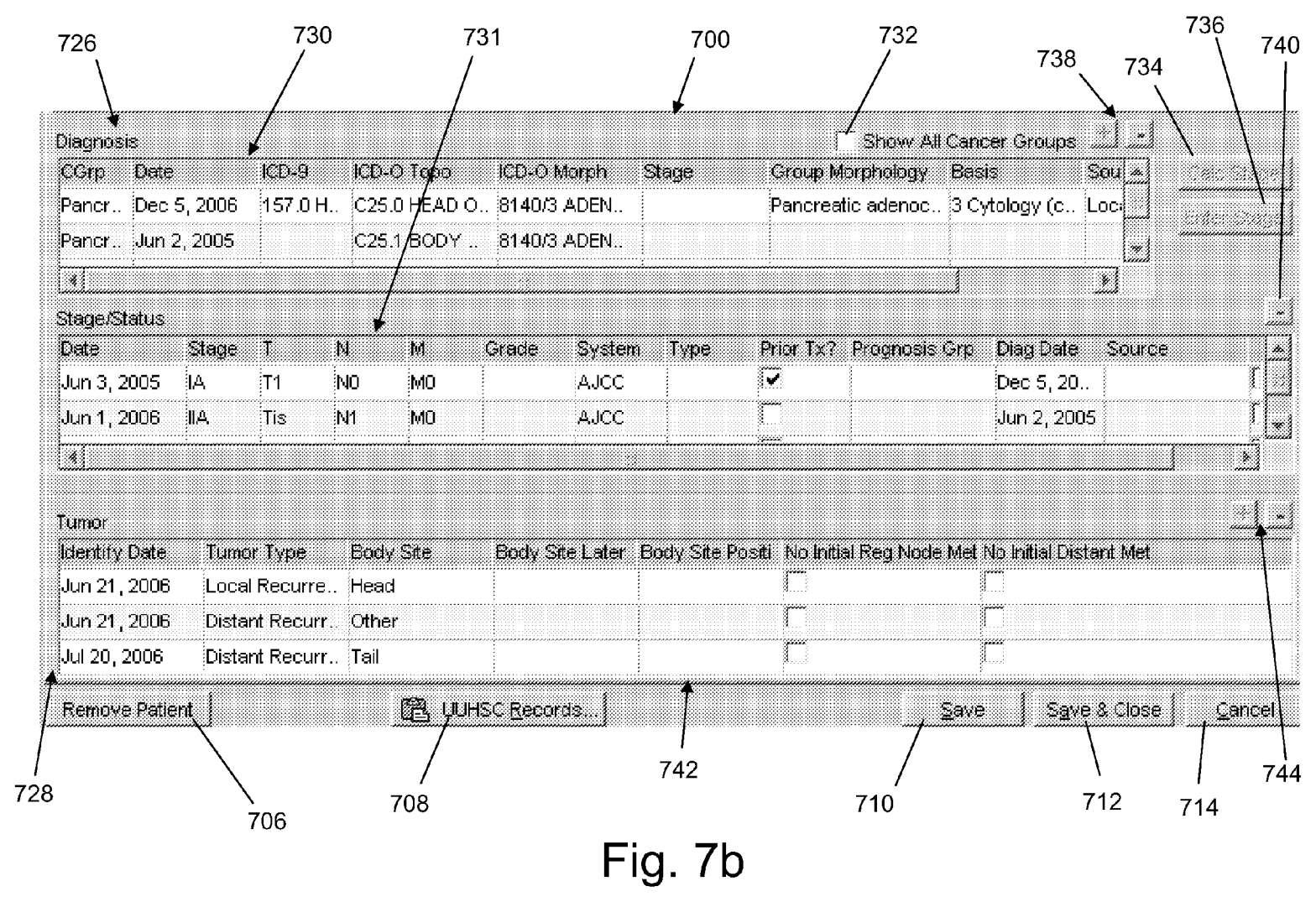
Figure 7C:
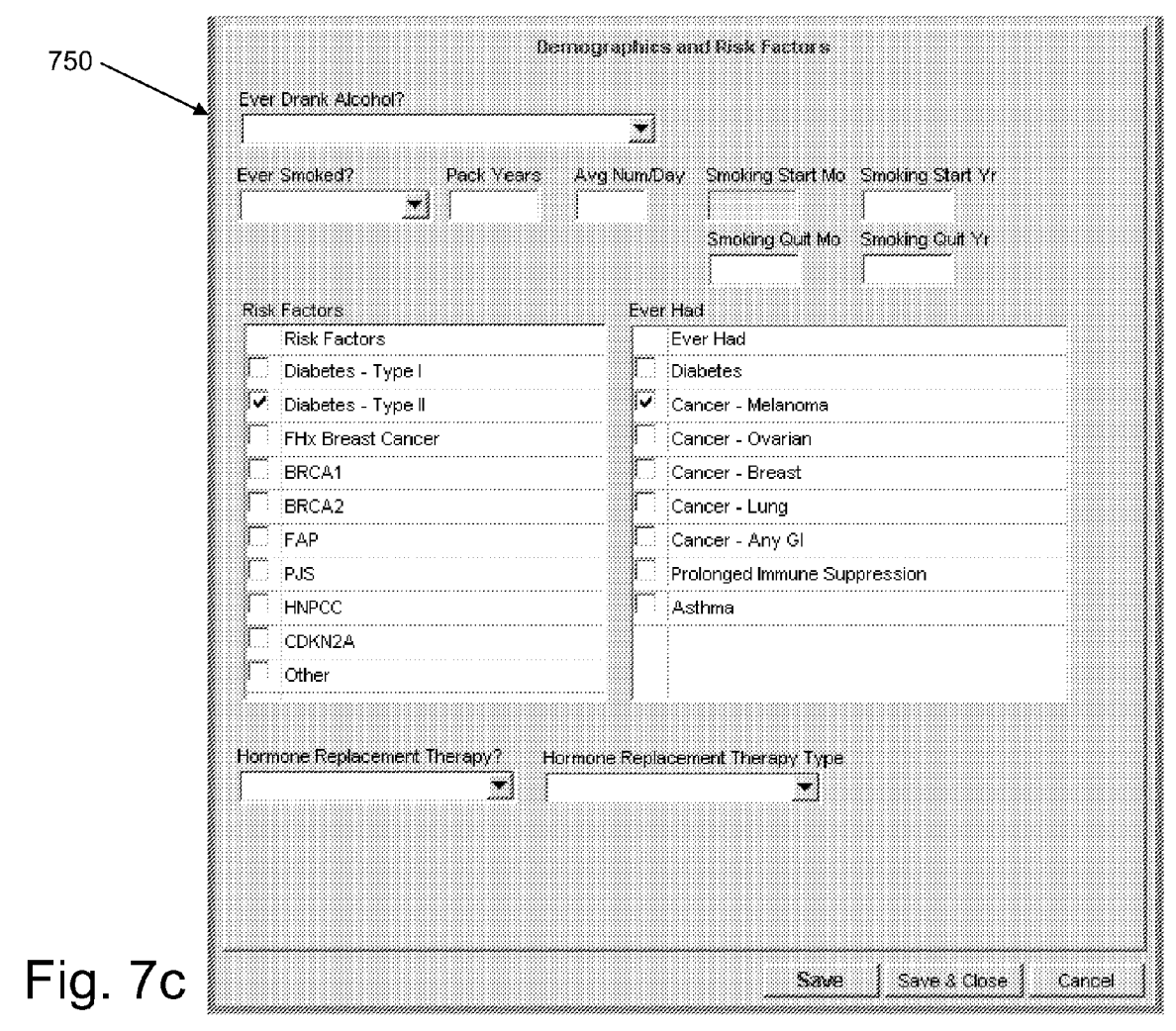

With reference to FIGS. 7a and 7b, a patient information window 700 allows the user to review a selected patient. For example, patient information window 700 may be presented to the user on display 104 using browser application 116 after a patient look-up process, a patient search process, selection of view patient button 616, etc. Patient information window 700 may include information that is "grayed out" to indicate that the data is read only. Patient information window 700 may include patient demographic data 702, a plurality of tabs 704, a remove patient button 706, a records button 708, a save button 710, a save and close button 712, and a cancel button 714. Demographic data 702 may include the patient name, birth date, gender, address, phone numbers, etc. and may not be editable using medical research application 116. Additional demographic information may be entered and tracked within medical research application 116 using metabuilder application 118. The additional demographic information may include race, ethnicity, death information, providers, additional contact information, first visit date, other names or identifiers for the patient, a group-defined classification for the patient, etc. as determined by the cancer group/study. To access the additional demographic information, the user may select an "Additional Patient Data" button 724, which causes presentation of an additional patient data window 750, shown with reference to FIG. 7c. In the exemplary embodiment of FIG. 7c, additional patient data window 750 includes risk factors related to alcohol, smoking, prior medical conditions, and use of hormone replacement therapy. Of course, additional patient data window 750 may include a wide variety of parameters, for example, based on the research study involved.

With continuing reference to FIG. 7a, the plurality of tabs 704 may include an overview tab 716, an administration tab 718, a labs tab 720, a medical events tab 722, etc. Overview tab 716 may include basic identifying information and information that summarizes the state of the disease and the disease progression. Administration tab 718 may include information necessary to administer the patient and study enrollments, which is not part of the key summary information. Labs tab 720 may include study and test result information for the cancer group. Medical events tab 722 may include event information for the cancer group. Selection of remove patient button 706 removes the presented patient from use clinically or in a research/study using medical research application 116. Selection of records button 708 accesses additional information related to the patient from records database 124 including pathology reports, lab results, radiology reports, general documents including textual pathology reports, any additional encounters, etc. Selection of save button 710 saves the currently entered/selected data for the patient and patient information window 700 continues to be presented to the user. Selection of save and close button 712 saves the currently entered/selected data for the patient and closes patient information window 700. Selection of cancel button 714 removes any currently entered/selected data for the patient and closes patient information window 700.

Overview tab 716 may include information that summarizes the state of the disease and the disease progression, a diagnosis section 726, and a tumor section 728. Diagnosis section 726 may include a diagnosis grid 730, a stage grid 731, a show all checkbox 732, a calculate stage button 734, an enter stage button 736, first add/remove buttons 738, and a remove button 740. Diagnosis grid 730 may include diagnoses of interest to the cancer group and/or entered by the cancer group. Associated with each diagnosis included in diagnosis grid 730 may be the cancer group, the date, ICD-9 or ICD-O codes, cancer-group specific morphology and comments, patient age at diagnosis (calculated if possible), the source of the diagnosis, the non-microscopic or microscopic basis for the diagnosis, etc. Diagnosis grid 730 can be expanded to show all known diagnoses for the patient by selecting show all checkbox 732. After a cancer diagnosis has been entered calculate stage button 734 and enter stage button 736 may be activated. If sufficient pathologic and/or clinical information is available to stage a cancer patient, calculate stage button 734 may be selected. Alternatively, enter stage button 736 can be selected to enter a stage that is not calculated. Selection of first add/remove buttons 738 adds/removes diagnoses from diagnosis grid 730. Selection of remove button 740 removes erroneous stages from stage grid 731. Tumor section 728 may include a tumor grid 742 and second add/remove buttons 744. Tumor grid 742 may include tumor information for each tumor such as an identification date, a tumor type, body site information, etc. Selection of second add/remove buttons 744 adds/removes diagnoses from tumor grid 742.

Figure 8:
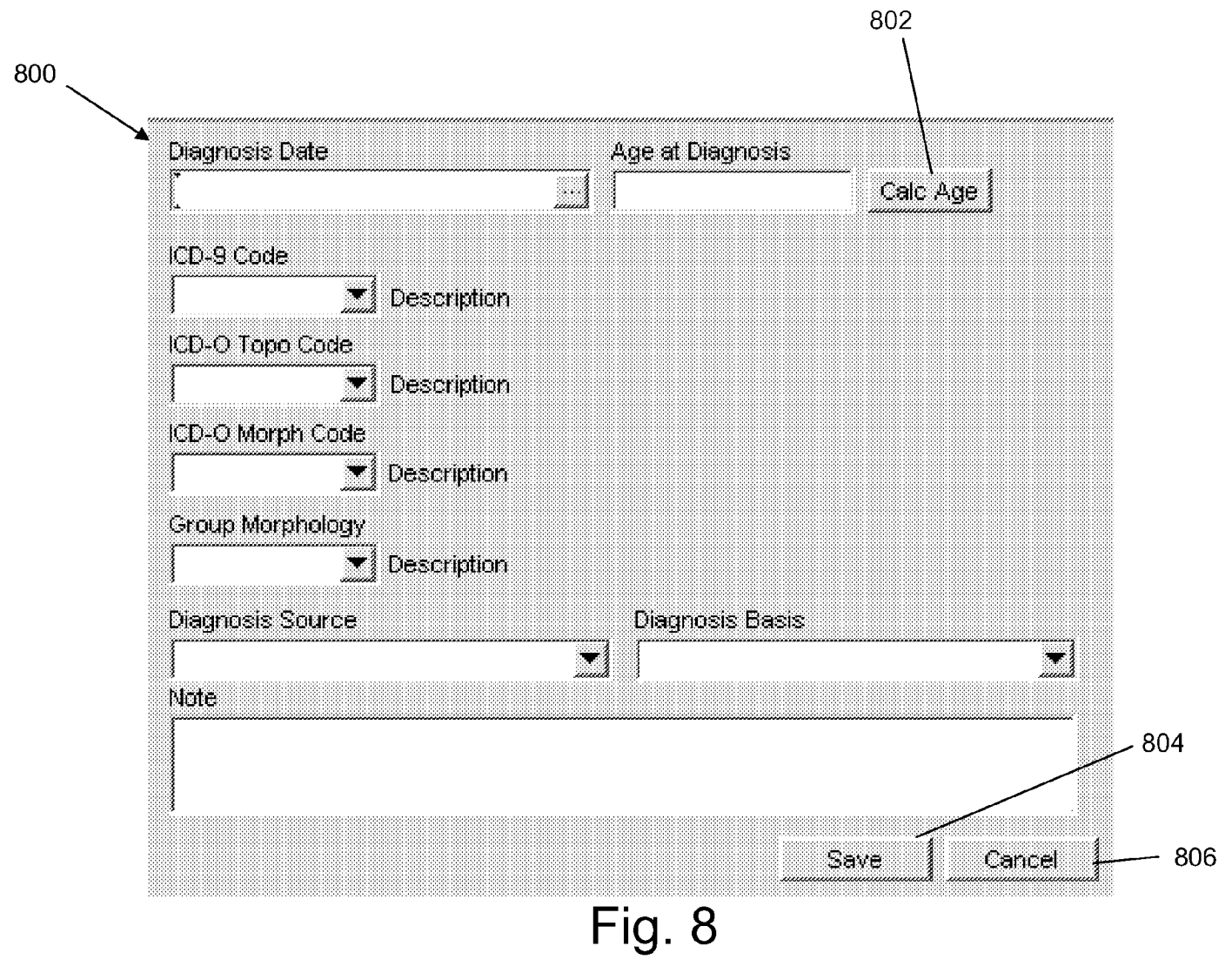

With reference to FIG. 8, a diagnosis detail window 800 allows the user to add a diagnosis to diagnosis grid 730 or to edit an existing diagnosis in diagnosis grid 730. Diagnosis detail window 800 allows entry/edit of a diagnosis date, an ICD-9 code, an ICD-O topography code, an ICD-O morphology code, a group morphology code, a diagnosis source, a diagnosis basis, and diagnosis notes. After entry of the diagnosis date, an age at diagnosis can be automatically calculated using a calculate age button 802. If the diagnosis date cannot be determined from the available information, the age can be directly entered in diagnosis detail window 800. Selection of a save button 804 saves the entered data into diagnosis grid 730. Selection of a cancel button 806 cancels entry of the entered data into diagnosis grid 730.

Figure 9:
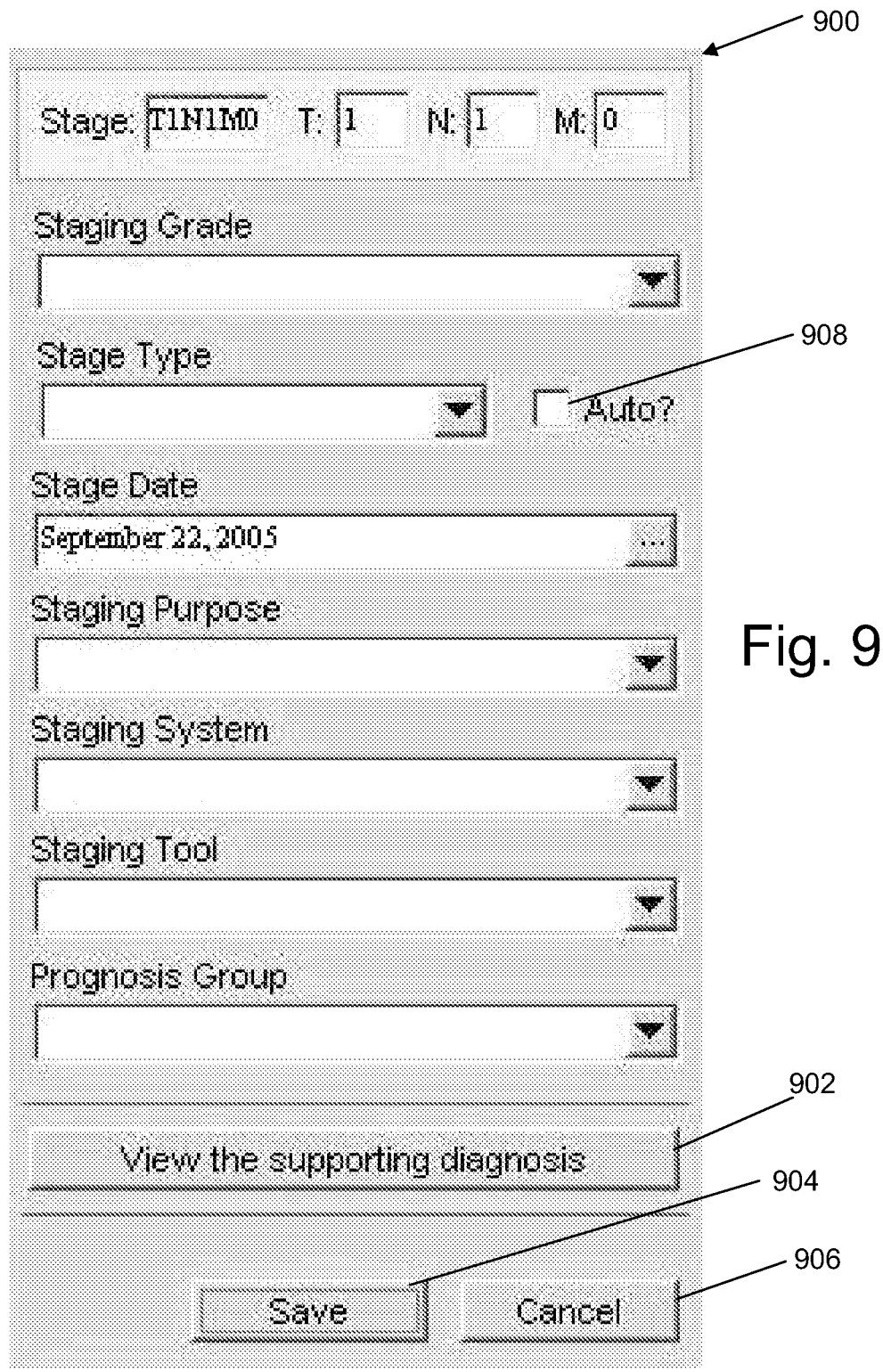
FIG. 9 depicts a staging status detail window of the medical research application in accordance with an exemplary embodiment.

With reference to FIG. 9, a stage detail window 900 allows the user to add a stage to stage grid 731 or to edit an existing stage in stage grid 731 after user selection of calculate stage button 734 or enter stage button 736 shown with reference to FIG. 7b. The stage history tracks stage entries for the patient including TNM status and grade, stage code, date, the staging system and version, the purpose for the stage entry such as initial stage, status update, restage, or trial qualification, etc. A stage entry is associated with a particular diagnosis being staged. Some cancers do not use traditional staging to determine prognosis, but rather group patients based on a variety of factors in order to determine prognosis. A prognosis group field allows entry of specialized grouping codes for these cancers. Selection of a view diagnosis button 902 allows the user to view the associated diagnosis. Selection of a save button 904 saves the entered data into stage grid 731. Selection of a cancel button 906 cancels entry of the entered data into stage grid 731.

A stage entry in the stage history represents an overall patient staging related to the diagnosis taking into account all of the information, tests, and imaging results available for the patient at that time, as opposed to a single pathologic staging. If the stage is being calculated automatically, stage detail window 900 is presented with the staging information filled in by the calculator. If the information returned by the calculator needs to be corrected due to inaccuracy or incompleteness, the controls on stage detail window 900 are editable. Editing of the stage manually results in an auto checkbox 908 becoming unchecked. If the stage is being manually entered, stage detail window 900 is presented without the staging information filled in. The user fills in the desired stage entries. From the stage history TNM status entries for a cancer group, the system may calculate and store cancer progression related information. Cancer progression related information may include initial TNM status, dates of regional and distant progression, days to regional and distant progression, progression free days (until death, progression, or last known alive date), survival days (until death or last known alive date), and relapse free survival days (until death, relapse, or last known alive date).

Figure 10:
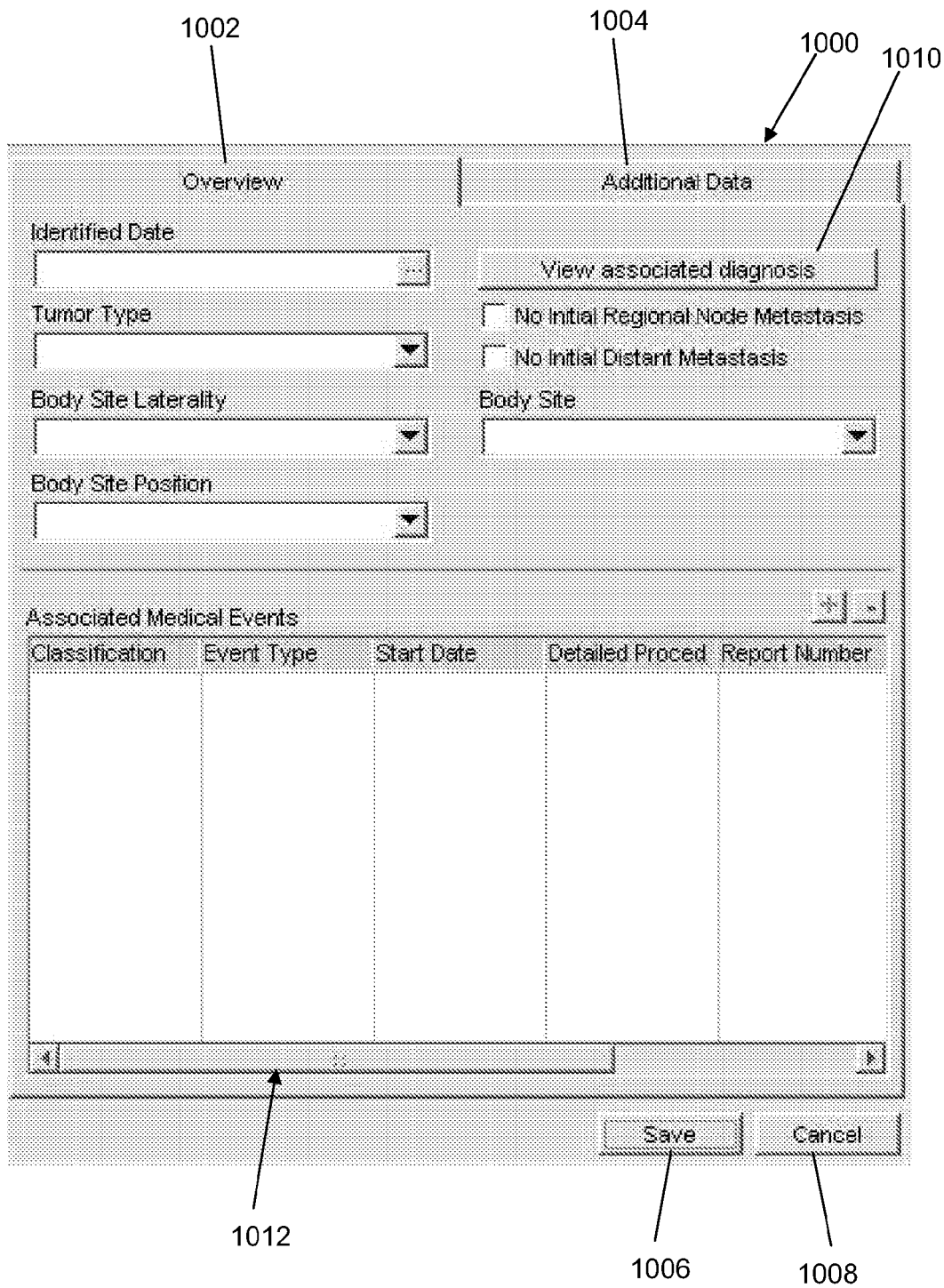
FIG. 10 depicts a first tumor detail window of the medical research application in accordance with an exemplary embodiment.

With reference to FIG. 10, a tumor detail window 1000 allows the user to add a tumor to tumor grid 728 or to edit an existing tumor in tumor grid 728. In the exemplary embodiment of FIG. 10, tumor detail window 1000 includes an overview tab 1002 and an additional data tab 1004. Tumor entries track specific tumors along with tumor characteristics not ordinarily part of the diagnosis or that may be more conveniently summarized relative to the tumor. Overview tab 1002 may include the date the tumor was identified, the type (primary tumor, local, or distant recurrence), body site details (such as specific body location in the case of melanoma or sarcoma, or more detailed placement within the organ for other cancers), laterality and anterior/posterior position, and whether regional or distant metastasis was initially detected. The user may view attributes associated with a specific diagnosis in the diagnosis history linked to the tumor by selecting view diagnosis button 1010. If no diagnosis is associated with the tumor, the existing diagnoses for the patient may be reviewed.

In staging the patient, the status of detection of nodal and distant metastasis is important. This information may eventually become available and be collected during pathologic investigation of tumor samples. However, in cases where clinical investigation has determined that no nodal or distant metastasis has occurred, this may be explicitly recorded with checkboxes included under overview tab 1002. The explicit recording of nodal and distant metastasis status assists the staging calculator in selecting the correct stage. The tumor may also link to medical events (such as tumor biopsy) which may contain more detailed information on specific procedures and diagnostics performed for the tumor, including pathology report data. The medical events may be added to or removed from a medical event grid 1012. Selection of a save button 1006 saves the entered data into tumor grid 728. Selection of a cancel button 1008 cancels entry of the entered data into tumor grid 728.

Figure 11:
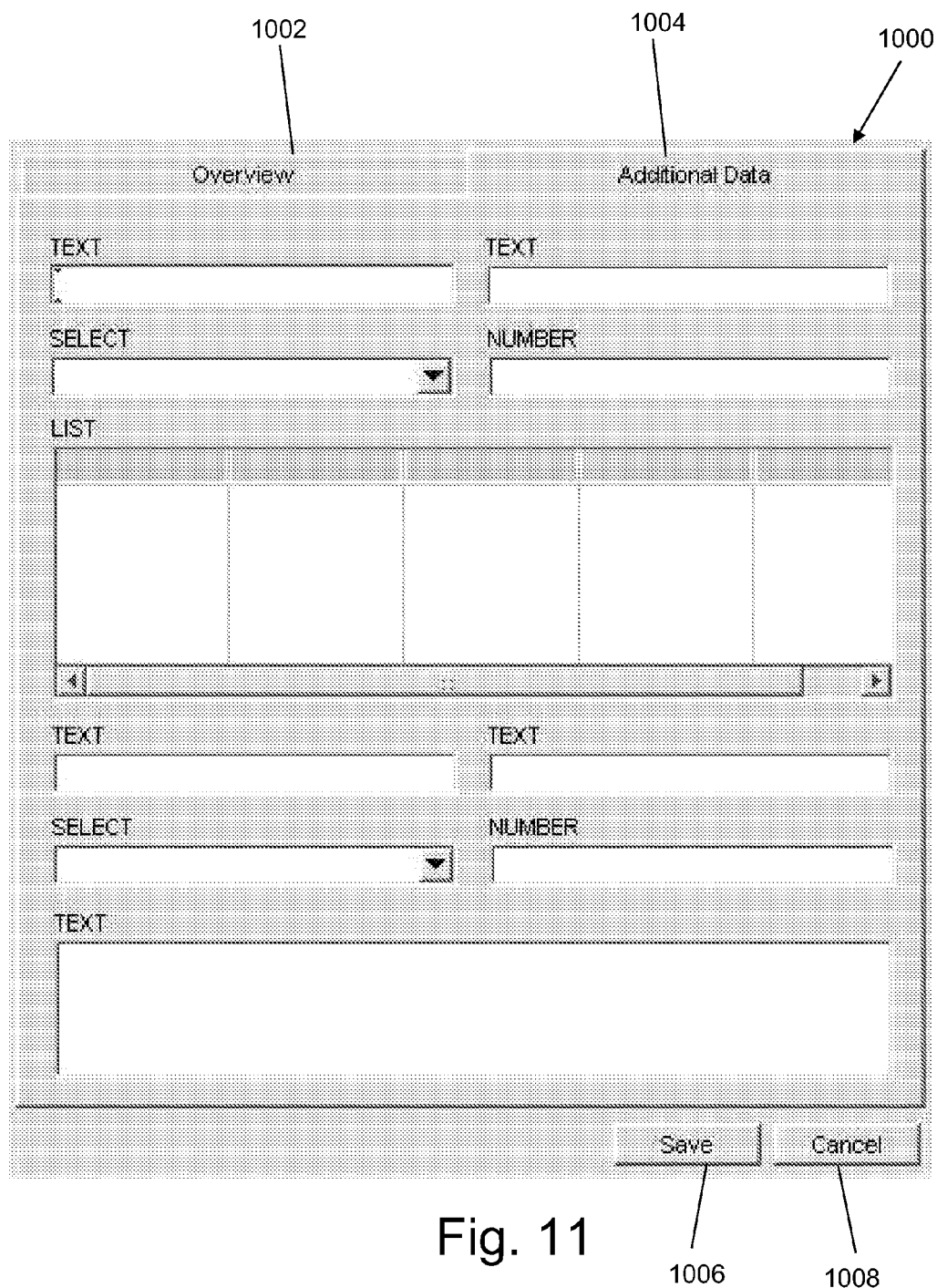
FIG. 11 depicts a second tumor detail window of the medical research application in accordance with an exemplary embodiment.

With reference to FIG. 11, additional data tab 1004 may be presented if the cancer group has specified additional fields to be captured for each tumor. The generic controls (text, select, number, and list) may be replaced with cancer group specified fields. For example, the additional fields are defined using metabuilder application 120 discussed with more detail with reference to FIGS. 28-32.

Figure 12:
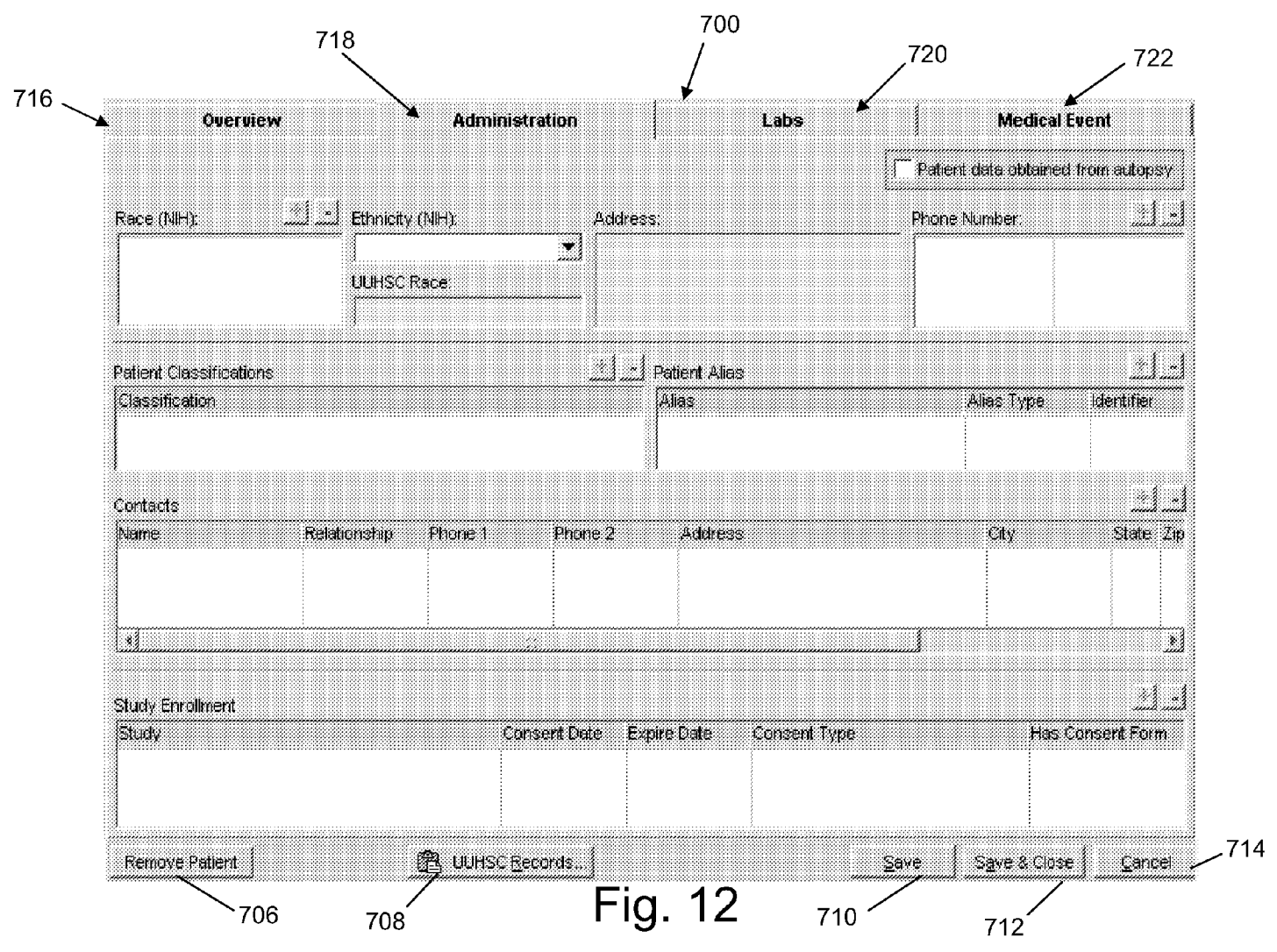

With reference to FIG. 12, administration tab 718 presents extended demographic, contact, classification, and study enrollment information. Studies may be defined for the cancer group. Part of the definition of a study is the consent types to which a patient may consent to participate in the study. When a patient has consented, users with write permission to the study may enroll the patient and enter the consent information, including the date of consent, the type of consent, the date the consent will expire, etc. Consent forms are added to a patient for a particular study by selecting a consent type from a list predefined for the study. The expiration of the consent is automatically calculated from the expiration period predefined for that consent type for the study. A scanned image of the consent form may be uploaded and linked to the enrollment. Patient information related to race, ethnicity may be entered.

Figure 13:
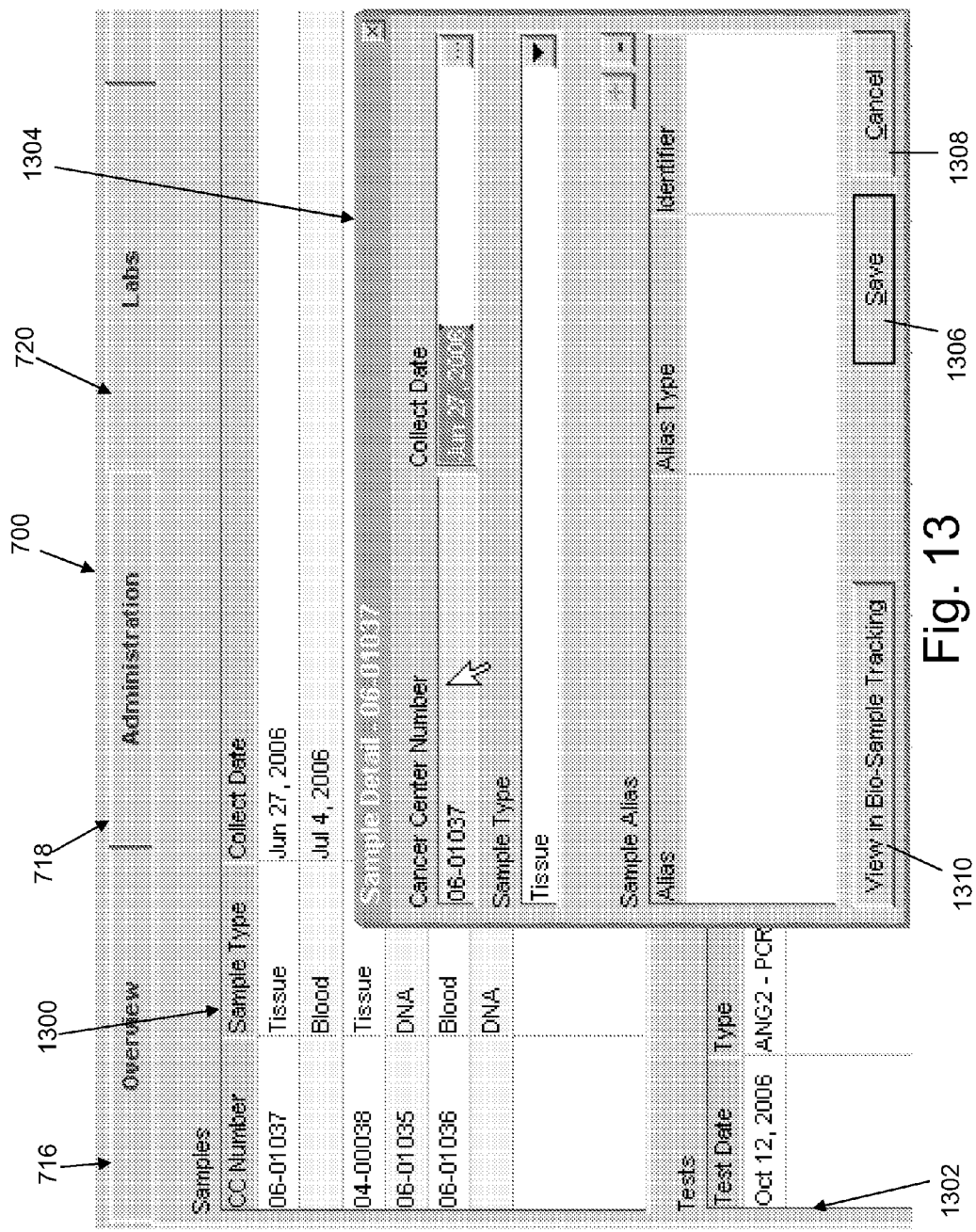
FIG. 13 depicts an labs tab of the patient detail window of FIGS. 7a and 7b in accordance with an exemplary embodiment.

With reference to FIG. 13, selection of labs tab 720 presents sample and test result information for the patient. Labs tab 720 may include a sample grid 1300 and a test grid 1302. The samples and tests included in sample grid 1300 and in test grid 1302 may be cancer group specific. Samples may be added for the cancer group, and they may also be linked to existing samples in database 122 or in a separate biosample tracking (BST) database at computing device 103 or at another computing device accessible using a network. Thus, database 122 may include the BST database. Alternatively, the BST database may be separate from database 122. Sample grid 1300 includes a list of samples collected for the patient that the cancer group chooses to track. Sample grid 1300 may include a collection date, a sample type, and an identifier by which the sample is tracked.

A sample detail window 1304, presented using medical research application 116, is shown in accordance with an exemplary embodiment. Sample detail window 1304 may be presented after double-clicking on a sample in sample grid 1300 or using other methods known to those skilled in the art. Selection of a save button 1306 saves any modified sample data into sample grid 1300. Selection of a cancel button 1308 cancels entry of any modified sample data into sample grid 1300. Selection of a view in BST button 1310 transfers the user to BST application 118 to view additional sample details if the sample has been linked through BST application 118. If the sample has not been linked to a sample, view in BST button 1310 is replaced with a link to BST button (not shown).

Access to biological samples, and accurate information about them, is essential to research. For example, progress on research projects may hinge on the availability of tissue samples from individuals with particular phenotypes or genotypes. BST application 118 addresses the need for researchers to find samples, to track access to samples, and to access related clinical data. Samples come into research programs through many avenues. Samples may come from a tissue acquisition and distribution facility, a laboratory, collaborative research sources, or be purchased from a vendor. Using BST application 118, the user can identify the quantity of the sample collected, the preparation method and storage location of the sample, which projects have received the sample, how much of the sample remains for use, how/if the sample was transformed into DNA, RNA, or cell lines, etc.

Figure 14:
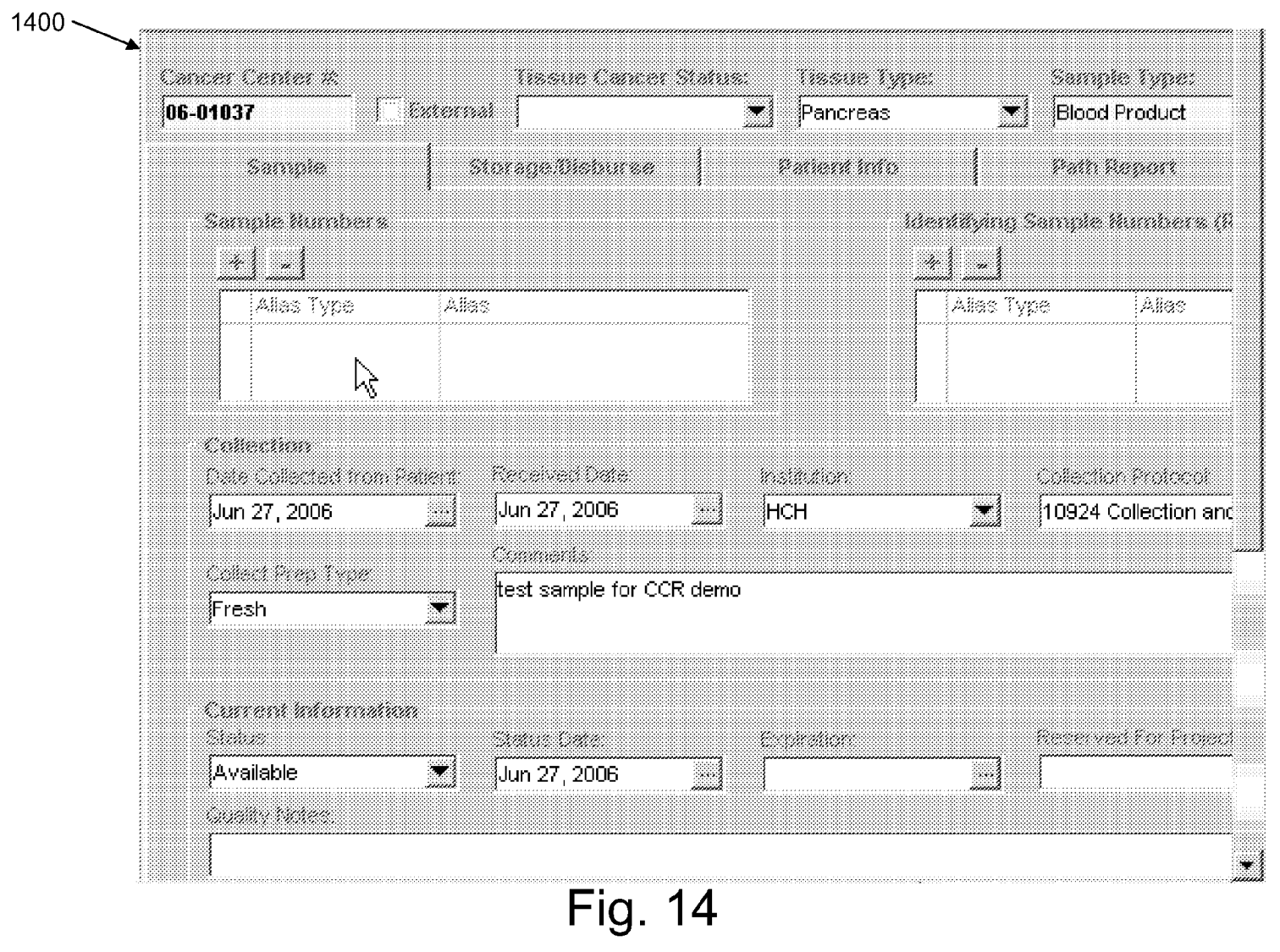

With reference to FIG. 14, a sample detail window 1400 presented using BST application 118 is shown in accordance with an exemplary embodiment, for example, after selection of view in BST button 1310. BST application 118 provides tracking of all types of samples. Sample detail window 1400 may include sample identification data, products of sample division and transformation, collection information, status information, storage/disbursement information, patient information, pathology report information associated with the sample, etc.

Figure 16:
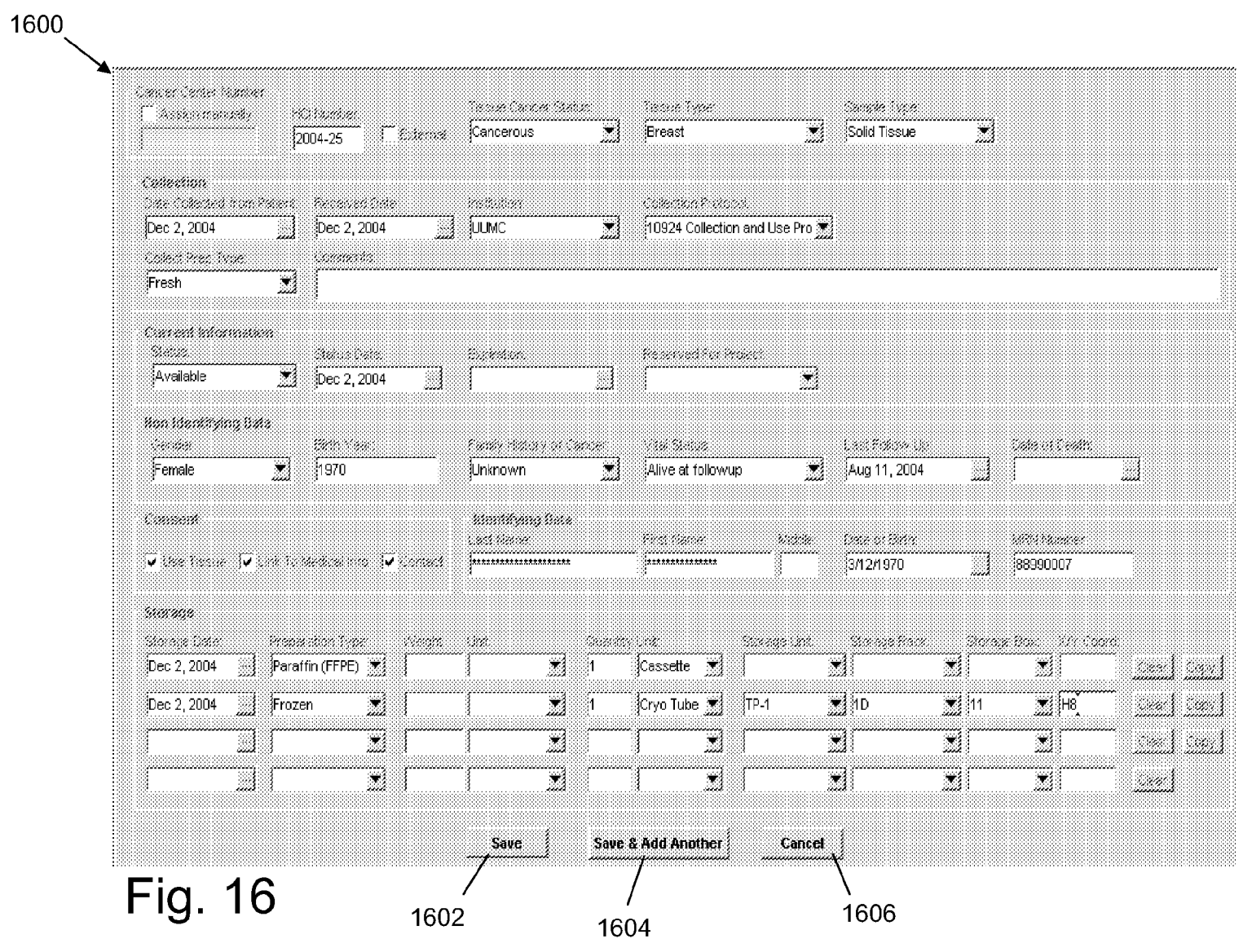

With reference to FIG. 15, a BST application main window 1500 presented using BST application 118 is shown in accordance with an exemplary embodiment. In an exemplary embodiment, BST application main window 1500 may be presented to the user in combination with sample detail window 1400 and/or other windows for presentation of sample information to the user. The user may enter search criteria such as a sample identifier, a disbursed project selector, a tissue type selector and cancer status selector, a patient identifier, etc. and select a search button associated therewith to search the BST database for a sample. BST application main window 1500 may include an add sample link 1502. Selection of add sample link 1502 may cause presentation of an add sample window 1600 shown with reference to FIG. 16. Using add sample window 1600, the user may enter the collection, storage, disbursement, and related pathology data associated with a sample. Selection of a save button 1602 saves the entered data into the BST database. Selection of a save & add another button 1604 saves the entered data into the BST database and opens a new instance of add sample window 1600. Selection of a cancel button 1606 cancels entry of the entered data into the BST database and returns the user to BST application main window 1500.

Figure 17:
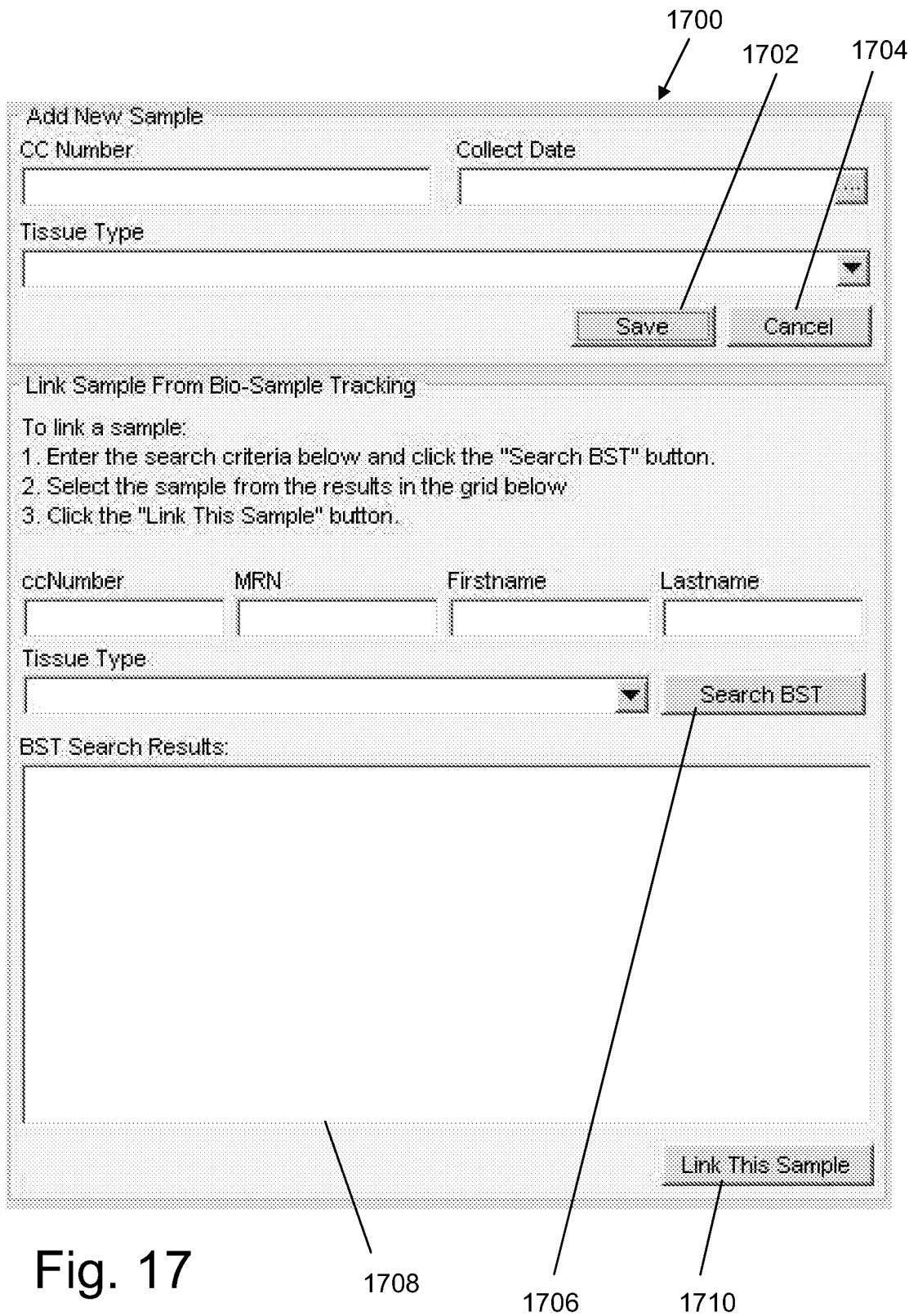
FIG. 17 depicts an add sample window of the medical research application in accordance with an exemplary embodiment.

With reference to FIG. 13, a sample can be added to sample grid 1300, for example, by user selection of a '+' button (not shown) presented in labs tab 720. Selection of the '+' button may cause presentation of add sample wizard window 1700 shown with reference to FIG. 17 in accordance with an exemplary embodiment. An unlinked sample can be created by entering/selecting the collection date, the sample type, and the sample identifier by which the sample is tracked and selecting a save button 1702. Selection of a cancel button 1704 cancels entry of the sample into sample grid 1300. Alternatively, a sample may be linked to BST application 118 using add sample wizard window 1700. The user may search for the sample in the BST database using a BST sample identifier, a MRN, a patient name, a tissue type, etc. After entering the desired search criteria, the user selects a "search BST" button 1706 to locate the sample in the BST database. Identified samples are presented in a search results window 1708. If the correct sample is identified, the user selects the sample in the search results list and selects a "link this sample" button 1710, which may cause two actions. First, the sample may be added to medical research application 116. Second, the sample may be linked using a common identifier to BST application 118. The advantage to linking to BST samples is that the sample can be viewed with its extended collection, storage, disbursement, and related pathology data from medical research application 116.

Figure 18:
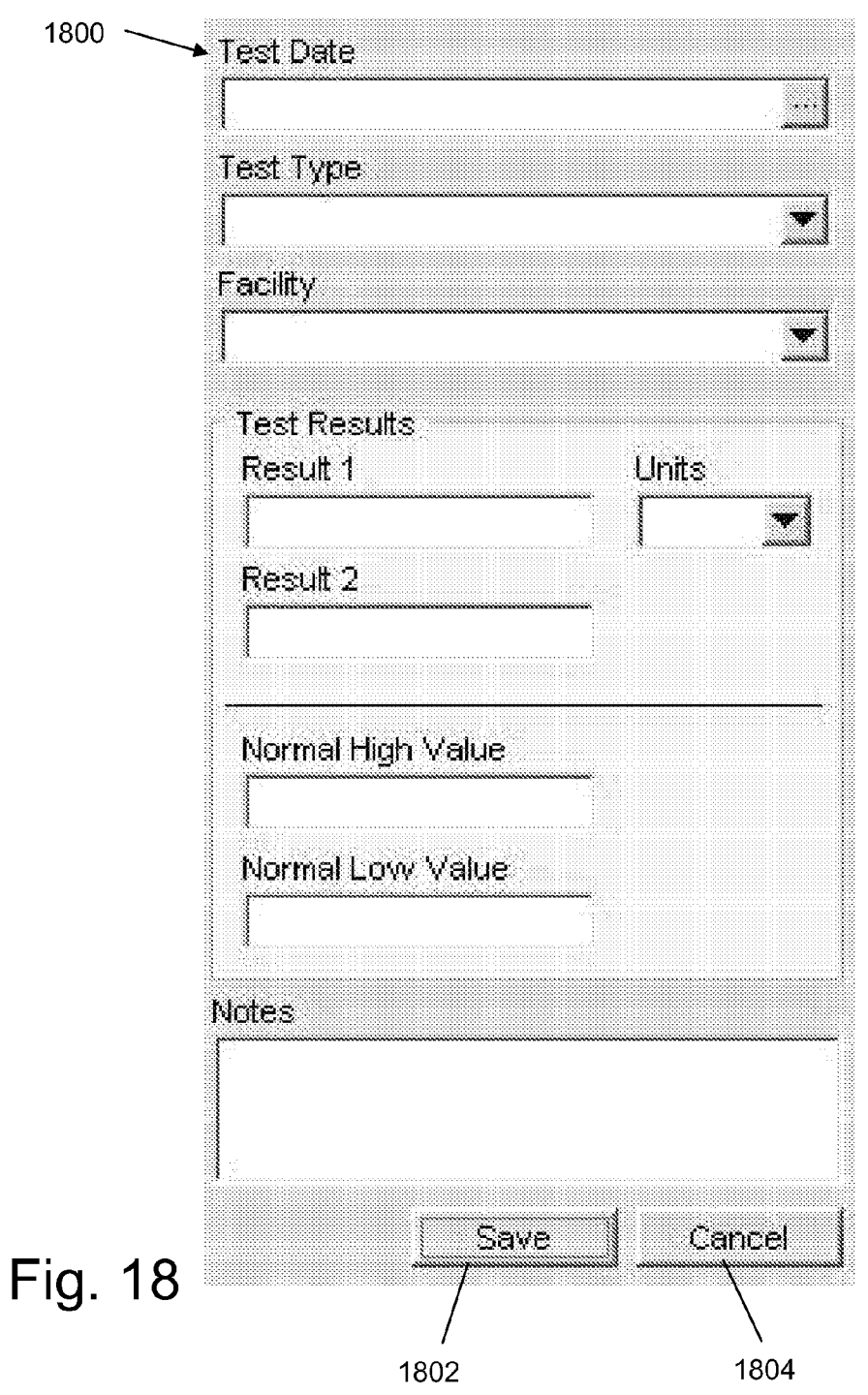

With reference to FIG. 18, a test detail window 1800, presented using medical research application 116, is shown in accordance with an exemplary embodiment. Test detail window 1800 may be presented after double-clicking on a test in test grid 1302 or using other methods as known to those skilled in the art. Test results may be entered for the patient by the cancer group. Test detail window 1800 may include a test date, a test type, a facility identifier where the test was performed, test results, and a note. The test results may include two different result values, a test units selector, a normal high value, and a normal low value for the test. The user selects the test date, the test facility, and the test type. Valid entries for the result values may be determined based on a test/result dictionary definition. Medical research application 116 may automatically define the normal high value and the normal low value based on the test type and facility. The normal high and low values can be redefined by the user if they are not accurate for the test actually performed. Selection of a save button 1802 saves the entered test data into test grid 1302. Selection of a cancel button 1804 cancels entry of the entered test data into test grid 1302.

With reference to FIG. 19, medical events tab 722 presents medical event information for the patient collected about various events and procedures that are performed for the patient. The event may represent a single procedure on a single day or may summarize a course of treatment over a period of time, such as radiation treatment or chemotherapy. Medical events tab 722 may include a medical events grid 1900. The patient may have any number of medical events, which may be listed in a chronological order. The chronological order of presentation of the medical events in medical events grid 1900 is by date based on user selection of a first radio button 1904. Viewing by date shows the activities associated with the patient longitudinally. The default presentation may be by the date. The chronological order of presentation of the medical events in medical events grid 2000, shown with reference to FIG. 20, is by tumor based on user selection of a second radio button 1906. Viewing by tumor shows those events linked to specific tumors in date order within the tumor association. The chronological order of presentation of the medical events in medical events grid 2100, shown with reference to FIG. 21, is by classification based on user selection of a third radio button 1902. Viewing by medical event classification shows only those events explicitly classified as belonging to a particular grouping. For example, medical events may be grouped by 'diagnosis' and 'treatment'. Those medical events previously associated with the 'diagnosis' classification appear under that heading, ordered by date within the classification. A medical event may be added/removed from medical events grid 1900 using add/remove buttons 1908.

Figure 22:
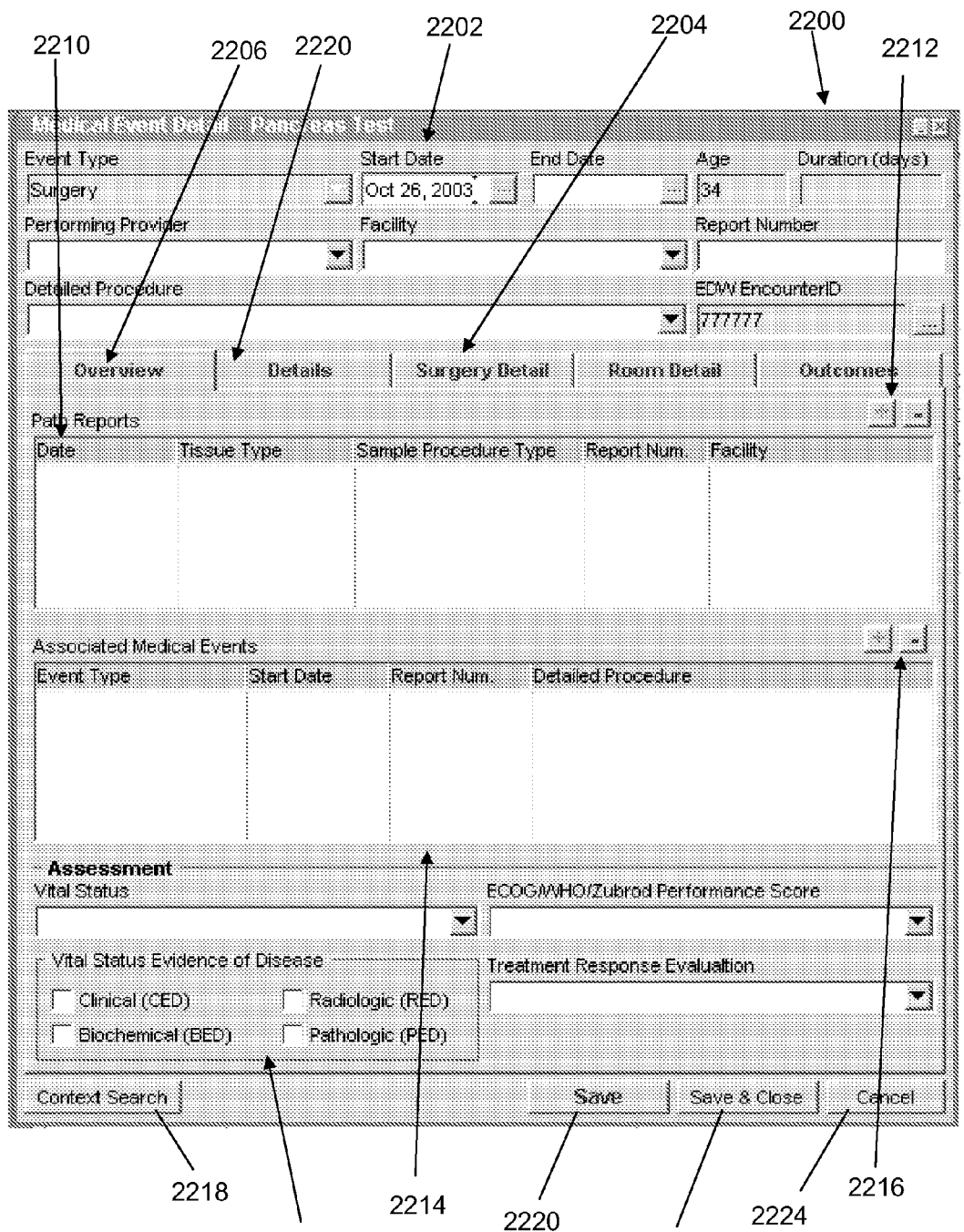
FIG. 22 depicts a medical event detail window of the medical research application in accordance with an exemplary embodiment.

With reference to FIG. 22, a medical event detail window 2200, presented using medical research application 116, is shown in accordance with an exemplary embodiment. Medical event detail window 2200 may be presented after double-clicking on a medical event in medical events grid 1900, 2000, 2100 or using other methods as known to those skilled in the art. Individual medical events may be classified into categories defined by the cancer group. For example, one cancer group may choose to create categories such as "Diagnosis", "Treatment", "Palliative Care", and "Followup". When a medical event is entered for a patient in that cancer group, it may be classified into one or more of these categories. Each cancer group may define the medical event types that it tracks, and any number of custom data fields recorded for that event type. Examples of medical event types may be "Tumor Biopsy", "Surgery", "Surgical Revision", "Initial Assessment", "Endoscopic Ultrasound", "ERCP", "Followup", etc. Some event types are commonly used for many cancers so pre-defined event types may be defined for these event types. Pre-defined event types may be Radiation Therapy, Chemotherapy, Imaging, etc.

Medical event detail window 2200 may include a first section 2202 which presents basic information shared by all medical events such as a pre-defined set of data items and links that each medical event generally has available. First section 2202 may include an event type, a start date, an end date, a performing provider, a facility, a report number and/or a report number type, a detailed procedure, etc. Medical event detail window 2200 further may include a plurality of tabs 2204 which provide additional detail associated with a medical event. Exemplary tabs of the plurality of tabs 2204 include "Overview", "Details", "Surgery Detail", "Room Detail", and "Outcomes" tabs. Additional tabs may include "Imaging" and "Radiation Therapy". An "Overview" tab 2206 may include an assessment details section 2208, a pathology report grid 2210, pathology report add/remove buttons 2212, a medical event grid 2214, medical event add/remove buttons 2216, and a context search button 2218, etc. The medical event may be classified according to the predefined groupings built for the cancer group to allow the views grouped based on classification. Selection of context search button 2218 allows the user to search textual reports stored in records database 124 by matching strings in the text with the items that need to be entered using medical event detail window 2200 and other user interface windows of medical research application 116.

Assessment details section 2208 may include a vital status selector, a performance score selector, a treatment response selector, and evidence of disease indicators. Assessment details section 2208 provides a mechanism for attaching summary level standardized measures of patient capabilities or response. These assessments are at the time of, or due to, the medical event. The vital status selector may be an overall vital and disease status. The performance score selector may be an overall performance score, such as the World Health Organization five-level scale from normal to completely disabled. The treatment response selector may be an overall measure of disease progression. The evidence of disease indicators may include clinical, biochemical, radiologic, and pathologic. Any additional types of assessment needed, especially fields to support detailed assessment systems, are built and added by the cancer group as custom data for example using meta-builder application 120 discussed with reference to FIGS. 28-32.

Selection of a save button 2220 saves the entered data into the medical events grid 1900, 2000, 2100, but leaves medical event detail window 2200 open for further editing if needed. Selection of a "save & close" button 2222 saves the entered data into the medical events grid 1900, 2000, 2100 and closes medical event detail window 2200. Selection of a cancel button 2224 cancels entry of the entered data into the medical events grid 1900, 2000, 2100 and returns the user to medical events tab 722 of patient information window 700.

Figure 23:
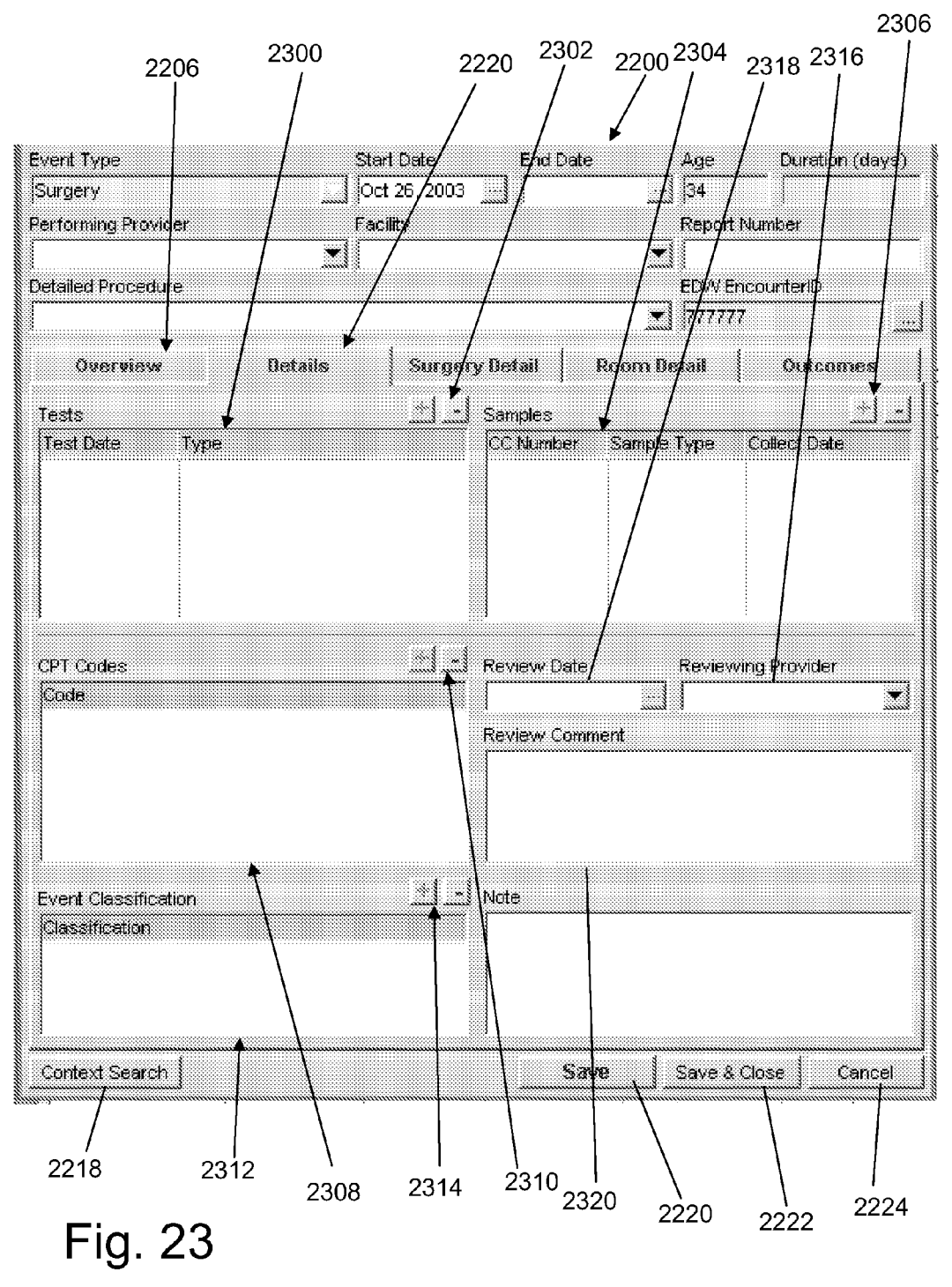

With reference to FIG. 23, a "Details" tab 2220 may include a test grid 2300, test add/remove buttons 2302, a sample grid 2304, sample add/remove buttons 2306, a current procedural terminology (CPT) code grid 2308, CPT code add/remove buttons 2310, an event classification grid 2312, classification event add/remove buttons 2314, a reviewing provider selector 2316, a review date selector 2318, and a review comment text box 2320. A CPT code is a billing code defined by the American Medical Association to describe medical services and procedures provided to a patient. Test grid 2300, test add/remove buttons 2302, sample grid 2304, and sample add/remove buttons 2306 are similar to sample grid 1300 and test grid 1302 shown with reference to FIG. 13, but are limited to those associated with the medical event.

Figure 24:
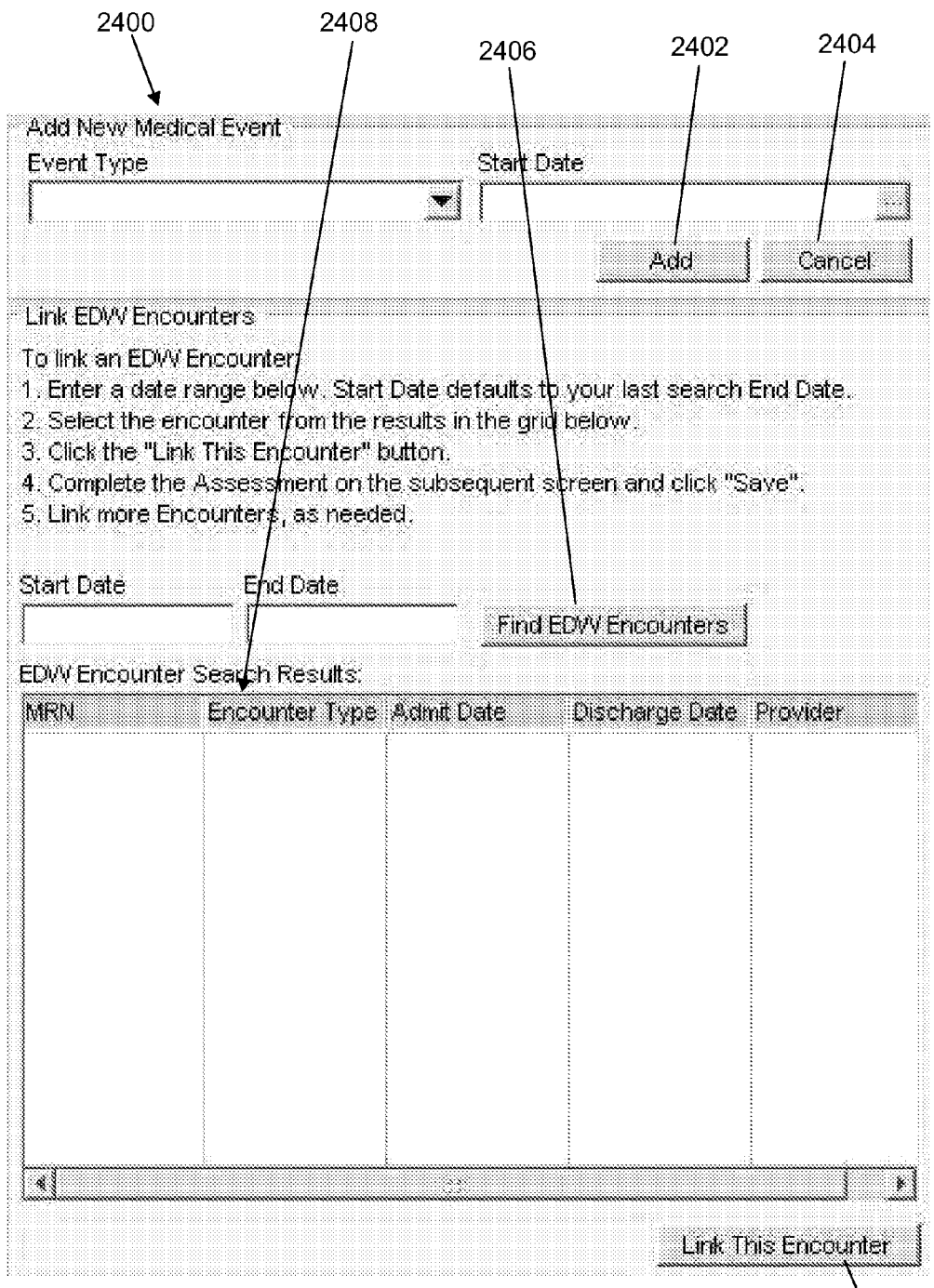
FIG. 24 depicts an add medical event window of the medical research application in accordance with an exemplary embodiment.

With reference to FIGS. 19, 20, and 21, a medical event can be added using an add button of the add/remove buttons 1908. Selection of the add button may cause presentation of an add medical event window 2400 shown with reference to FIG. 24 in accordance with an exemplary embodiment. The user may select an event type and start date. Selection of an add button 2402 creates the new medical event and opens an instance of medical event detail window 2200 for data entry. Selection of a cancel button 2404 closes add medical event window 2400 without creating a new medical event. Events with detailed clinical information, such as surgeries, biopsies, treatments, diagnostic procedures, follow up, etc. can be identified from database 122 and a link created. In an exemplary embodiment, the user enters a start date and an end date and selects a find encounter button 2406. Search results may be presented in a result grid 2408. The user identifies and selects the encounter of interest from result grid 2408 and a "link this encounter" button 2410. An instance of medical event detail window 2200 opens for additional data entry. For example, the user may enter data in assessment details section 2208 and any other desired details. Linking to the encounter provides the ability to utilize and assess the events of interest without replicating them, and to integrate the encounter with the medical events.

Figure 25:
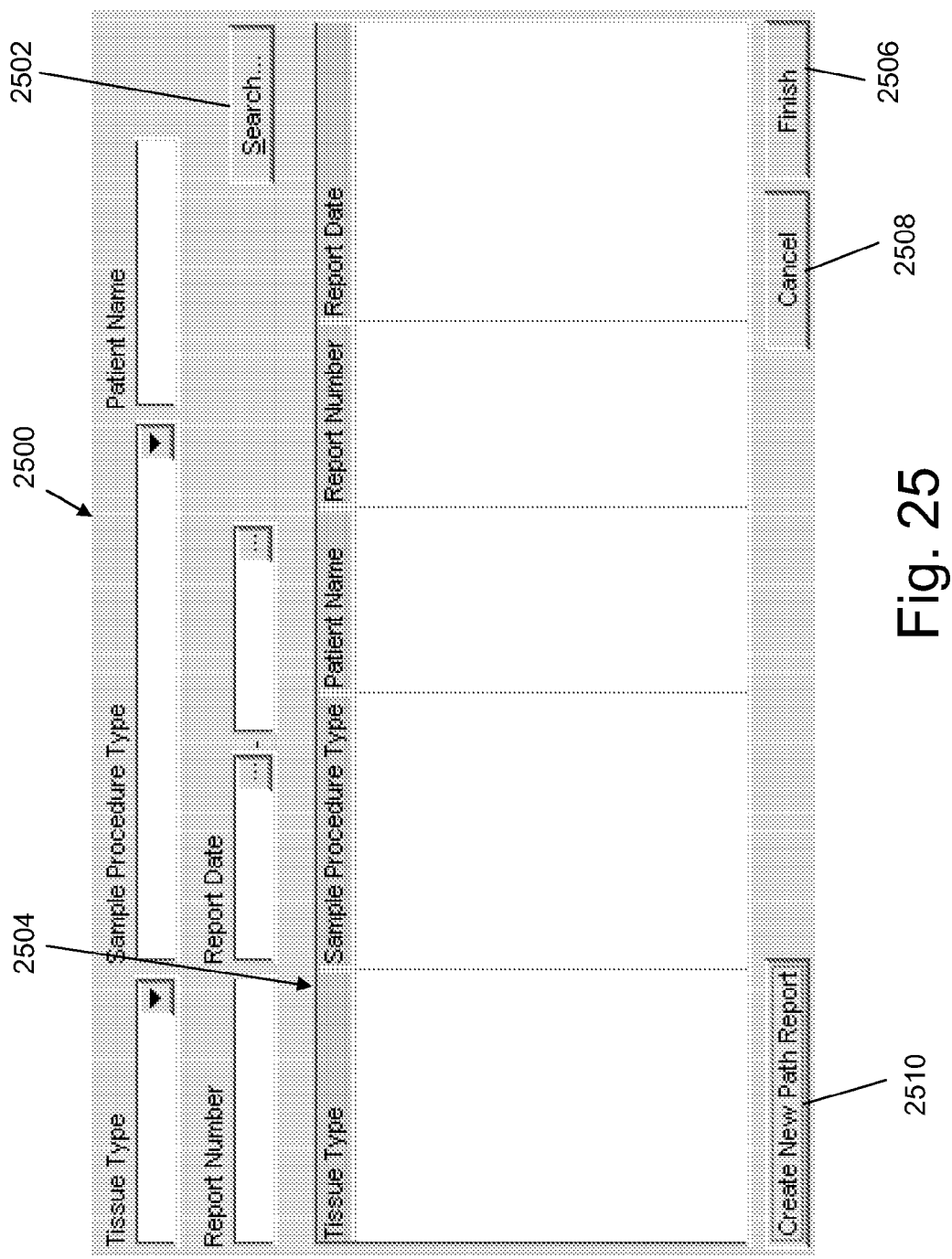
FIG. 25 depicts an add pathology report window of the medical research application in accordance with an exemplary embodiment.

A pathology report can be added using an add button of the pathology report add/remove buttons 2212 shown with reference to FIG. 22. Selection of the add button may cause presentation of an add pathology report window 2500 shown with reference to FIG. 25 in accordance with an exemplary embodiment. To enter pathology data for the medical event, an existing pathology report can be identified and a link to it created or a new pathology report can be entered by the user. In an exemplary embodiment, the user enters any or all of a tissue type, a sample procedure type, a patient name, a report number, and a report date. After entry of the search criteria, the user selects a search button 2502. Search results may be presented in a result grid 2504. The user identifies and selects the pathology report of interest from result grid 2504. To link the pathology report to pathology report grid 2210, the user selects a finish button 2506. Selection of a cancel button 2508 closes add pathology report window 2500 without creating a new pathology report.

Figure 26:
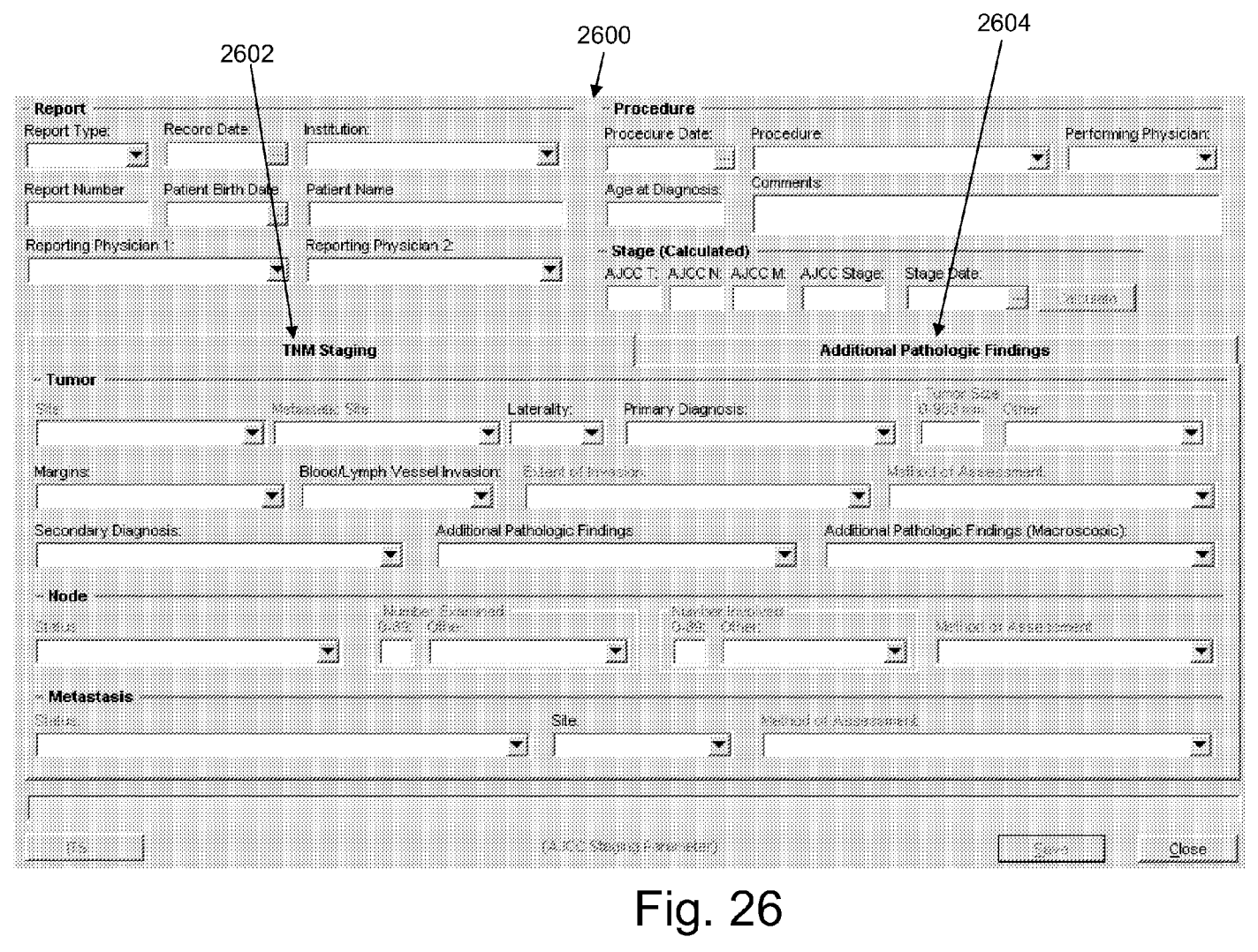

If the pathology report of interest is not found, a "Create New Pathology Report" button 2510 may be selected. Selection of button 2510 may cause presentation of a pathology report window 2600 shown with reference to FIG. 26 in accordance with an exemplary embodiment. Pathology report window 2600 may include a report type, a report date, a reporting institution, a report number, a procedure date, a tissue type, a procedure used to collect a sample, a performing and a reporting provider, a patient name and birth date, an age at the procedure, a age at diagnosis, and pathologic stage data. The stage data can be calculated or manually entered. Pathology report window 2600 may include a "TNM Staging" tab 2602 and an "Additional Pathological Findings" tab 2604. "TNM Staging" tab 2602 may include primary and metastatic tumor topography (linked to ICD-9 or ICD-O topography where possible), tumor histologic type (linked to ICD-O morphology where possible), TNM and grade status, and the system used for staging. The "Additional Pathological Findings" tab 2604 may include custom elements for pathology based on the tissue type or tissue type/sample procedure type combination added for example using metabuilder application 120 discussed with reference to FIGS. 28-32. The pathology data may be stored in database 122, in the BST database, or in a separate pathology database.

Figure 28:
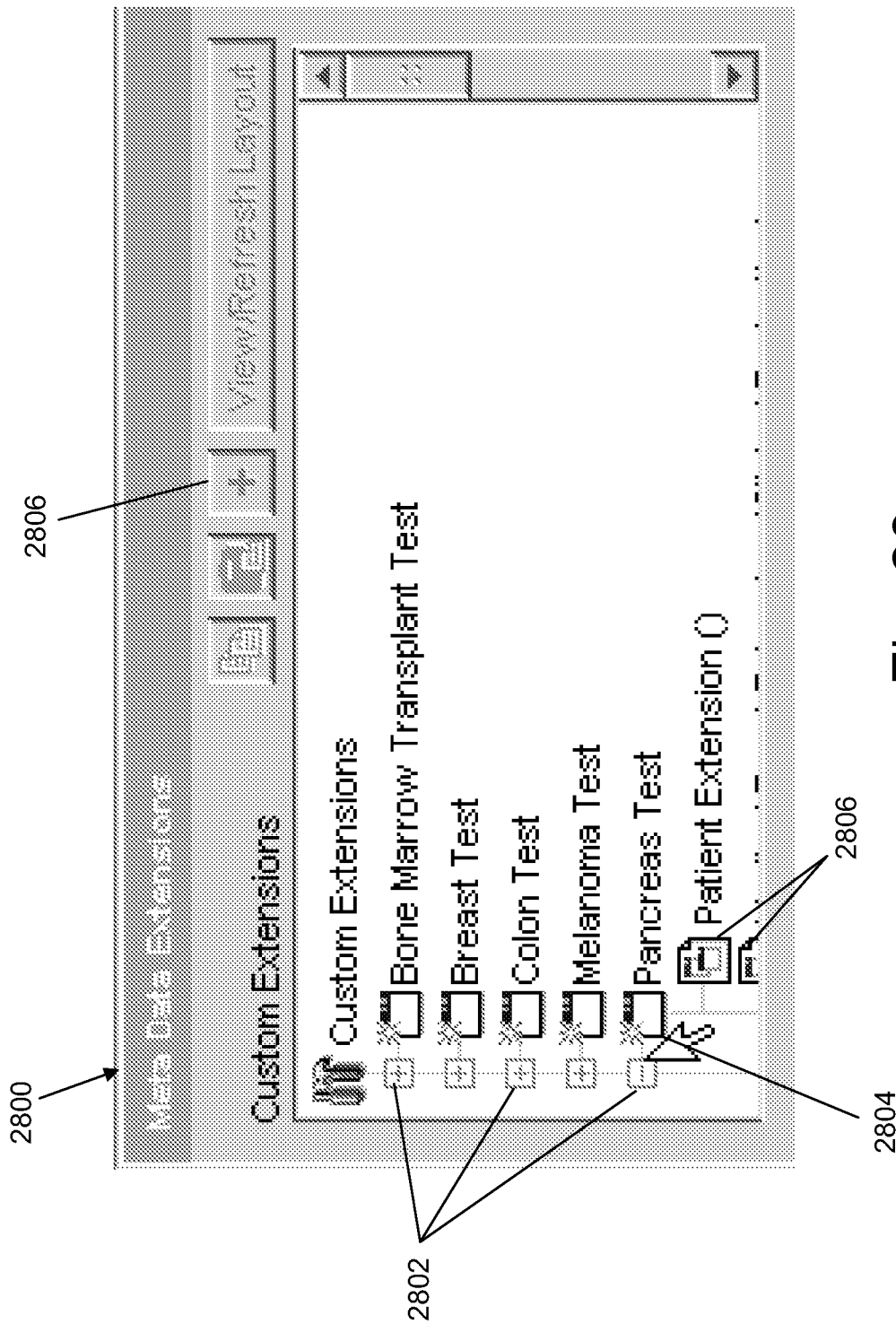
FIG. 28 depicts a first window of a metabuilder application in accordance with an exemplary embodiment.

Metabuilder application 120 provides the ability to include user extensible data configured by the end user into medical research application 116 and/or BST application 118. Metabuilder application 120 may be accessed from medical research application 116 and/or BST application 118, for example, using a button. In an exemplary embodiment, a user also may access metabuilder application 120 from first computing device 102 using browser application 114. One or more windows may be presented to the user. With reference to FIG. 28, a custom extensions window 2800 may be presented, for example, at display 104 using browser application 114. Extensible data may be added at multiple points in a hierarchy associated with the functionality provided, for example, by medical research application 116. In the exemplary embodiment of FIG. 28, a cancer test extension constitutes the highest level of extension and identifies a group of one or more windows associated with the presentation and entry of data for one or more cancer tests.

In the exemplary embodiment of FIG. 28, the user selects a first group resource 2804 from a plurality of group resources 2802 in which to add extensible data for presentation, modification, reporting, etc. using an application such as medical research application 116 or bio-sample tracking application 118. In the exemplary embodiment of FIG. 28, the plurality of group resources 2802 are associated with cancer tests. The user can display or hide details associated with each of the plurality of group resources 2802 using icons associated with a tree view as known to those skilled in the art. The plurality of group resources 2802 may include one or more data extensions 2806. Expanding the data tree for one or more of the plurality of group resources 2802 causes the one or more data extensions 2806 that have been previously added to that group resource to appear as the next level of the data tree. In the exemplary embodiment of FIG. 28, the one or more data extensions 2806 can be associated with a user interface window presented to a user associated with the conduct of a cancer test (group resource).

Figure 29:
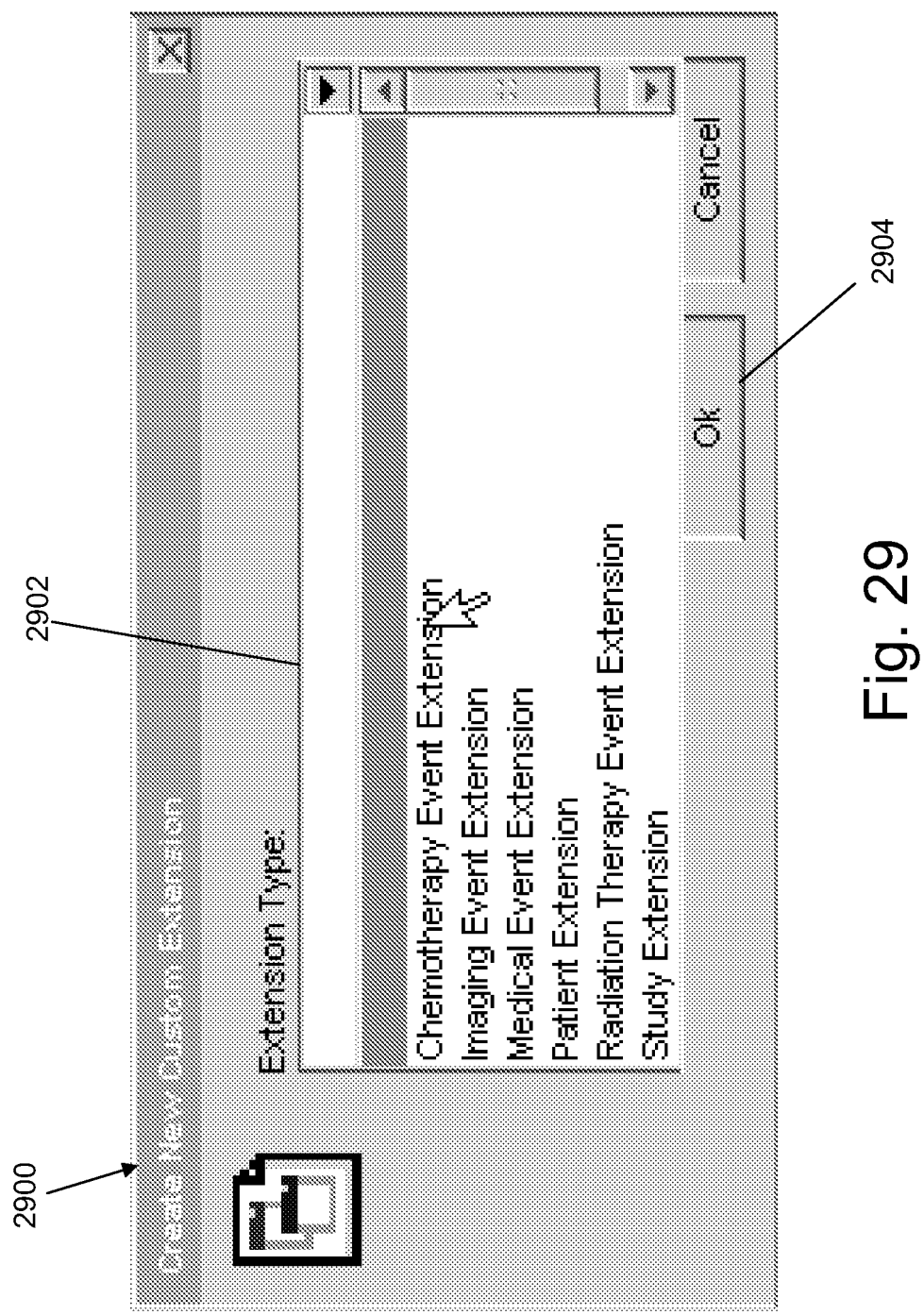
FIG. 29 depicts an add extension window of the metabuilder application of FIG. 28 in accordance with an exemplary embodiment.

Selection of an add button 2806 after selection of a group resource, such as first group resource 2804, of the plurality of group resources 2802 allows the user to create a new data extension which can be added to the selected group resource. With reference to FIG. 29, a new extension window 2900 may be presented at display 104 in response to selection of add button 2806. New extension window 2900 includes an extension type drop down 2902. The user selects an extension type using extension type drop down 2902 which most closely matches the desired data entry requirements for the new extension. In an exemplary embodiment, a first field may be presented in which the user may select/enter the kind of record to which the extension appears to limit the kind of record for which the record appears. Selection of a create button 2904 saves the extension as an instance of a class, for example as an instance of an Attribute Configuration class, in database 120 and adds the extension to the data tree under the selected group resource. A new extension is created, but no tabs or fields have yet been added to the new extension.

Figure 30:
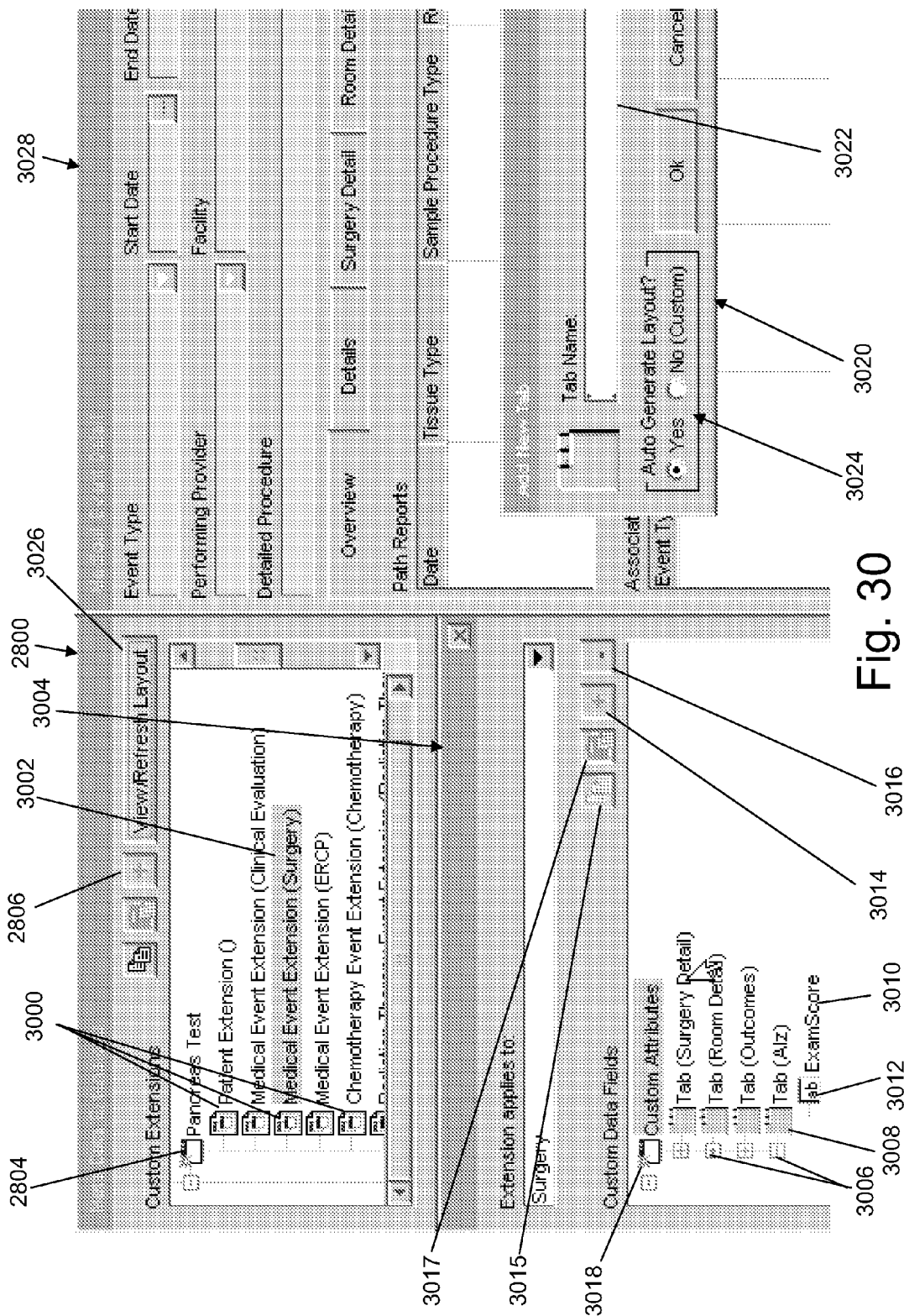
FIG. 30 depicts a main window of the metabuilder application of FIG. 28 in accordance with an exemplary embodiment.

With reference to FIG. 30, tabs and fields where data is collected for an extension can be created. Below first group resource 2804 is a list of extensions 3000 associated with first group resource 2804 which have been modified to include extensible data. In the exemplary embodiment of FIG. 30, first group resource 2804 is associated with a pancreas test and the list of extensions 3000 includes a plurality of custom user interface windows. In the exemplary embodiment of FIG. 30, a first extension 3002 associated with a medical event for surgery is selected as indicated through highlighting. In a second window 3004, one or more custom user interface items 3006 defined for first extension 3002 are shown using a tree view. In the exemplary embodiment of FIG. 30, the one or more custom user interface items 3006 include a plurality of tabs. Below each of the plurality of tabs, the user may display a list of data items added to the tab. In the exemplary embodiment of FIG. 30, a tab 3008 includes a first data item 3010 titled "ExamScore". An indicator 3012 indicates the data type for first data item 3010.

Second window 3004 may include a copy button 3015, a paste button 3017, an add button 3014, and a remove button 3016. Selection of add button 3014 allows the user to create a new tab or a new field depending on the selected item in second window 3004. For example, if a first tree level 3018 is selected by the user, a subsequent selection of add button 3014 causes presentation of a third window 3020. Third window 3020 includes a text field 3022 for entry of a tab name and radio buttons 3024 for layout generation. Radio buttons 3024 allow the user to select whether or not the tab generation is automatic or custom defined by the user. Selection of an "Ok" button 3026 closes third window 3024 and adds the tab extension to the one or more custom user interface items 3006 with the defined tab name. The tab extension is saved as an instance of a class such as an instance of an Attribute Container class in database 120.

Figure 31:
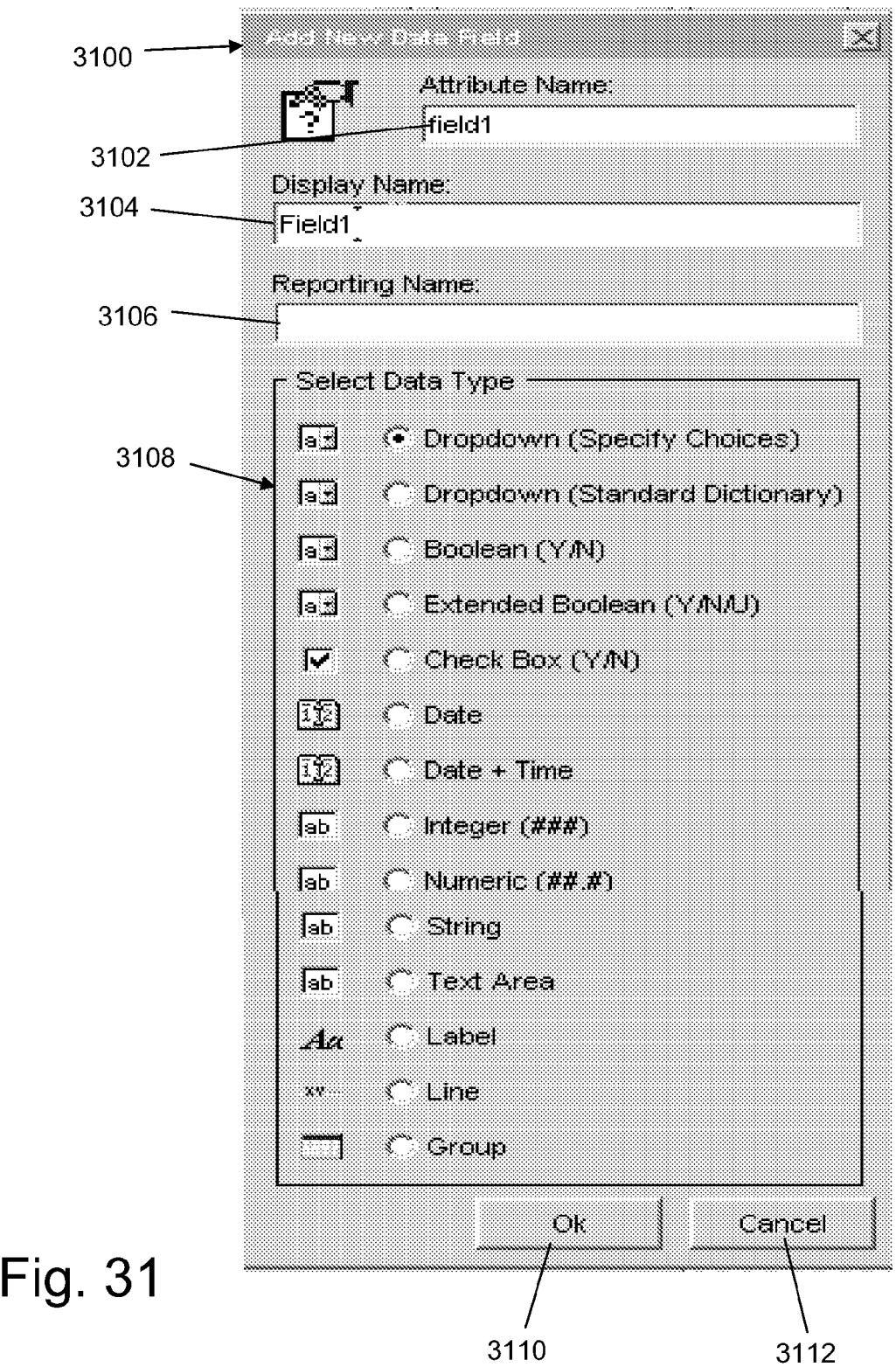
FIG. 31 depicts an add field window of the metabuilder application of FIG. 28 in accordance with an exemplary embodiment.
Figure 32:
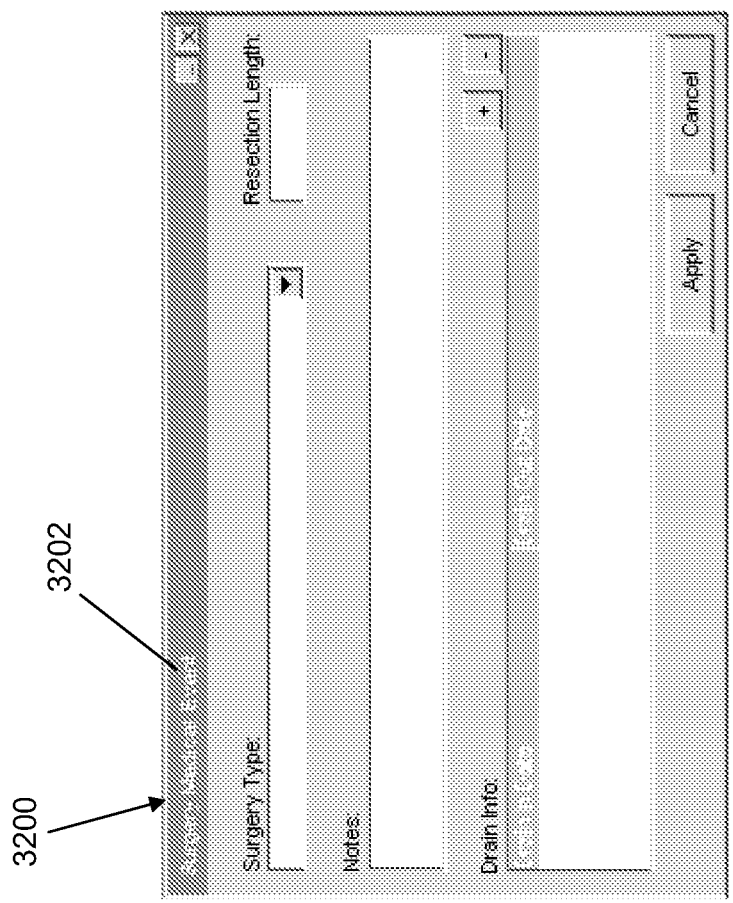
FIG. 32 depicts a configure-on-demand window in accordance with an exemplary embodiment.

If tab 3008 is selected by the user, a subsequent selection of add button 3014 causes presentation of a fourth window 3100 shown with reference to FIG. 31 in accordance with an exemplary embodiment. Fourth window 3100 may include an attribute name field 3102, a display name field 3104, a reporting name field 3106, a data type selector 3108, an "Ok" button 3110, and a cancel button 3112. In the exemplary embodiment of FIG. 31, data type selector 3108 is a plurality of radio buttons. Each radio button of the plurality of radio buttons is associated with a data type. Exemplary data types include a drop down menu in which the user specifies choices available for selection by the user, a drop down menu in which the choices available for selection by the user are selected from a dictionary, a Boolean, a check box, a date, a date and time, an integer, a numeric value, a string, a text area, a label, a line, and a group. Selection of "Ok" button 3110 closes fourth window 3100 and adds the field to the tree under tab 3008 with the attribute name defined in attribute name field 3102 and indicator 3012 indicating the selected data type. Attribute name field 3102 is stored as an instance of a class such as an Attribute class with Attribute Choice class instances for the individual dropdown choices. The display name defined in display name field 3104 appears on the edit screen for this field when presented, for example, in medical research application 116. Selection of cancel button 3112 closes fourth window 3100, but does not add the field to the tree under tab 3008.

Selection of copy button 3015 copies a selected extension. A subsequent selection of paste button 3017 pastes a copy of the copied extension into a group/resource for use as a starting point for designing a new extension. As a result, the user can start with a similar extension as a template, rather than having to design an extension from scratch.

With continuing reference to FIG. 30, selection of a remove button 3016 allows the user to delete a tab or a field depending on the highlighted item in second window 3004. Positioning of the field on the screen may be done using default positioning or X/Y positioning. Using default positioning, meta-builder application 118 determines where to place the field on the edit screen. The default layout has a standard width and uses a default of three fields maximum in one row though this is merely exemplary. Using X/Y positioning, the user decides where to place the field on the edit screen. The fields are first added to the plurality of tabs 3006 or to tab 3008. The user selects a "View/Refresh Layout" button 3026. A screen layout 3028 is presented from which the user can drag the controls into the desired placement. The user can also specify the field height and width. Screen layout 3028 is a mockup of what the screen will look like when presented to a user for data collection, for example, using medical research application 116.

A meta attribute model to support the extensible data may be represented as a Java package and be deployed as a Java archive (JAR) file. From a class perspective, the meta attribute model includes two main aspects: a definitional aspect (i.e. a "tag") and a runtime aspect (i.e. a "value"). The main definitional class is for an Attribute, which identifies a piece of extensible data to be collected. The Attribute has a data type, which defines the kind of value to be collected. The data types supported by the model include the data types selectable using data type selector 3108.

The meta attribute model supports the generalized concept of attaching extensible data to any persistent object in an application such as medical research application 116 or BST application 118. For example, users can define extensible data for patients, medical events, tumors, study enrollments, pathology reports, etc. In the model, these objects are considered Attribute Contexts, meaning they have a set of attributes (extensible data) associated with them. Different kinds of extensible data may be collected for the same Attribute Context. For example, a medical event (the Attribute Context) may have a different set of extensible data depending on the event type. To represent a differing set of extensible data, the model uses a class Attribute Configuration, which represents a level at which a set of extensible data (i.e. the Attributes) is defined. Thus, an Attribute Configuration class may be identified by its Attribute Context and other data set filters like the event type and a set of Attributes.

Attributes can be organized under a group attribute. This hierarchy allows a set of attributes to be represented as a "row" while the collection of "rows" represents the group attribute. For example, a group attribute named "Drain Info" may include a drain in date and drain out date as child Attributes as shown below in Table 1.

TABLE 1

Drain Info:

| Drain In | Drain Out |
|---|---|
| Sep. 1, 2005 3:00 pm | Sep. 2, 2005 4:00 pm |
| Sep. 3, 2005 10:00 am | Sep. 4, 2005 10:20 am |

In addition to describing the kind of extensible data to be collected, the meta attribute model can describe the way that the user interface presents the extensible data. A class Graphical Attribute, which is a subclass of Attribute, represents the customizable user interface aspect of the Attribute. For example, Graphical Attribute contains information about layout (x,y), size (width, height), and tab order. Graphical Attributes may be organized in Attribute Containers, which include panels or tabs. The Graphical Attributes in the Attribute Container are organized automatically (default positioning) or if desired, can be organized (and sized) based on a custom layout defined by the user (X/Y positioning). The appropriate attribute information is defined using meta-builder application 120. At runtime, portions of an Altio defined window may be created dynamically, based on the Attribute and Graphical Attribute data collected for an Attribute Configuration. For example, with reference to FIG. 32, a custom window 3200 is shown in accordance with an exemplary embodiment. The meta attribute model associated with creation of custom window 3200 is defined in Table 2. The attribute context defined as "Medical Event" and the event type defined as "Surgery" by the user form the window header 3202 as "Surgery Medical Event".

TABLE 2

| Name | Grouped Under (GroupAttribute) | Data Type | Attribute Choices | Tab Order |
|---|---|---|---|---|
| Surgery Type | | Attribute Choice | Excisional Resection w/o limb resalvage<br>Excisional Resetion with limb salvage<br>Intralesional Resection<br>Other | 1 |
| Resection Length | | Integer | | 2 |
| Notes | | Long Text | | 3 |
| Drain Info | | Grouped Attribute | | 4 |
| Date In | Drain Info | Date | | 1 (within Group) |
| Date Out | Drain Info | Date | | 2 (within Group) |

At runtime, the data in the meta attribute model is used to construct custom window 3200. For example, a "configure-on-demand" (COD) window can be rendered using the Altio-Live suite of software developed by Altio. Altio's COD feature allows a backend command to generate XML at runtime that represents an Altio window. This XML is interpreted by Altio's Presentation Manager and rendered as a window in an Altio container, which enables medical research application 116 and/or BST application 118 to present a customized user interface based on the meta attribute data defined using meta-builder application 120. To utilize this feature, a set of classes that closely model Altio's concept of a window is used to encapsulate the code needed to generate the requisite XML.

A high level class in a COD package contains a method (or a set of methods) for building the Altio window XML based on the Attributes organized in the Attribute Container or set of Attribute Containers. Only a portion of the window may be configurable. A COD application programming interface (API) performs the work of building the configurable portion of the screen and "inserting" it into the fixed XML that defines the standard part of the window created. When the user enters and saves data, the data is stored as Attribute Values. The set of Attribute Values stored for a given Attribute Configuration are stored in an Attribute Value Set. Using this class hierarchy allows the attachment of Attribute Values to any persistent object in an application, such as medical research application 116, because the Attribute Value has no reference to its "parent". Thus, the association flows downward, from the parent (e.g. the Medical Event) to its Attribute Value Set, and subsequently to its Attribute Values.

In order to better support the various representations of values, including the primitive data types as well as list selections, an AttributeValue class has various subclasses which correspond to the different data types. Exemplary data types which correspond with data types included in data type selector 3108 include: AttributeValueString, AttributeValueLongText, AttributeValueBoolean, AttributeValueExtendedBoolean, AttributeValueInteger, AttributeValueNumeric, AttributeValueDate, AttributeValueDateTime, AttributeValueChoice, AttributeValueDictionary.

Run time data collected may be represented as indicated in Table 3 using a tag format as known to those skilled in the art.

TABLE 3

| Attribute Name | Subclass | Value |
|---|---|---|
| Smoking History | AttributeValueChoice | 1 (Never smoked) |
| Number of Children | AttributeValueInteger | 3 |
| Date of Last Mammogram | AttributeValueDate | Jan. 20, 2004 |

In general, each field on the configurable tabs of the window are captured as an AttributeValue. However, multiple attribute values may be captured for a screen element. For example, an Attribute may be defined as multi-valued in which the user can select more than one value for the screen element. Typically, this is used to define a multi-select list such as a drop down menu from which multiple selections may be made. For example, to capture different Allergies a patient may have a multi-value Attribute as shown in Table 4 below:

TABLE 4

| Attribute Name | Subclass | Value |
|---|---|---|
| Allergies | AttributeValueChoice | 1 (Pollen) |
| Allergies | AttributeValueChoice | 2 (Mold) |

As a second example, attributes organized within a Group Attribute and entered as shown in Table 5. may be captured as shown in Table 6:

TABLE 5

| Drain In | Drain Out |
|---|---|
| Sep. 1, 2005 3::00 pm | Sep. 2, 2005 4:00 pm |
| Sep. 3, 2005 10:00 am | Sep. 4, 2005 10:20 am |

TABLE 6

| Attribute Name | Group Attribute Name | Subclass | Value | Attribute Group Row ID |
|---|---|---|---|---|
| Drain In | Drain Info | AttributeValueDateTime | Sep. 1, 2005 3:00 pm | 1 |
| Drain Out | Drain Info | AttributeValueDateTime | Sep. 2, 2005 4:00 pm | 1 |
| Drain In | Drain Info | AttributeValueDateTime | Sep. 3, 2005 10:00 am | 2 |
| Drain Out | Drain Info | AttributeValueDateTime | Sep. 4, 2005 10:20 am | 2 |

The following code block illustrates reading of an Attribute Value for an object.

```
Patient patient = (Patient)sess.load(Patient.class, idPatient);
if (patient.getAttributeValueSet( ) != null)
{
    List attributeValues =
    patient.getAttributeValueSet( ).getAttributeValues( );
    for (Iterator i = attributeValues.iterator( ); i.hasNext( ); )
    {
        AttributeValue av = (AttributeValue)i.next( );
        System.out.println(av.getAttribute( ).getDisplayName( ) +
        " = " + av.getValue( ));
    }
}
```

To generate extensible markup language (XML) for attribute values in a way that makes them appear as normal Java data members of the class, the toXMLDocument( ) may be overridden in the class that contains the Attribute Value Set. In the example code block, the Patient.toXMLDocument method has been overridden.

```
public Document toXMLDocument(List list, int dateOutputStyle)
    throws XMLReflectException
{
    Document doc = super.toXMLDocument(list, dateOutputStyle);
    if (this.getAttributeValueSet( ) != null)
    {
        this.getAttributeValueSet( ).appendXMLDocument(doc);
    }
    return doc;
}
```

Because this XML replaces the normal XML generation for an Attribute Value Set, the Attribute Value Set "getter" method is excluded when generating the XML in the example code block below:

```
public void registerMethodsToExcludeFromXML( )
{
    this.excludeMethodFromXML("getAttributeValueSet");
}
```

The following code block illustrates saving an Attribute Value Set for a patient.

```
Attribute isDiabeticAttr = (Attribute)session.load(Attribute.class,
idAttributeIsDiabetic);
Attribute smokingHistringAttr = (Attribute)session.load(Attribute.class,
idAttributeSmokingHistory);
Patient patient = new Patient( );
Patient.setMRN(mrn);
AttributeValueSet avs = new AttributeValueSet( );
avs.setCreateDateTime(new java.util.Date(System.currentTimeMillis( )));
patient.setAttributeValueSet(avs);
sess.save(patient);
sess.flush( );
AttributeValue av = new AttributeValueExtendedBoolean( );
av.setAttribute(isDiabeticAttribute);
av.setValueExtendedBoolean(AttributeValueExtendedBoolean.TRUE);
av.setIdAttributeValueSet(avs.getIdAttributeValueSet( ));
sess.save(av);
sess.flush( );
av = new AttributeValueChoice( );
av.setAttribute(smokingHistoryAttribute);
AttributeChoice theChoice = null;
for (Iterator i1 =
smokingHistoryAttribute.getAttributeChoices( ).iterator( ); i1.hasNext( );)
{
    AttributeChoice choice = (AttributeChoice) i1.next( );
    if (choice.getChoice( ).equals("Never Smoked"))
    {
        theChoice = choice;
        break;
    }
}
av.setValueAttributeChoice(theChoice);
av.setIdAttributeValueSet(avs.getIdAttributeValueSet( ));
sess.save(av);
sess.flush( );
```

The following code block illustrates reading the Attributes for an Attribute Configuration:
String queryString="select attr from Attribute as attr"+ "WHERE attr.configurableContent.codeAttributeContext='PAT'";
List patientAttributes=sess.createQuery(queryString).list( );

The Attribute Value class may be Hibernate mapped so that making the values persist is a straightforward exercise. However, access to each attribute value should be qualified by the name (or identifier) of the Attribute. For example, a query in Hibernate query language (HQL) syntax when the flag isSmoker is represented in a traditional object oriented/relational (O/R) model is shown below.
SELECT pat
FROM Patient as pat
WHERE pat.isSmoker='Y'

The HQL syntax is in contrast to the query when isSmoker is represented as an Attribute Value as shown below.

SELECT pat
FROM Patient as pat
JOIN pat.attributeValueSet as avs
JOIN avs.attributeValues as av WITH av.attribute.attributeName='isSmoker' WHERE av.valueString='Y'

The attribute name qualification may be defined using JOIN criteria and a value comparison may be achieved using a WHERE clause for two reasons. First, in cases where the isSmoker value is returned, it is important that rows not be eliminated from the result set for those patients that do not have an isSmoker attribute value. This may be accomplished by using a LEFT JOIN and applying the attribute name qualification using the join criteria. Use of the WHERE clause to perform the attribute name qualification may eliminate rows Second, for complex selection criteria involving ANDs and ORs, it is important that the parentheses reflect the order of evaluation for the value comparisons not the attribute name qualifications. By isolating the attribute name comparisons in the JOIN criteria, the parentheses can be applied correctly to communicate the proper order of evaluation.

An example query is shown below for multiple selection criteria.

SELECT pat
FROM Patient as pat
JOIN pat.attributeValueSet as avs
JOIN avs.attributeValues as avSmoker WITH avSmoker.attribute.attributeName='isSmoker'
JOIN avs.attributeValues as avDiabetic WITH avDiabetic.attribute.attributeName='isDiabetic' WHERE avSmoker.valueString='Y' AND avDiabetic.valueString='N'

The attribute value's data type is identified in the query. For example, when querying a date, a Hibernate property valueDate may be queried as shown in the example below.

SELECT pat
FROM Patient as pat
JOIN pat.attributeValueSet as avs WITH av.attribute.attributeName='symptomOnsetDate'
JOIN avs.attributeValues as av WHERE av.valueDate>'12/31/2004'

The following list identifies the Hibernate property to query and the corresponding database table column:

| Hibernate Property (Java data member) | Database Table Column |
|---|---|
| valueString | valueString |
| valueBoolean | |
| valueExtendedBoolean | |
| valueDate | valueDateTime |
| valueDateTime | |
| valueInteger | valueInteger |
| valueNumeric | valueNumeric |
| valueAttributeChoice | valueIdAttributeChoice (to join to table AttributeChoice) |
| valueIdDictionary | valueIdAttributeDictionary (to join to table AttributeDictionary) |
| valueLongText | valueIdLongText (to join to table LongText) |

The AttributeValueChoice and AttributeValueDictionary provide a mapping to a selection list. For example, to find all Patients with allergy='Pollen' (an AttributeChoice), the HQL query may be formed as:

SELECT pat
FROM Patient as pat
JOIN pat.aftributeValueSet as avs
JOIN avs.attributeValues as av WITH av.attribute.attributeName='allergy' AND av.valueAttributeChoice.choice='Pollen'

If the id of the 'Pollen' Attribute Choice is known, the query may be formed as:

SELECT pat
FROM Patient as pat
JOIN pat.attributeValueSet as avs
JOIN avs.attributeValues as av WITH av.attribute.attributeName='allergy' AND av.valueAttributeChoice.idAttributeChoice=521

When querying Attribute Values from a standard vocabulary (AttributeValueDictionary), the query has a similar form though the value is represented by a different Hibernate property.

SELECT pat
FROM Patient as pat
JOIN at.attributeValueSet as avs
JOIN avs.attributeValues as av WITH av.attribute.attributeName='deathSource' AND av.valueIdAttributeDictionary=1621

When querying attributes belonging to different Attribute Value Sets, each attribute value set may be joined separately. For example, if the user is searching for patients with particular surgery medical events attribute values and "Followup" medical event attribute values, two different Attribute Configurations are queried. If the search involves looking for patients with a recoveryTimeinMinutes greater than an hour and a medicalComplication='Pulmonary', the search uses two different Attribute Value Sets. As a result, the query joins each Attribute Value Set to avoid returning an empty set in which no medical event has both recoveryTimeinMinutes and medicalComplication as an attribute. The following query illustrates a search across two different Attribute Value Sets:

SELECT pat
FROM Patient as pat
JOIN pat.medicalEvents as mesurg WITH meSurg.eventType.eventType='Surgery'
JOIN meSurg.attributeValueSet as avsSurg
JOIN avsSurg.attributeValues as avSurg WITH avSurg.attribute.attributeName='recoveryTimeInMinutes'
JOIN pat.medicalEvents as meFollow WITH meFollow.eventType.eventType='Follow Up'
JOIN meFollow.attributeValueSet as avsFollow
JOIN avsFollow.attributeValues as avFollow WITH avFollow.attribute.attributeName='medicalComplication'
WHERE avsurg.valueInteger>60 AND avFollow.valueIdAttributeChoice>121

To evaluate an attribute name qualification with its value comparison an OR logical operator with selection criteria on attribute values can be used. Normally, parentheses are used in a query to establish an order of operation. For example, to find all patients where isSmoker "Y" OR is Diabetic "Y", the query may have the following form:

SELECT pat
FROM Patient as pat
LEFT JOIN pat.attributeValueSet as avs
LEFT JOIN avs.attributeValues as avSmoker WITH avSmoker.attribute.attributeName='isSmoker'
LEFT JOIN avs.attributeValues as avDiabetic WITH avDiabetic.attribute.attributeName='isDiabetic' WHERE avSmoker.valueString='Y' OR avDiabetic.valueString='Y'

When Attribute Values organized under a Group Attribute are queried, it may be necessary to restrict the query to meet the criteria of the attributes within a particular Group Attribute "row". For example, to find all patients with a drain that was placed and removed in the first week of September, the query may match the attribute values for one Drain Info "row". This is accomplished by adding the additional criteria which restricts attribute comparison to the same groupAttributeRowId as shown below.

SELECT pat
FROM Patient as pat
JOIN pat.medicalEvents as meSurg WITH meSurg.eventType.eventType='Surgery'
JOIN meSurg.attributeValueSet as avsSurg
JOIN avsSurg.attributeValues as avDrainIn WITH avDrainIn.attribute.attributeName='drainInDate'
JOIN avsSurg.attributeValues as avDrainOut WITH avDrainOut.attribute.attributeName='drainOutDate'
WHERE avDrainIn.valueInteger between ('9/1/2005' and '9/8/2005') AND avDrainOut.valueInteger between ('9/1/2005' and '9/8/2005') AND avDrainIn.groupAttributeRowId=avDrainOut.groupAttributeRowId Medical research application 116 and/or BST application 118 may utilize a Java aspect components framework for basic client-server interactions, but the atomic control of what and how a report is displayed may be controlled using a project specific XML configuration file and report specific classes local to the project and global to the environment. Reports may be described in an XML file (i.e., report.xml) for each project. The XML file may define the following report attributes: a. a report's name, description, processing class, output file name; b. a query for the data in the report; c. owners of a report; d. permissions required to run/view a report; e. columns displayed on the report including their display order and column header names; f. parameters collected for the report's query, including the parameter captions and display order for the report query form, data-type information, and specific dictionary query information if referencing dictionary data.

An example Report.xml file holding a single report description is shown below:

```
<?xml version="1.0" encoding="UTF-8"?>
<Reports winstl="default" hdgfontstl="LISTSTHEADINGh"d gcol="B7D3A4"
rowcol2="EEEEEO" selectcol="FFFFCC" ctrlcapfonbtl="al__LABEL" ctrlfontstl="al.-STD">
    <report name="CustomTest2" title="Custom Report2" description=""
className="ReportPANPatients.ccr">
        <query type="sqlWs" ql="select one,two,three from MyTable where this='__paramI-
'that='__param2-' other='garam3'" hql=""/>
        <owners>
            <Owner name="SARCm description="Sarcoma Groupu/>
        </owners>
        <permissions>
            <permission name="canViewReport" description="User can view reports"/>
            <permission name="canViewIdentity" description="User can view identified dataf'/>
        </permissions>
        <columns>
            <column name="oneM caption="One" displayOrder="I"/>
            <column name="two" caption="Two" displayOrder="2"/>
            <column name="threen caption='Three" displayOrder="4"/>
        </columns>
        <params>
            <param caption="One" name="oneC type="stringU querySubst="-paramI-"
displayOrder="I"/>
            <param caption="TwoV name="twoMt ype="dateS querySubst=",~..pararn2-.d"
isplayOrder="T/>
            <param caption=7hreeU name="threen type="select" querysubst="-paramy
displayOrder=Y>
                <options>
                    <option value="I" display="One"/>
                    <option value="Zn display="Two"/>
                    <option value="3" display="Three"/>
                </options>
            </param>
        </params>
    </report>
</Reports>
```

Figure 33:
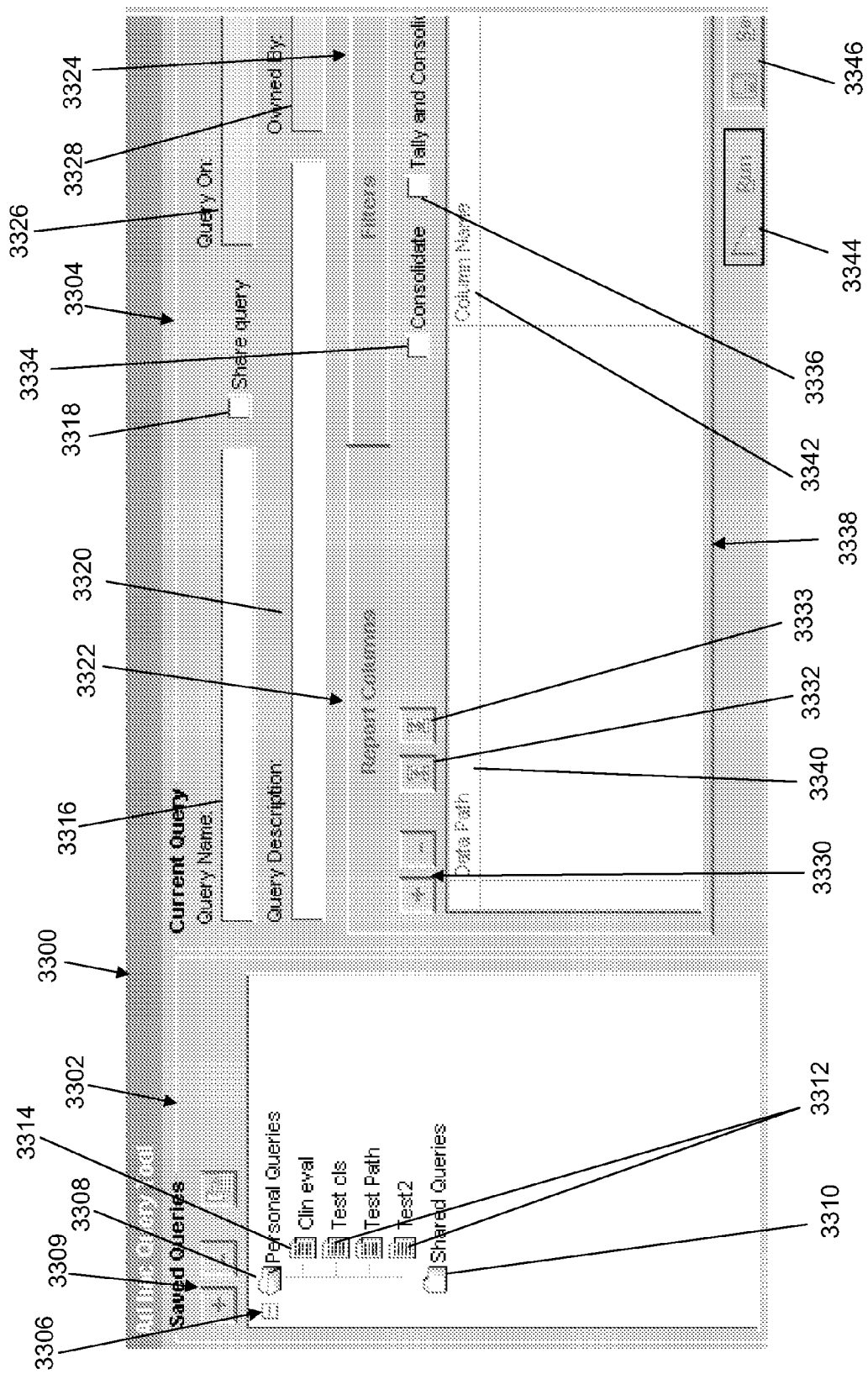
FIG. 33 depicts a main window of an ad hoc query tool in accordance with an exemplary embodiment.

With continuing reference to FIG. 3, selection of ad hoc reporting button 326 may cause presentation of a report generation window 3300 shown with reference to FIG. 33 in accordance with an exemplary embodiment. Report generation window 3300 extracts information from medical research application 116 and/or BST application 118 including extensible data added to medical research application 116 and/or BST application 118 using metabuilder application 120. Users can formulate and run database queries using report generation window 3300, which hides the technical aspects of composing relational database queries from the user. Report generation is accomplished using a set of browser-based windows that run, for example, in the Altio user interface environment.

Report generation window 3300 provides a means for extracting information from medical research application 116 and/or BST application 118 by building, running, and reusing custom queries. In general, the user formulates a query by selecting report columns and applying filters or selection criteria for defining the data to be reported. Report generation window 3300 may include a query selection section 3302 and a query definition section 3304. Query selection section 3302 may include a tree view 3306, which may include a personal query folder 3308 and a shared query folder 3310. Personal query folder 3308 includes one or more query files 3312. Similarly, shared query folder 3310 may include one or more shared query file (not shown). The list of reports presented using personal query folder 3308 and shared query folder 3310 may be read from a cached list or processed from an XML file if there have been changes to the XML configuration. The class receives an action parameter from a request telling it to return the report list. The report list displayed may be controlled based on ownership and permission criteria defined by the project and based on the current user. The user may add/remove queries (reports) using add/remove buttons 3309.

Query definition section 3304 may include a query name text box 3316, a share query selector 3318, a query description text box 3320, a report column tab 3322, a filter tab 3324, a query path text box 3326, a query owner text box 3328, a run button 3344, and a save button 3346. The user defines a name for identifying the query using query name text box 3316. The name identifies the query in the one or more query files 3312. Selection of share query selector 3318 adds the query to shared query folder 3310. De-selection of share query selector 3318 adds the query to personal query folder 3308. The user can describe the query in more detail using the query description text box 3320.

Report column tab 3322 may include add/remove buttons 3330, a move up button 3332, a move down button 3333, a consolidate selector 3334, a "tally and consolidate" selector 3336, and a report column grid 3338. The user may add/remove columns to a report using the add/remove buttons 3330. The user may define an order for presentation of the columns in the report using move up button 3332 and move down button 3333. Selection of move up button 3332 shifts the report column to the left and selection of move down button 3333 shifts the report column to the right. Selection of consolidate selector 3334 consolidates identical information into a single row of information in the query so that a list of unique records or values is displayed. Similarly, selection of "tally and consolidate" selector 3336 consolidates identical information into a single row of information in the report. Additionally, however, selection of "tally and consolidate" selector 3336 causes an additional column to be added to the report showing the number of records that match the information displayed in that row. Thus, the report includes a list of unique values with a count of how many times each unique value appears among the records included in the query. Report column grid 3338 may include a data path identifier column 3340 and a column name column 3342. Data path identifier column 3340 defines the data path for the data item to be evaluated in the column of the report. Column name column 3342 defines the header for the column in the report generated.

The user executes the defined queries for each column to generate a report using run button 3344. Selection of run button 3344 invokes a request to AdhocRunQuery.java which passes in the query definition defined in report column tab 3322 and in filter tab 3324. The request is processed, checking the ownership and permission criteria. The identified parameters are loaded into the requested report object and the resulting success page is set based on the format passed in the request. When the query is executed, the results are returned in a grid. The user saves the defined queries for each column using save button 3346 for later execution or modification. An existing query can be copied and modified to define a new query definition. The defined queries associated with a report generation are included in personal query folder 3308 or shared query folder 3310 depending on the status of share query selector 3318.

Figure 34A:
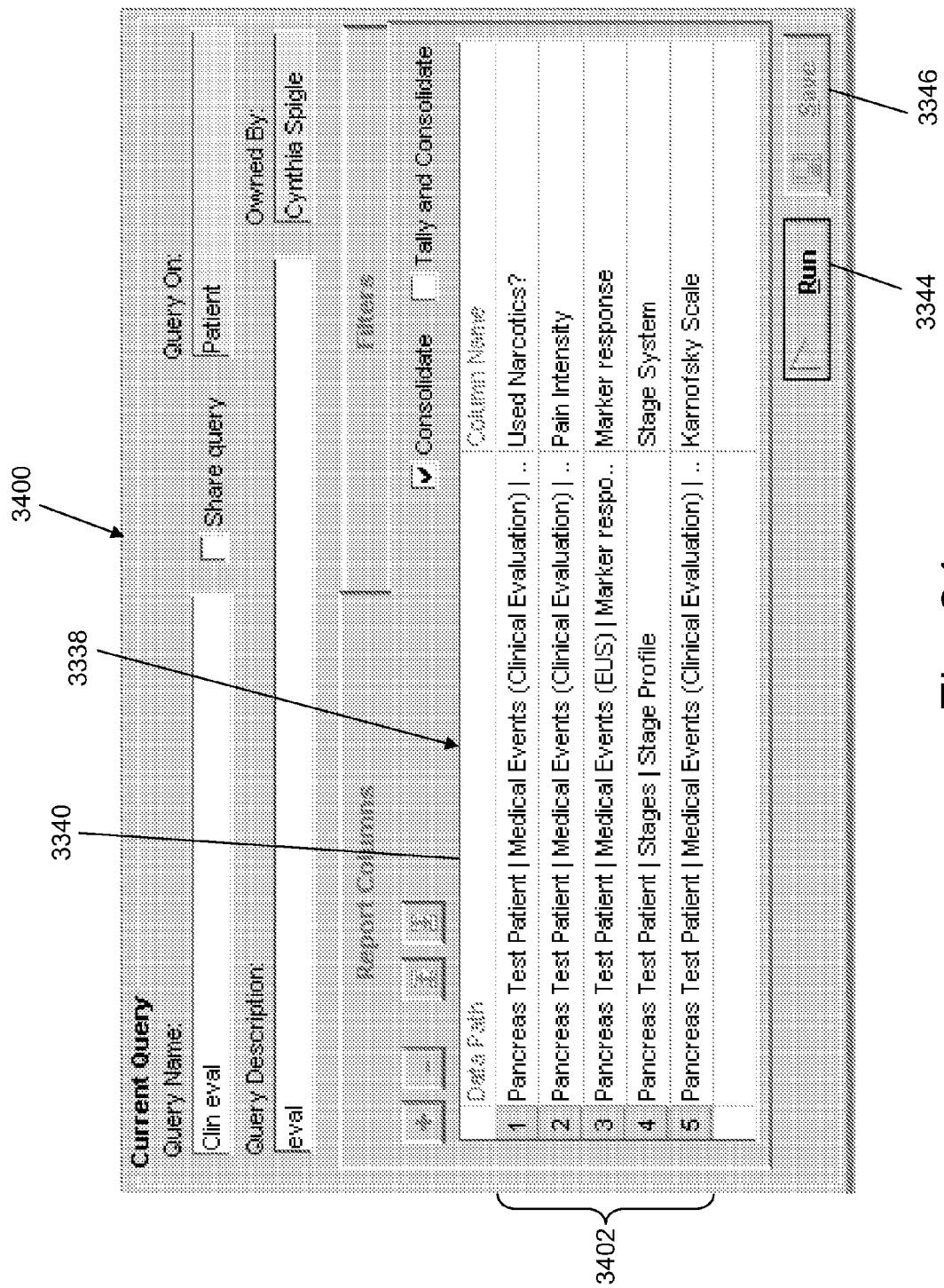
FIG. 34a depicts a report tab of the ad hoc query tool of FIG. 33 in accordance with an exemplary embodiment.

Selection of a query folder from personal query folder 3308 or shared query folder 3310 causes presentation of the current query information in query definition section 3304. For example, selection of a query folder 3314 from the one or more query files 3312 causes presentation of a first query definition section 3400 shown with reference to FIG. 34a. Selection of query folder 3314 invokes a request to AdhocRunQuery.java, which includes the report name and requests the query for the named report. Execution of first query definition section 3400 defines five columns of data 3402. The data path parameters defined in data path identifier column 3340 are organized similarly to the display of a directory structure on a disk with a vertical line ("|"), or pipe, separating different levels or data groupings until the last item is reached, which is the name of a field. As a result, related elements are grouped together in directories and subdirectories. As rows are added to report column grid 3338, the data structure is represented much like files and folders are displayed in a computer file system.

Figure 34B:
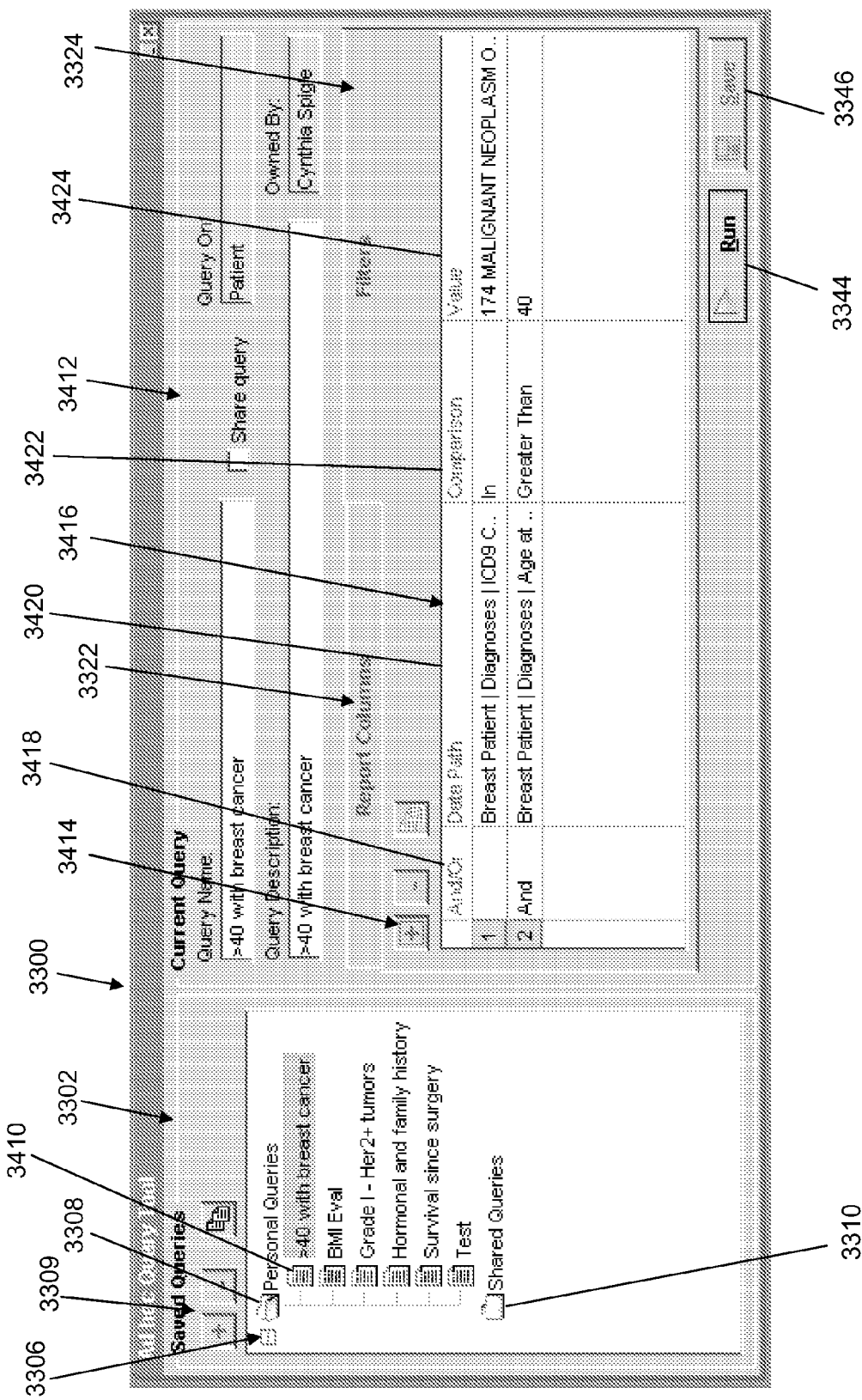
FIG. 34b depicts a filter tab of the ad hoc query tool of FIG. 33 in accordance with an exemplary embodiment.

With reference to FIG. 34b, selection of a query folder 3410 from the one or more query files causes presentation of a second query definition section 3412. Filter tab 3324 may include add/remove buttons 3414 and a filter grid 3416. The user may add/remove filters using the add/remove buttons 3414. Each row of filter grid 3416 defines a filter to be applied to data identified based on the query. Filter grid 3416 may include a boolean connector column 3418, a data path identifier column 3420, a comparator selection column 3422, and a comparison value column 3424. Boolean connector column 3418 includes a selection for defining how to combine the filters defined by each row of filter grid 3416. Boolean connectors include "and" and "or". Similar to data path identifier column 3340, data path identifier column 3420 defines the data path for the data item to be evaluated using the filter. Comparator selection column 3422 defines a type of comparison performed by the filter such as greater than, less than, greater than or equal to, less than or equal to, equal to, in, not in, etc. Comparison value column 3424 defines a value(s) to which to compare the data item using the parameter defined in the corresponding comparator selection column 3422.

Figure 35:
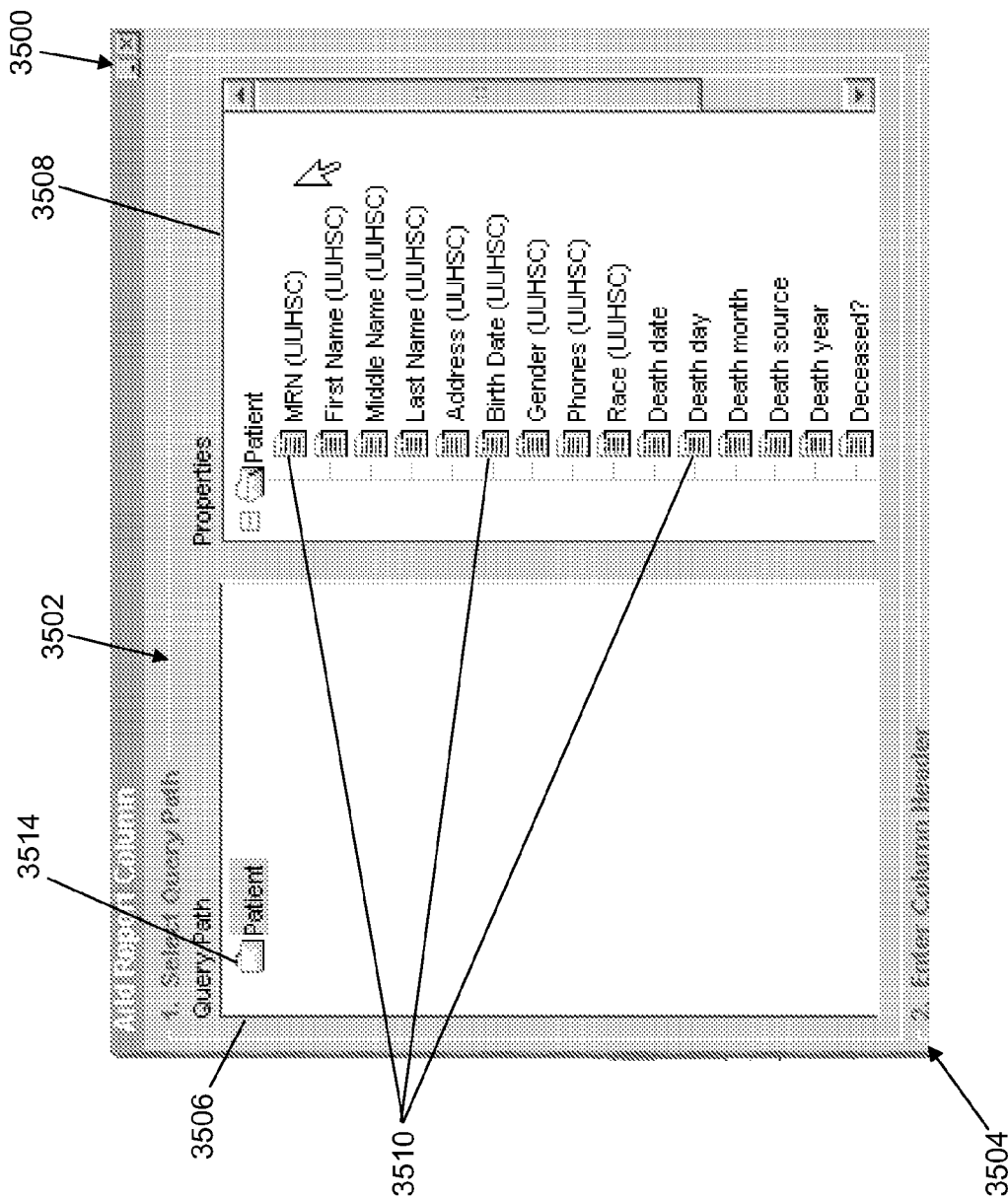
FIG. 35 depicts an add report column of the ad hoc query tool of FIG. 33 in accordance with an exemplary embodiment.

User selection of an add button of the add/remove buttons 3309 may cause presentation of an add report column window 3500 shown with reference to FIG. 35. Add report column window 3500 may include a select query path section 3502 and a column header section 3504. Select query path section 3502 may include a query path window 3506 and a property window 3508 which present a user with two tree components that are used to select the data path and that allow the user to compose complex query paths by drilling down into a folder structure. Query path window 3506 includes one or more path folders which represent an object in the data model. For example, in the exemplary embodiment of FIG. 35, query path window 3506 includes a path folder 3514 for a "Patient" object. The user double-clicks on a folder in query path window 3506, such as path folder 3514, in order to drill down into a data path. The user can continue to drill down into the data path until presented with a list of available report columns 3510 included in property window 3508. Each available report column in property window 3508 represents an actual property (table column) of the data model. The user double-clicks on a report column to add it to the report. Additionally, the user may enter a report column header name in a text field (not shown) presented in column header section 3504.

Figure 36:
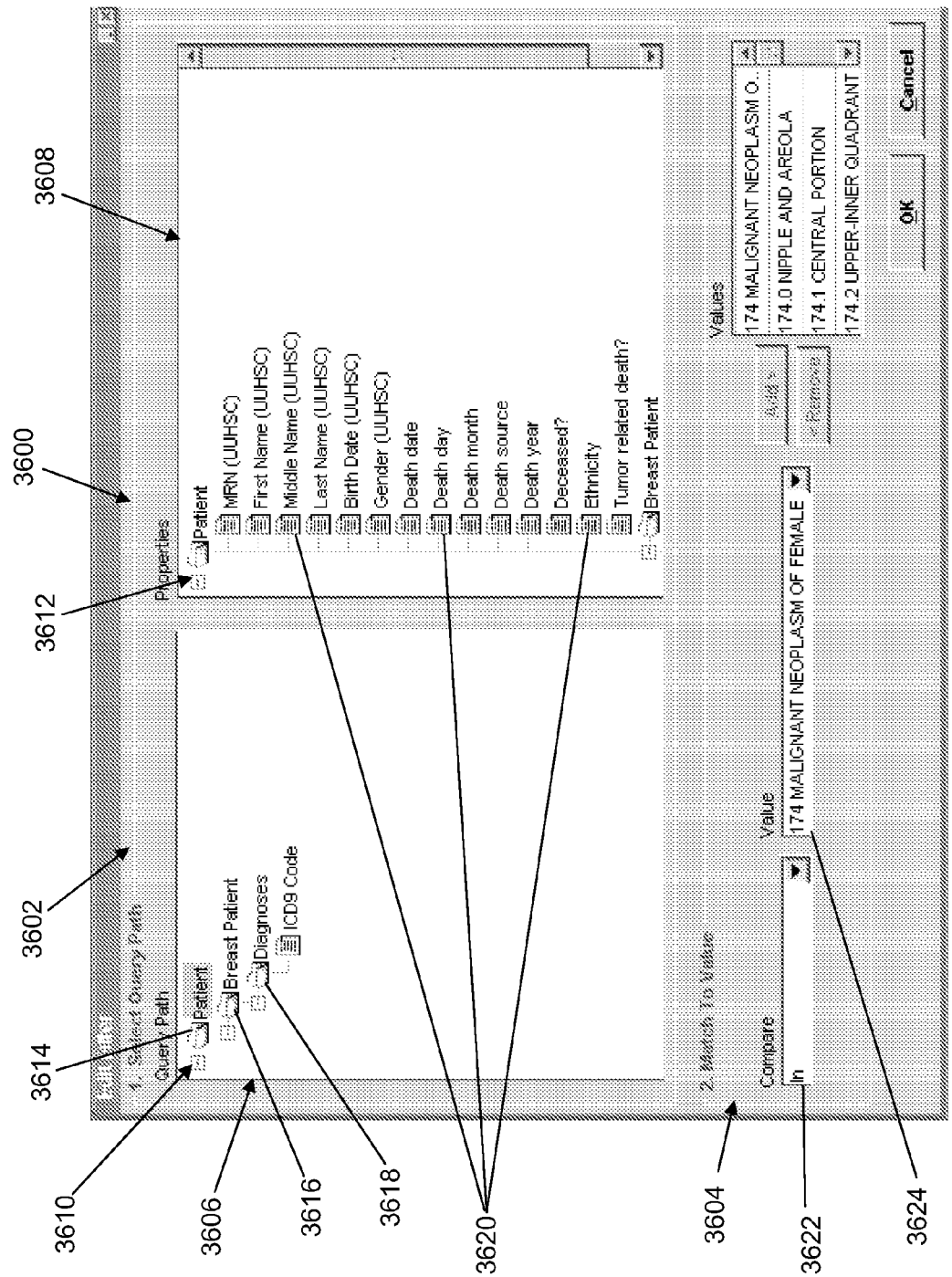
FIG. 36 depicts an edit filter window of the ad hoc query tool of FIG. 33 in accordance with an exemplary embodiment.

User selection of an add button of the add/remove buttons 3414 may cause presentation of an add filter window 3600 shown with reference to FIG. 36. Adding a filter works much the same way as adding a report column. Add filter window 3600 may include a select query path section 3602 and a comparison section 3604. Select query path section 3602 may include a query path window 3606 and a property window 3608 which present a user with a first tree component 3610 and a second tree component 3612 that are used to select the data path and that allow the user to compose complex query paths by drilling down into a folder structure. First tree component 3610 includes one or more path folders which represent an object in the data model. For example, in the exemplary embodiment of FIG. 36, first tree component 3610 includes a first path folder 3614 for a "Patient" object, a second path folder 3616 for a "Breast Patient" object, and a third path folder 3618 for a "Diagnoses" object. The user double-clicks on a folder 3614, 3616, 3618 in first tree component 3610 in order to drill down into a data path. The user can continue to drill down into the data path until presented with a desired list of available filter data items 3620 in property window 3608. Each available filter data column in property window 3608 represents an actual property of the data model. The user selects the appropriate filter data column from the desired list of available filter data items 3620. The column selected represents the property on which filter criteria will be applied. The user selects a comparator type from a comparator drop-down field 3622 of comparison section 3604. Comparator drop-down field 3622 describes how values in the field should be compared with the value(s) entered as a test for each record's inclusion in the query. The user selects and/or enters a value (or values if applicable) in a value field 3624 of comparison section 3604. The data in the specified field for each record is compared to the value(s) entered in value field 3624 based on the selected comparator type to determine inclusion in the query. The type of data entry field of value field 3624 may differ based on the comparator type selected in comparator drop-down field 3622. For example, if the comparator type is "greater than", value field 3624 may be text box which allows the user to enter a numeric value. If the comparator type is "in", value field 3624 may be a drop down box which allows the user to select a plurality of parameters which define a set. Additional controls may be added to allow the user to add or remove items from the defined set.

The exemplary embodiments may be implemented as a method, apparatus, or article of manufacture using standard programming and/or engineering techniques to produce software, firmware, hardware, or any combination thereof to control a computer to implement the disclosed embodiments. The term "computer readable medium" can include, but is not limited to, magnetic storage devices (e.g., hard disk, floppy disk, magnetic strips, . . . ), optical disks (e.g., compact disk (CD), digital versatile disk (DVD), . . . ), smart cards, flash memory devices, etc. Additionally, it should be appreciated that a carrier wave can be employed to carry computer-readable media such as those used in transmitting and receiving electronic mail or in accessing a network such as the Internet or a local area network (LAN).

The foregoing description of exemplary embodiments of the invention have been presented for purposes of illustration and of description. It is not intended to be exhaustive or to limit the invention to the precise form disclosed, and modifications and variations are possible in light of the above teachings or may be acquired from practice of the invention. The functionality described may be implemented in a single executable or application or may be distributed among modules that differ in number and distribution of functionality from those described herein. Additionally, the order of execution of the functions may be changed depending on the embodiment. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A device for extending a user interface to include additional data fields, the device comprising:
   a hardware storage device having computer-readable instructions therein which are programmed to receive a first response at a first application, wherein the first application controls presentation of a first plurality of linked user interface windows when executed, wherein the first response indicates a first selection of an add button from a first window of the first plurality of linked user interface windows, wherein the add button is associated with addition of a data field to a first window of a second plurality of linked user interface windows presented as part of a user interface of a second application when the second application is executed, wherein the second application controls presentation of the second plurality of linked user interface windows when executed, and further wherein the data field accepts data for a new attribute not previously presented in the second plurality of linked user interface windows when the second application is executed;
   control presentation of a second window of the first plurality of linked user interface windows to a user of the first application;
   receive a second response at the first application, wherein the second response includes a name for the data field entered by the user using the presented second window and a data type of the data field;
   identify a position of the data field to be presented on the first window of the second plurality of linked user interface windows; and
   store the received name, the received data type, and the identified position for the data field, wherein the data field is presented in the first window of the second plurality of linked user interface windows at the stored position using the stored name when a second user executes the second application and is configured to allow the second user to define a value for the new attribute of the data field; and
   a processor, the processor coupled to the hardware storage device and configured to execute the instructions.

2. A hardware storage device including computer-readable instructions that, upon execution by a processor, cause the processor to extend a user interface to include additional data fields, the instructions configured to cause a computing device to:
   receive a first response at a first application, wherein the first application controls presentation of a first plurality of linked user interface windows when executed, wherein the first response indicates a first selection of an add button from a first window of the first plurality of linked user interface windows, wherein the add button is associated with addition of a data field to a first window of a second plurality of linked user interface windows presented as part of a user interface of a second application when the second application is executed, wherein the second application controls presentation of the second plurality of linked user interface windows when executed, and further wherein the data field accepts data for a new attribute not previously presented in the second plurality of linked user interface windows when the second application is executed;
   control presentation of a second window of the first plurality of linked user interface windows to a user of the first application;

receive a second response at the first application, wherein the second response includes a name for the data field entered by the user using the presented second window and a data type of the data field;

identify a position of the data field to be presented on the first window of the second plurality of linked user interface windows; and store the received name, the received data type, and the identified position for the data field, wherein the data field is presented in the first window of the second plurality of linked user interface windows at the stored position using the stored name when a second user executes the second application and is configured to allow the second user to define a value for the new attribute of the data field.

3. A method of extending a user interface to include additional data fields, the method comprising:

receiving a first response at a first application executing at a computing device, wherein the first application controls presentation of a first plurality of linked user interface windows when executed, wherein the first response indicates a first selection of an add button from a first window of the first plurality of linked user interface windows, wherein the add button is associated with addition of a data field to a first window of a second plurality of linked user interface windows presented as part of a user interface of a second application when the second application is executed, wherein the second application controls presentation of the second plurality of linked user interface windows when executed, and further wherein the data field accepts data for a new attribute not previously presented in the second plurality of linked user interface windows when the second application is executed;

controlling presentation of a second window of the first plurality of linked user interface windows to a user of the first application executing at the computing device;

receiving a second response at the first application executing at the computing device, wherein the second response includes a name for the data field entered by the user using the presented second window and a data type of the data field;

at the computing device, identifying a position of the data field on the first window of the second plurality of linked user interface windows; and storing the received name, the received data type, and the identified position for the data field at the computing device, wherein the data field is presented in the first window of the second plurality of linked user interface windows at the stored position using the stored name when a second user executes the second application and is configured to allow the second user to define a value for the new attribute of the data field.

4. The method of claim 3, further comprising receiving a selection of a type of persistent object of the second application to which the data field is associated.

5. The method of claim 3, wherein the data type is selected by the user using the presented second window.

6. The method of claim 3, wherein the second response further comprises an attribute name for the data field entered by the user using the presented second window and further wherein the attribute name for the data field is stored.

7. The method of claim 3, wherein the second response further comprises a reporting name for the data field entered by the user using the presented second window and further wherein the reporting name for the data field is stored.

8. The method of claim 3, further comprising:
receiving a third response at the first application executing at the computing device, wherein the third response indicates a second selection of a view layout button;
controlling presentation of a screen layout of the first window of the second plurality of linked user interface windows in response to the second selection of the view layout button; and
receiving a fourth response at the first application executing at the computing device, wherein the fourth response includes the position selected by the user by moving the data field in the presented screen layout.

9. The method of claim 3, further comprising:
receiving a third response at the first application executing at the computing device, wherein the third response indicates a second selection of a delete button, wherein the delete button is associated with deletion of a second data field from the first window of the second plurality of linked user interface windows of the second application; and
receiving a fourth response at the first application executing at the computing device, wherein the fourth response includes a second name for the second data field identified by the user;
wherein the first window of the second plurality of linked user interface windows is presented to the second user with the second data field removed when the second user executes the second application.

10. The method of claim 3, further comprising:
receiving a third response at the first application executing at the computing device, wherein the third response indicates a second selection of a layout button; and
automatically controlling presentation of a representation of the first window of the second plurality of linked user interface windows using the first application in response to the second selection of the layout button wherein the presented representation of the first window includes the data field.

11. The method of claim 3, wherein storing the received name, the received data type, and the identified position for the data field includes using an extensible markup language (XML) format.

12. The method of claim 11, wherein the XML format is described using an XML schema.

13. The method of claim 3, further comprising:
receiving a third response at the second application, wherein the third response includes a data value associated with the data field and entered by the second user; and
storing the data value associated with the data field in an electronic memory.

14. The method of claim 13, further comprising:
receiving a fourth response at the second application, wherein the fourth response indicates a second selection of a first search button;
controlling presentation of a second window of the second plurality of linked user interface windows in response to the second selection of the first search button wherein the presented second window includes a first indicator associated with the data field;
receiving a fifth response at the second application, wherein the fifth response indicates a third selection of a second search button and a search value associated with the data field;
performing a search of the electronic memory based on the search value associated with the data field; and controlling presentation of a result of the performed search to the second user using the second application.

15. The method of claim 13, further comprising:
receiving a fourth response at the second application, wherein the fourth response indicates a second selection of a reporting button;
controlling presentation of a second window of the second plurality of linked user interface windows in response to the second selection of the reporting button wherein the presented second window includes a first indicator associated with the data field;
receiving a fifth response at the second application, wherein the fifth response indicates selection of the first indicator;
receiving a sixth response at the second application, wherein the sixth response includes a comparison value;
performing a search of the electronic memory based on the comparison value associated with the data field; and
controlling presentation of a result of the performed search to the second user using the second application.

16. The method of claim 15, wherein the sixth response further includes a comparison type.

17. The method of claim 16, wherein the comparison type is at least one of a greater than type, a less than type, a greater than or equal to type, a less than or equal to type, an equal to type, an inclusion in a set type, or an exclusion in a set type.

18. The method of claim 3, wherein the data type is at least one of a drop down menu type, a Boolean type, a check box type, a date type, a date and time type, an integer type, a numeric value type, a string type, a text area type, a label type, a line type, a tab type, or a group type.

19. The method of claim 18, wherein the drop down menu type is at least one of a first drop down menu type in which the user specifies a choice available for selection or a second drop down menu type in which the choice available for selection is selected from a dictionary.

* * * * *